(12) United States Patent
Loetscher et al.

(10) Patent No.: US 8,906,370 B2
(45) Date of Patent: Dec. 9, 2014

(54) ANTIBODIES AGAINST AMYLOID BETA 4 WITH GLYCOSYLATION IN THE VARIABLE REGION

(75) Inventors: Hansruedi Loetscher, Moehlin (CH); Walter Huber, Kaiseraugst (CH); Diana Schuhbauer, Basel (CH); Karl Weyer, Bad Bellingen (DE); Manfred Brockhaus, Bettingen (CH); Bernd Bohrmann, Basel (CH); Hans Koll, Oberroth (DE); Andreas Schaubmar, Penzberg (DE); Kurt Lang, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 1413 days.

(21) Appl. No.: 12/086,309

(22) PCT Filed: Dec. 11, 2006

(86) PCT No.: PCT/EP2006/011914
§ 371 (c)(1),
(2), (4) Date: May 27, 2009

(87) PCT Pub. No.: WO2007/068429
PCT Pub. Date: Jun. 21, 2007

(65) Prior Publication Data
US 2009/0252724 A1  Oct. 8, 2009

(30) Foreign Application Priority Data

Dec. 12, 2005 (EP) .................................. 05027090

(51) Int. Cl.
| A61K 39/395 | (2006.01) |
| C07K 16/18 | (2006.01) |
| A61P 25/28 | (2006.01) |
| A61K 39/00 | (2006.01) |

(52) U.S. Cl.
CPC .............. C07K 16/18 (2013.01); *C07K 2317/77* (2013.01); *A61K 2039/505* (2013.01); *C07K 2317/41* (2013.01); *C07K 2317/56* (2013.01)
USPC ..................................... 424/133.1; 530/387.3

(58) Field of Classification Search
None
See application file for complete search history.

(56) References Cited

U.S. PATENT DOCUMENTS

| 5,195,317 A | 3/1993 | Nobue et al. |
| 5,688,651 A | 11/1997 | Solomon |
| 5,955,317 A | 9/1999 | Suzuki et al. |
| 7,794,719 B2 | 9/2010 | Bardroff et al. |
| 2004/0082762 A1 | 4/2004 | Basi et al. |
| 2004/0248197 A1* | 12/2004 | Holtzman et al. ............ 435/7.1 |
| 2005/0169925 A1* | 8/2005 | Bardroff et al. ............ 424/146.1 |
| 2007/0098721 A1* | 5/2007 | Hillen et al. ............ 424/145.1 |
| 2010/0172907 A1 | 7/2010 | Bardroff et al. |
| 2011/0070225 A1* | 3/2011 | Goldbach et al. .......... 424/133.1 |

FOREIGN PATENT DOCUMENTS

| EP | 0 683 234 | 11/1995 |
| EP | 1 125 905 | 8/2001 |
| JP | HEI 03/502455 | 6/1991 |
| WO | WO 94/17197 | 8/1994 |
| WO | WO 96/20218 | 7/1996 |
| WO | WO 97/08320 | 3/1997 |
| WO | WO 99/27944 | 6/1999 |
| WO | WO 00/72880 | 12/2000 |
| WO | WO 01/15655 | 3/2001 |
| WO | WO 01/39796 | 6/2001 |
| WO | WO 02/10354 | 2/2002 |
| WO | WO 02/46237 | 6/2002 |
| WO | WO 02/064734 | 8/2002 |
| WO | WO 02/096937 | 12/2002 |
| WO | WO 03/070760 A | 8/2003 |
| WO | WO 2004/032868 A2 | 4/2004 |

OTHER PUBLICATIONS

Kuby J, ed. Immunology, Third Edn. 1997, WH Freeman & Co., New York, pp. 131-135.*
Raju TS (2003) Glycosylation variations with expression systems and their impact on biological activity of therapeutic immunoglobulins. BioProcess Int. April, pp. 44-53.*
Wright A et al. (1997) Effect of glycosylation on antibody function: implicationis for genetic engineering. Trends Biotechnol. 15:26-32.*
Endo, et al., "Glycosylation of the Variable Region of Immunoglobulin G—Site Specific Maturation of the Sugar Chains", Molecular Immunology, vol. 32, No. 13, pp. 931-940 (1995).

(Continued)

Primary Examiner — Kimberly A Ballard
(74) Attorney, Agent, or Firm — Bryan Cave LLP

(57) ABSTRACT

The present invention relates to a purified antibody molecule preparation being characterized in that at least one antigen binding site comprises a glycosylated asparagine (Asn) in the variable region of the heavy chain ($V_H$). More specifically, a pharmaceutical and a diagnostic composition comprising said antibody molecule and antibody mixtures are provided which is/are capable of specifically recognizing the β-A4 peptide/Aβ4. The present invention relates in particular to a mixture of antibodies comprising one or two glycosylated antigen binding sites with a glycosylated asparagine (Asn) in the variable region of the heavy chain, i.e. mixtures of isoforms of antibodies which comprise a glycosylated Asn in the variable region of the heavy chain ($V_H$). Also disclosed are compositions or antibody preparations comprising the specifically glycosylated antibody isoforms. Furthermore, the pharmaceutical and diagnostic uses for these antibodies are provided. The antibody isoforms may for example be used in the pharmaceutical intervention of amyloidogenesis or amyloid-plaque formation and/or in the diagnosis of the same.

13 Claims, 40 Drawing Sheets

(56) References Cited

OTHER PUBLICATIONS

Leibiger, et al., "Variable domain-linked oligosaccharides of a human monoclonal IgG: structure and influence on antigen binding", Biochem. J., vol. 338, pp. 529-538 (1999).
Routier, et al., "The glycosylation pattern of a humanized IgGI antibody (D1.3) expressed in CHO cells", Glycoconjugate Journal, vol. 14, pp. 201-207 (1997).
Sheeley, et al., "Characterization of Monoclonal Antibody Glycosylation: Comparison of Expression Systems and identification of Terminal alpha-Linked Galactose", Analytical Biochemistry, vol. 247, pp. 102-110 (1997).
Coloma, et al., "Position Effects of Variable Region Carbohydrate on the Affinity and in Vivo Behavior of an Anti-(1→6) Dextran Antibody", J. Immunology, vol. 162, pp. 2162-2170 (1999).
Office Action issued by the Russian Patent Office, dated Sep. 23, 2010.
English translation of Office Action issued by the Russian Patent Office, dated Sep. 23, 2010.
Office Action issued by the Russian Patent Office, dated Mar. 23, 2011.
English translation of Office Action issued by the Russian Patent Office, dated Mar. 23, 2011.
Examiner's First Report issued by the Australian Patent Office, dated Aug. 23, 2010.
Office Action issued by the Chilean Patent Office, dated Dec. 11, 2006.
English translation of Office Action issued by the Chilean Patent Office, dated Dec. 11, 2006.
Office Action issued by the State Intellectual Property Office of The PRC, dated Dec. 28, 2010.
English translation of Office Action issued by the State Intellectual Property Office of The PRC, dated Dec. 28, 2010.
Office Action and Search Report issued by the Taiwanese Patent Office dated Jul. 22, 2009.
English translation of Office Action and Search Report issued by the Taiwanese Patent Office, dated Jul. 22, 2009.
English translation of Office Action—Preliminary Examination Report issued by the Ukrainian Patent Office, dated Jun. 14, 2011.
Communication Pursuant to Article 94(3) EPC issued by the European Patent Office, dated Sep. 2, 2009.
Notice of the Result of Substantive Examination of a Patent Application issued by the Patents Office of the Cooperation Council for the Arab States of the Gulf GCC, dated Jan. 2, 2010.
English translation of Notice of the Result of Substantive Examination of a Patent Application issued by the Patents Office of the Cooperation Council for the Arab States of the Gulf GCC, dated Jan. 2, 2010.
Examination Report with International Search Report and Abstract issued by the State Intellectual Property Office of The PRC, dated Aug. 10, 2009.
English translation of Office Action issued by Israeli Patent Office dated Jul. 14, 2010.
English translation of Notice of Preliminary Rejection and cited references issued by the Korean Patent Office, dated Jan. 13, 2011.
Office Action issued by the Mexican Patent Office, dated Mar. 18, 2011.
English translation of Office Action issued by the Mexican Patent Office, dated Mar. 18, 2011.
Office Action issued by the New Zealand Patent Office, dated Apr. 13, 2010.
English translation of Office Action issued by the Pakistani Patent Office, dated May 12, 2008.
English translation of Office Action issued by the Pakistani Patent Office, dated Jul. 30, 2009.
Cover page with English translation of Office Action issued by the Peruvian Patent Office, dated Feb. 10, 2010.
Singapore Examination Report issued by the Danish Patent Office, dated Jan. 3, 2011.
Singapore Written Opinion and Search Report issued by the Danish Patent Office, dated Feb. 10, 2010.
Office Action issued by Canadian Patent Office, dated Oct. 31, 2011.
O'Nuallain et al., "Confrontational Abs Recognizing a Generic Amyloid Fibril Epitope," PNAS, vol. 99, No. 3, pp. 1485-1490 (2002).
Ghoshal et al., "Tau-66: Evidence for a Novel Tau Conformation in Alzheimer's Disease," Journal of Neurochemistry, vol. 77, pp. 1372-1385 (2001).
Knappik et al., "Fully Synthetic Human Combinatorial Antibody Libraries (HuCAL) Based on Modular Consensus Frameworks and CDRs Randomized with Trinucleotides," J. Mol. Biol., vol. 296, pp. 57-86 (2000).
Solomon et al., "Vaccination for the Prevention and Treatment of Alzheimer's Disease," Drugs of Today, vol. 36, No. 9, pp. 655-663 (2000).
Cribbs et al., "Adjuvant-Dependent Modulation of Th1 and Th2 Responses to Immunization with β-Amyloid," International Immunology, vol. 15, No. 4, pp. 505-514 (2003).
Cheong et al., "Affinity enhancement of bispecific antibody against two different epitopes in the same antigen," Biochemical and Biophysical Research Communications, vol. 173, pp. 795-800 (1990).
Frenkel et al., "High affinity binding of monoclonal antibodies to the sequential epitope EFRH of β-amyloid peptide is essential for modulation of fibrillar aggregation," Journal of Neuroimmunology, vol. 95, pp. 136-142 (1999).
Frenkel et al., "Immunization against Alzheimer's β-amyloid plaques via EFRH phage administration," Proc. Natl. Acad. Sci., vol. 97, pp. 11455-11459 (2000).
Solomon et al., "Disaggregation of Alzheimer β-amyloid by site-directed mAb," Proc. Natl. Acad. Sci., vol. 94, pp. 4109-4112 (1997).
Solomon et al., "Monoclonal antibodies inhibit in vitro fibrillar aggregation of the Alzheimer β-amyloid peptide," Proc. Natl. Acad. Sci., vol. 93, pp. 452-455 (1996).
Schier et al., "Isolation of Picomolar Affinity Anti-c-erbB-2 Single-chain Fv by Molecular Evolution of the Complementarity Determining Regions in the Center of the Antibody Binding Site," J. Mol. Biol., vol. 263, 551-567 (1996).
Kay et al., "An M13 Phage library displaying random 38-amino-acid peptides as a source of novel sequences with affinity to selected targets," Gene, vol. 128, pp. 59-65 (1993).
Frenkel et al., "N-terminal EFRH sequence of Alzheimer's β-amyloid peptide represents the epitope of its anti-aggregating antibodies," Journal of Neuroimmunology, vol. 88, pp. 85-90 (1998).
Solomon et al., "Activity of monoclonal antibodies in prevention of in vitro aggregation of their antigens," Stability and Stabilization of Biocatalysts, pp. 183-188 (1998).
Rudikoff et al., "Single amino acid substitution altering antigen-binding specificity," Proc. Natl. Acad. Sci. USA, vol. 79, pp. 1979-1983 (1982).
Paul, Fundamental Immunology, 3rd Edition, pp. 292-295 (1993).
English translation of Notice of Grounds for Rejection in Japanese Patent Application No. 2009-053951, dispatched on Aug. 11, 2011.
Office Action issued by the Taiwan Patent Office in ROC (Taiwan) Patent Application No. 095146304, dated Aug. 20, 2012.
English translation of Office Action issued by the Taiwan Patent Office in ROC (Taiwan) Patent Application No. 095146304, dated Aug. 20, 2012.
Office Action issued by the Malaysian Patent Office in Application No. PI 20081349, dated Nov. 14, 2012.
Office Action issued by the Colombian Patent Office in Application No. 2008 049920-A, dated Sep. 6, 2012.

\* cited by examiner

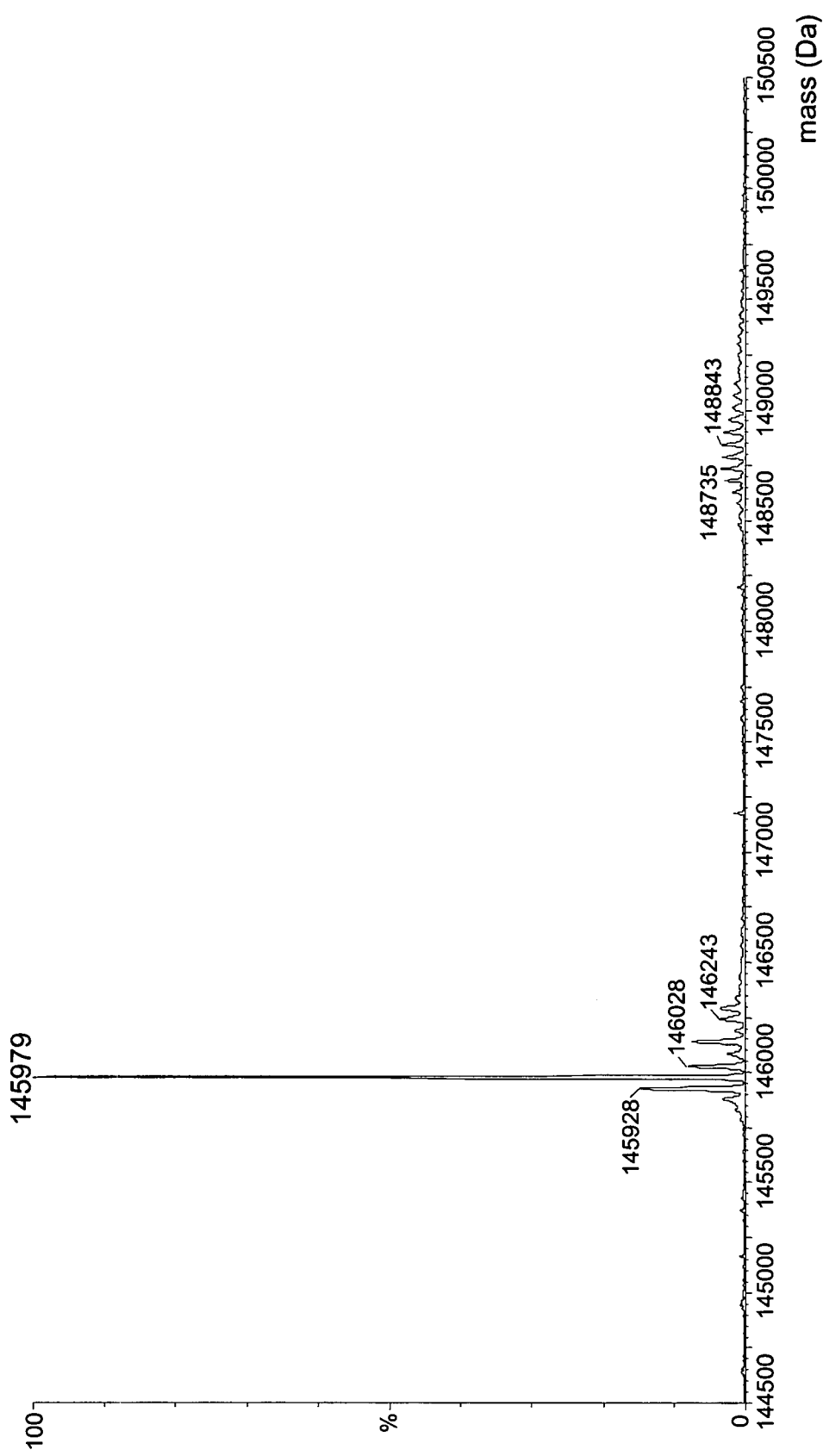
Figure 4A   non-glycosylated ANTIBODY A

Figure 4B    mono-glycosylated ANTIBODY A

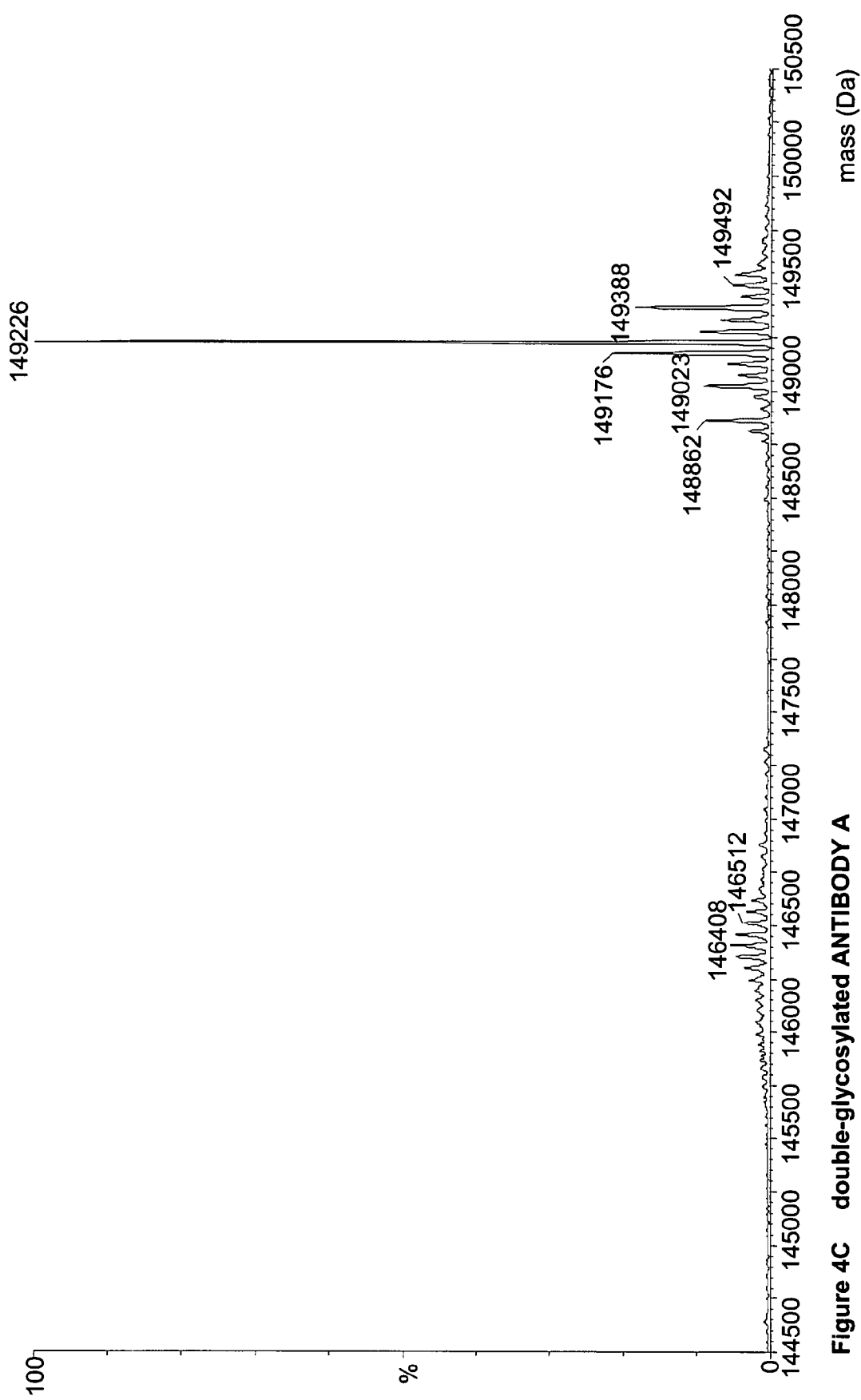
Figure 4C  double-glycosylated ANTIBODY A

A
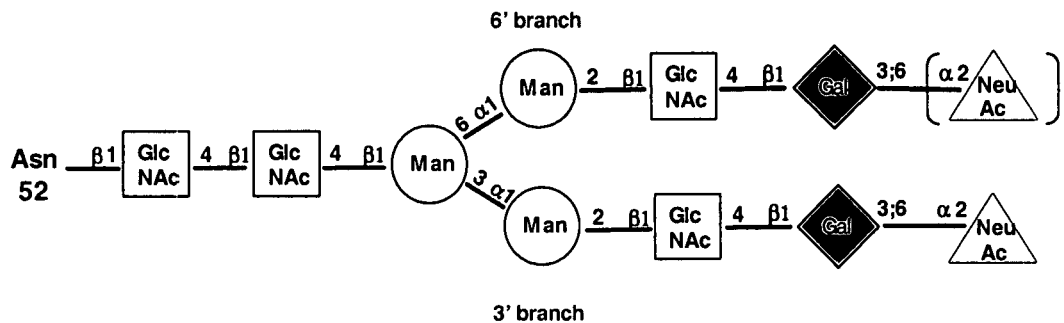
B
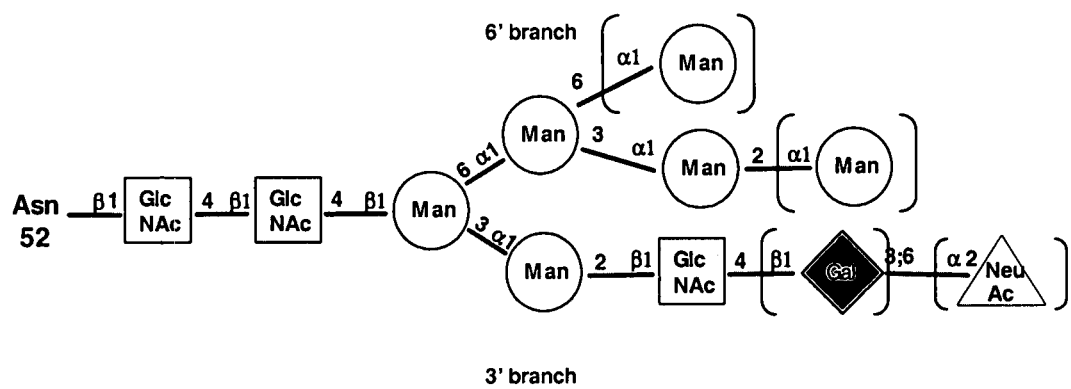
C
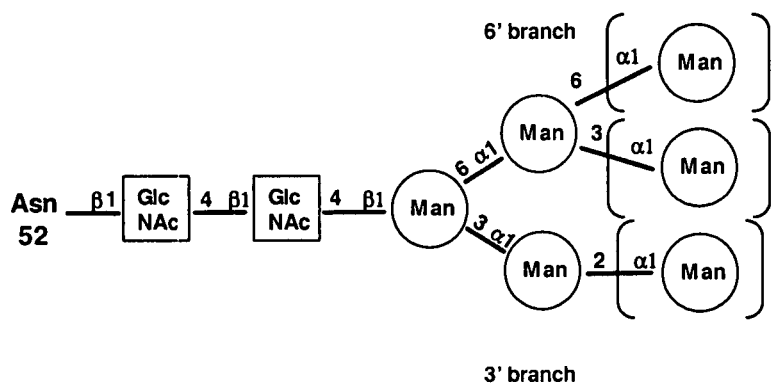
Figure 5

| Name | Structure[1] | Name[2] | Structure[1] |
|---|---|---|---|
| Asn 306_G0 | | Asn 52_G2_0NANA-F | |
| Asn 306_G0-GlcNac | | Asn 52_G2_1NANA-F | |
| Asn 306_G1 | | Asn 52_G2_2NANA-F | |
| Asn 306_G2 | | Asn 52_hyb_Man5_1NANA | |
| Asn 306_G0-F | | Asn 52_hyb_Man4_1NANA | |
| Asn 306_G1-F | | Asn 52_hyb_Man3_1NANA | |
| Asn 306_G2-F | | Asn 52_Man5 | |
| Asn 306_Man5 | | | |

[1] Fucose △, Mannose ●, N-Acetylglucosamine ☐, Galactose○, N-Acetylneuraminic acid ◇
[2] "hyb" denotes hybrid structures

Figure 27

ANTIBODIES AGAINST AMYLOID BETA 4 WITH GLYCOSYLATION IN THE VARIABLE REGION

CROSS-REFERENCE TO RELATED APPLICATIONS

This application is the National Stage of International Application No. PCT/EP2006/011914, filed Dec. 11, 2006, which claims priority to EP Application No. 05 02 7090.9, filed Dec. 12, 2005.

FIELD OF THE INVENTION

The present invention relates to a purified antibody molecule preparation being characterized in that at least one antigen binding site comprises a glycosylated asparagine (Asn) in the variable region of the heavy chain ($V_H$). More specifically, a purified antibody molecule is provided which is capable of specifically recognizing the β-A4 peptide/Aβ4 and comprising a glycosylation in the variable region of the heavy chain ($V_H$). The present invention relates to a mixture of antibodies comprising one or two glycosylated antigen binding sites with a glycosylated asparagine (Asn) in the variable region of the heavy chain, i.e. mixtures of isoforms of antibodies which comprise a glycosylated Asn in the variable region of the heavy chain ($V_H$). Also disclosed are compositions or antibody preparations comprising the specifically glycosylated antibody isoforms. Furthermore, the pharmaceutical and diagnostic uses for these antibodies are provided. The antibody isoforms may for example be used in the pharmaceutical intervention of amyloidogenesis or amyloid-plaque formation and/or in the diagnosis of the same.

INCORPORATION BY REFERENCE OF SEQUENCE LISTING

This application contains references to amino acids and/or nucleic acid sequences that have been submitted as sequence listing text file "0219887substitute2.txt", file size of 44.6 KB, created on Sep. 15, 2011. The aforementioned sequence listing is hereby incorporated by reference in its entirety pursuant to 37 C.F.R. §1.52(e)(5).

BACKGROUND OF THE INVENTION

About 70% of all cases of dementia are due to Alzheimer's disease which is associated with selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and defused halos.

The extracellular neuritic plaques contain large amounts of a pre-dominantly fibrillar peptide termed "amyloid β", "A-beta", "Aβ4", "β-A4" or "Aβ"; see Selkoe (1994), Ann. Rev. Cell Biol. 10, 373-403, Koo (1999), PNAS Vol. 96, pp. 9989-9990, U.S. Pat. No. 4,666,829 or Glenner (1984), BBRC 12, 1131. This amyloid β is derived from "Alzheimer precursor protein/β-amyloid precursor protein" (APP). APPs are integral membrane glycoproteins (see Sisodia (1992), PNAS Vol. 89, pp. 6075) and are endoproteolytically cleaved within the Aβ sequence by a plasma membrane protease, α-secretase (see Sisodia (1992), loc. cit.). Furthermore, further secretase activity, in particular β-secretase and γ-secretase activity leads to the extracellular release of amyloid-β (Aβ) comprising either 39 amino acids (Aβ39), 40 amino acids (Aβ40), 42 amino acids (Aβ42) or 43 amino acids (Aβ43); see Sinha (1999), PNAS 96, 11094-1053; Price (1998), Science 282, 1078 to 1083; WO 00/72880 or Hardy (1997), TINS 20, 154.

It is of note that Aβ has several naturally occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVFFAEDVG-SNKGAIIGLMVGGVVIA (SEQ ID NO: 3). In Aβ41, Aβ40, Aβ39, the C-terminal amino acids A, IA and VIA are missing, respectively. In the Aβ43-form an additional threonine residue is comprised at the C-terminus of the above depicted sequence (SEQ ID NO: 3).

The time required to nucleate Aβ40 fibrils was shown to be significantly longer than that to nucleate Aβ42 fibrils; see Koo, loc. cit. and Harper (1997), Ann. Rev. Biochem. 66, 385-407. As reviewed in Wagner (1999), J. Clin. Invest. 104, 1239-1332, the Aβ42 is more frequently found associated with neuritic plaques and is considered to be more fibrillogenic in vitro. It was also suggested that Aβ42 serves as a "seed" in the nucleation-dependent polymerization of ordered non-crystalline Aβ peptides; Jarrett (1993), Cell 93, 1055-1058.

Modified APP processing and/or the generation of extracellular plaques containing proteinaceous depositions are not only known from Alzheimer's pathology but also from subjects suffering from other neurological and/or neurodegenerative disorders. These disorders comprise, inter alia, Down's syndrome, Hereditary cerebral hemorrhage with amyloidosis Dutch type, Parkinson's disease, ALS (amyotrophic lateral sclerosis), Creutzfeld Jacob disease, HIV-related dementia and motor neuropathy.

Until now, only limited medical intervention schemes for amyloid-related diseases have been described. For example, cholinesterase inhibitors like galantamine, rivastigmine or donepezil have been discussed as being beneficial in Alzheimer's patients with only mild to moderate disease. However, also adverse events have been reported due to cholinergic action of these drugs. While these cholinergic-enhancing treatments do produce some symptomatic benefit, therapeutic response is not satisfactory for the majority of patients treated. It has been estimated that significant cognitive improvement occurs in only about 5% of treated patients and there is little evidence that treatment significantly alters the course of this progressive disease. Consequently, there remains a tremendous clinical need for more effective treatments and in particular those which may arrest or delay progression of the disease.

Also NMDA-receptor antagonists, like memantine, have been employed more recently. However, adverse events have been reported due to the pharmacological activity. Further, such a treatment with these NMDA-receptor antagonists can merely be considered as a symptomatic approach and not a disease-modifying one.

Also immunomodulation approaches for the treatment of amyloid-related disorders have been proposed. WO 99/27944 discloses conjugates that comprise parts of the Aβ peptide and carrier molecules whereby said carrier molecule should enhance an immune response. Another active immunization approach is mentioned in WO 00/72880, wherein also Aβ fragments are employed to induce an immune response.

Also passive immunization approaches with general anti-Aβ antibodies have been proposed in WO 99/27944 or WO 01/62801 and specific humanized antibodies directed against portions of Aβ have been described in WO 02/46237, WO 02/088306 and WO 02/088307. WO 00/77178 describes antibodies binding a transition state adopted by β-amyloid during hydrolysis. WO 03/070760 discloses antibody molecules that recognize two discontinuous amino acid sequences on the Aβ peptide.

WO 03/016466 describes a humanized anti-Aβ antibody which is modified in order to avoid any potential glycosylation in its heavy chain, since a glycosylation in variable region(s) of antibodies has been postulated in Wallick (1988) J. Exp. Med. 168, 1099-1109.

The technical problem underlying the present invention is to provide efficacious means and methods in the medical management of amyloid disorders, in particular means and methods for the reduction of detrimental amyloid plaques in patients in need of a (corresponding) medical intervention.

BRIEF SUMMARY OF THE INVENTION

In a first aspect, the present invention provides a purified antibody molecule being characterized in that at least one antigen binding site comprises a glycosylated asparagine (Asn) in the variable region of the heavy chain ($V_H$). The inventive, purified antibody or the antibody composition as provided herein is in particular directed against Aβ and/or a fragment of Aβ. The purified antibody molecule as provided herein and in particular the antibody composition or antibody preparation of the invention is useful in the preparation of a pharmaceutical or diagnostic composition for the treatment, amelioration and for prevention of a disease associated with amyloidosis and/or amyloid plaque formation. An example of such disease is Alzheimer's disease.

DETAILED DESCRIPTION OF THE INVENTION

In context of this invention it was surprisingly found that purified antibody molecules, wherein at least one antigen binding site comprises an N-linked glycosylation in the variable region of the heavy chain, is particularly useful in e.g. the reduction of amyloid plaques. Furthermore, it has been found in context of this invention that the glycosylated antibodies or antibody compositions as provided herein are particularly useful and efficacious in crossing the blood-brain barrier/blood brain border in vivo as illustrated by very efficacious plaque binding.

This is in stark contrast to the teachings of the prior art. WO 03/016466 discloses antibodies that are specifically engineered to lack an N-glycosylation site in the heavy chain and it is taught that glycosylation in variable region framework has negative effect on antibody binding affinity. It is taught in the prior art that the described anti-Aβ antibody in a deglycosylated form of the heavy chain variable CDR2 region has a markedly higher affinity for synthetic and purified Aβ peptide in vitro.

Accordingly, the present invention relates to an improved, purified antibody molecule or an antibody preparation, in particular an antibody molecule preparation that is directed against the Aβ4/Aβ peptide (amyloid β) and is highly efficient in vivo. The improvement of the present antibody molecule/antibody preparation lies in the provision of purified antibody molecules which comprise in at least one of their variable regions in the heavy chain an N-glycosylation, e.g. in the CDR2 region of said variable region of the heavy chain. As mentioned above, this is in contrast to the prior art like WO 03/016466 that teaches that such an N-glycosylation has to be avoided in antibodies directed against, e.g. Aβ.

Examples of an antibody molecule of the present invention are immunoglobulin molecules, e.g. IgG molecules. IgGs are characterized in comprising two heavy and two light chains (illustrated for example in FIG. 14) and these molecules comprise two antigen binding sites. Said antigen binding sites comprise "variable regions" consisting of parts of the heavy chains ($V_H$) and parts of the light chains ($V_L$). The antigen-binding sites are formed by the juxtaposition of the $V_H$ and $V_L$ domains. For general information on antibody molecules or immunoglobulin molecules see also common textbooks, like Abbas "Cellular and Molecular Immunology", W.B. Sounders Company (2003).

In one aspect, for example in provision of an immunoglobulin molecule as characterized in this invention, an antibody is described wherein one antigen binding site comprises a glycosylated asparagine (Asn) in the corresponding variable region of the heavy chain ($V_H$). Said antibody is hereinafter referred to as "mono-glycosylated ANTIBODY"; see also FIG. 14.

In another aspect, an immunoglobulin molecule is provided wherein both antigen binding sites comprise a glycosylated asparagine (Asn) in the variable region of corresponding heavy chains ($V_H$). Said antibody molecule is hereinafter referred to as "double-glycosylated ANTIBODY", see FIG. 14.

An immunoglobulin wherein no antigen binding site comprises a glycosylated asparagine (Asn) in the variable region of the heavy chain ($V_H$) is hereinafter referred to as "non-glycosylated ANTIBODY".

The mono-glycosylated ANTIBODY, the double-glycosylated ANTIBODY and the non-glycosylated ANTIBODY may comprise the identical amino acid sequences or different amino acid sequences. The term "ANTIBODY" comprises, accordingly, antibody molecules, in particular recombinantly produced antibody molecules, like immunoglobulins. However, as discussed below, the term "ANTIBODY molecule(s)" also comprises known isoforms and modifications of immunoglobulins, like single-chain antibodies or single chain Fv fragments (scAB/scFv) or bispecific antibody constructs, said isoforms and modifications being characterized as comprising at least one glycosylated $V_H$ region as defined herein. A specific example of such an isoform or modification may be a sc (single chain) antibody in the format $V_H$-$V_L$ or $V_L$-$V_H$, wherein said $V_H$ comprises the herein described glycosylation. Also bispecific scFvs are envisaged, e.g. in the format $V_H$-$V_L$-$V_H$-$V_L$, $V_L$-$V_H$-$V_H$-$V_L$, $V_H$-$V_L$-$V_L$-$V_H$, which comprise the herein described glycosylation in the CDR-2 region.

In context of this invention, the term "ANTIBODY" in capital letters is employed in order to provide for better lucidity. However, the term "antibody" used in small letters is also used in context of this application. "ANTIBODY"/"ANTIBODIES"/"antibody" and "antibodies" are used interchangeably.

The mono-glycosylated ANTIBODY and the double-glycosylated ANTIBODY are herein before referred to as "glycosylated ANTIBODY isoforms". A purified antibody molecule characterized in that at least one antigen binding site comprises a glycosylated asparagine (Asn) in the variable region of the heavy chain ($V_H$) is a mono-glycosylated ANTIBODY which is free of or to a very low extent associated with an isoform selected from a double-glycosylated ANTIBODY and a non-glycosylated ANTIBODY, i.e. a "purified mono-glycosylated ANTIBODY". A double-glycosylated ANTIBODY in context of this invention is free of or to a very low extent associated with an isoform selected from a mono-glycosylated ANTIBODY and a non-glycosylated ANTIBODY, i.e. a "purified double-glycosylated ANTIBODY".

The term "which is free of or to a very low extent" denotes the complete absence of the respective other (glycosylation) isoforms or a presence of another (glycosylated) isoform in a concentration of at the most 10%, e.g. at the most 5%, e.g. at the most 4%, e.g. at the most 3%, e.g. at the most 2%, e.g. at the most 1%, e.g. at the most 0.5%, e.g. at the most 0.3%, e.g. at the most 0.2%. Further information in this regard is provided below and in the appended examples.

In context of this invention, the term "mono-glycosylated antibody(ies)" or "mono-glycosylated ANTIBODY(IES)" relates to antibody molecules comprising an N-glycosylation in one ($V_H$)-region of an individual antibody molecule, e.g. of an immunoglobulin, e.g. an IgG, e.g. of an IgG1. For example, said "mono-glycosylated form", comprises a glycosylation on one variable region of the heavy chain e.g. at position asparagine "Asn 52" as defined below. This "mono-glycosylated IgG1-form or mono-glycosylated isoform" may also comprise, as illustrated herein, the glycosylation in the well conserved glycosylation site in the Fc-part, for example asparagine Asn 306 in the non-variable Fc-part.

The term "double-glycosylated antibody(ies)" or "double-glycosylated ANTIBODY(IES)" in the meaning of this invention comprises the herein defined glycosylation on both variable regions of the heavy chain ($V_H$)-region. Again, this "double glycosylated form", comprises a glycosylation on the variable region of both heavy chains, in particular at position asparagine Asn 52 as detailed below and as exemplified in the appended examples. This "double-glycosylated IgG1-form or double-glycosylated isoform" may also comprise, as illustrated herein, the glycosylation in the well conserved glycosylation site in the non-variable/constant Fc-part, in particular on position 306 of the exemplified immunoglobulin. Appended FIG. 14 illustrates corresponding antibody molecules.

Antibodies devoid of such a post-translational modification in the variable region, e.g. in both variable regions of the heavy chain (both ($V_H$)-regions) are, in context of this invention considered as a "non-glycosylated form", comprising no glycosylation in the variable region of the heavy chain. Yet, this "non-glycosylated form" may nevertheless comprise (a) glycosylation(s) in the constant region (C-region) of the antibody, for example, and most commonly at the well conserved glycosylation site of the Fc-part, in particular the asparagine (Asn) 306 in the non-variable/constant Fc-part as defined herein, see also SEQ ID NO: 6.

The glycosylated asparagine (Asn) in the variable region of the heavy chain ($V_H$) may be in the complementarity determining region 2 (CDR2 region). Said glycosylated asparagine (Asn) in the variable region of the heavy chain ($V_H$) may be in position 52 of the variable region as defined below and as shown in SEQ ID No. 2 (or in position 52 of SEQ ID NO: 6 comprising also the Fc-part of an antibody heavy chain as disclosed herein).

ANTIBODY isoforms may also comprise (a) further glycosylation(s) in the constant/non-variable part of the antibody molecules, e.g. in the Fc-part of an IgG, e.g. in the Fc-part in an IgG1. Said glycosylation in the Fc-part relates to a well conserved glycosylation, being characterized in located on position Asn306 of the heavy chain, e.g., in accordance with the following sequence:

```
                                              (SEQ ID NO: 6)
QVELVESGGGLVQPGGSLRLSCAASGFTFSSYAMSWVRQAPGKGLEWVSA

INASGTRTYYADSVKGRFTISRDNSKNTLYLQMNSLRAEDTAVYYCARGK

GNTHKPYGYVRYFDVWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK
```

This sequence is also depicted herein below and the CDRs, CH-regions, heavy regions as well as two N-glycosylation sites (N52 and N306) are indicated:

```
QVELVESGGGLVQPGGSLRLSCAAS GFTFSSYAMS WVRQAPGKGLEWVS
 AINASGTRTYYADSVKG RFTISRDNSKNTLYLQMNSLRAEDTAVYYCAR
 GKGNTHKPYGYVRYFDV WGQGTLVTVSS ASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKV EPKSCDKTHTCPP PCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGK (SEQ ID NO:6)

framed: CDR1, 2, 3
underlined: CH1
italics: hinge
underlined twice: CH2
dotted underlined: CH3
bold N: N-linked glycosylation sites
```

The IgG-Fc region of the antibodies of this invention may be a homodimer comprised of inter-chain disulphide bonded hinge regions, glycosylated $C_H2$ domains, bearing N-linked oligosaccharide at asparagine 306 (Asn-306) of the $C_H2$ and non-covalently paired $C_H3$ domains. The oligosaccharide of the glycosylation at Asn-306 is of the complex biantennary type and may comprise a core heptasaccharide structure with variable addition of outer arm sugars.

The oligosaccharide influences or determines Fc structure and function (Jefferis (1998) Immunol Rev. 163, 50-76). Effector functions, numbering particular specific IgG-Fc/effector ligand interactions have been discussed (Jefferis (2002) Immunol Lett. 82(1-2), 57-65 and Krapp (2003) J Mol. Biol. 325(5), 979-89). This conserved Fc-position Asn-306 corresponds to "Asn-297" in the Kabat-system (Kabat (1991) Sequences of Proteins of Immunological Interest, 5th Ed., Public Health Service, National Institutes of Health, Bethesda Md.)

The exemplified heavy chain may be encoded by the following sequence:

(SEQ ID NO: 5)
caggtggaattggtggaaagcggcggcggcctggtgcaaccgggcggcag
cctgcgtctgagctgcgcggcctccggatttaccttttagcagctatgcga
tgagctgggtgcgccaagcccctgggaagggtctcgagtgggtgagcgct
attaatgcttctggtactcgtacttattatgctgattctgttaagggtcg
ttttaccatttcacgtgataattcgaaaaacaccctgtatctgcaaatga
acagcctgcgtgcggaagatacggccgtgtattattgcgcgcgtggtaag
ggtaatactcataagccttatggttatgttcgttattttgatgtttgggg
ccaaggcaccctggtgacggttagctcagcctccaccaagggtccatcgg
tcttcccctggcaccctcctccaagagcacctctggggcacagcggcc
ctgggctgcctggtcaaggactacttccccgaaccggtgacggtgtcgtg
gaactcaggcgccctgaccagcggcgtgcacaccttcccggctgtcctac
agtcctcaggactctactccctcagcagcgtggtgaccgtgccctccagc
agcttgggcacccagacctacatctgcaacgtgaatcacaagcccagcaa
caccaaggtggacaagaaagttgagcccagatatcgtgcgatatcgtgca
atcttgtgacaaaactcacacatgcccaccgtgcccagcacctgaactcc
tggggggaccgtcagtcttcctcttccccccaaaacccaaggacaccctc
atgatctcccggacccctgaggtcacatgcgtggtggtggacgtgagcca
cgaagaccctgaggtcaagttcaactggtacgtggacggcgtggaggtgc
ataatgccaagacaaagccgcgggaggagcagtacaacagcacgtaccgg
gtggtcagcgtcctcaccgtcctgcaccaggactggctgaatggcaagga
gtacaagtgcaaggtctccaacaaagccctcccagccccatcgagaaaa
ccatctccaaagccaaagggcagccccgagaaccacaggtgtacaccctg
cccccatcccgggatgagctgaccaagaaccaggtcagcctgacctgcct
ggtcaaaggcttctatcccagcgacatcgccgtggagtgggagagcaatg
ggcagccggagaacaactacaagaccacgcctcccgtgctggactccgac
ggctccttcttcctctacagcaagctcaccgtggacaagagcaggtggca
gcaggggaacgtcttctcatgctccgtgatgcatgaggctctgcacaacc
actacacgcagaagagcctctccctgtctccgggtaaatga.

Said heavy chain may also comprise (in particular during its recombinant production) additional sequences, like "leader sequences". A corresponding example is encoded by the following sequence:

(SEQ ID NO: 25)
atgaaacacctgtggttcttcctcctgctggtggcagctcccagatgggt
cctgtcc (followed by) caggtggaattggtggaaagcggcggcg
gcctggtgcaaccgggcggcagcctgcgtctgagctgcgcggcctccgga
tttaccttttagcagctatgcgatgagctgggtgcgccaagcccctgggaa
gggtctcgagtgggtgagcgctattaatgcttctggtactcgtacttatt
atgctgattctgttaagggtcgttttaccatttcacgtgataattcgaaa
aacaccctgtatctgcaaatgaacagcctgcgtgcggaagatacggccgt
gtattattgcgcgcgtggtaagggtaatactcataagccttatggttatg
ttcgttattttgatgtttgggggccaaggcaccctggtgacggttagctca
gcctccaccaagggtccatcggtcttcccctggcaccctcctccaagag
cacctctggggcacagcggccctgggctgcctggtcaaggactacttcc
ccgaaccggtgacggtgtcgtggaactcaggcgccctgaccagcggcgtg
cacaccttcccggctgtcctacagtcctcaggactctactccctcagcag
cgtggtgaccgtgccctccagcagcttgggcacccagacctacatctgca
acgtgaatcacaagcccagcaacaccaaggtggacaagaaagttgagccc
aaatcttgtgacaaaactcacacatgcccaccgtgcccagcacctgaact
cctggggggaccgtcagtcttcctcttccccccaaaacccaaggacaccc
tcatgatctcccggacccctgaggtcacatgcgtggtggtggacgtgagc
cacgaagaccctgaggtcaagttcaactggtacgtggacggcgtggaggt
gcataatgccaagacaaagccgcgggaggagcagtacaacagcacgtacc
gggtggtcagcgtcctcaccgtcctgcaccaggactggctgaatggcaag
gagtacaagtgcaaggtctccaacaaagccctcccagccccatcgagaa
aaccatctccaaagccaaagggcagccccgagaaccacaggtgtacaccc
tgcccccatcccgggatgagctgaccaagaaccaggtcagcctgacctgc
ctggtcaaaggcttctatcccagcgacatcgccgtggagtgggagagcaa
tgggcagccggagaacaactacaagaccacgcctcccgtgctggactccg
acggctccttcttcctctacagcaagctcaccgtggacaagagcaggtgg
cagcaggggaacgtcttctcatgctccgtgatgcatgaggctctgcacaa
ccactacacgcagaagagcctctccctgtctccgggtaaatga the corresponding amino acid sequence would be:

(SEQ ID NO: 26)
MKHLWFFLLLVAAPRWVLS (followed by) QVELVESGGGLVQPGG
SLRLSCAASGFTFSSYAMSWVRQAPGKGLEWVSAINASGTRTYYADSVKG
RFTISRDNSKNTLYLQMNSLRAEDTAVYYCARGKGNTHKPYGYVRYFDVW
GQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLT -continued

VLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLY

SKLTVDKSRWQQGNVFSCSVMHEALHNHYTQKSLSLSPGK

The above sequence also comprises a "signal peptide" said signal peptide is proteolytically cleaved by the host signal peptidase during the secretory pathway during the production of the inventive antibody molecules in host cells, like CHO cells.

Alternatively, said heavy chain may be encoded by a nucleic acid sequence that is optimized for recombinant production as exemplified by the following sequence:

```
  1 atggagtttg gctgagctg gttttcctc gttgctcttt taagaggtga
 51 ttcatggaga aatagagaga ctgagtgtga gtgaacatga gtgagaaaaa
101 ctggatttgt gtggcatttt ctgataacgg tgtccttctg tttgcaggtg
151 tccagtgt
``` followed by (SEQ ID NO: 23)
```
         ca ggtggagctg gtggagtctg ggggaggcct ggtccagcct
 201 gggggtccc tgagactctc ctgtgcagcg tctggattca ccttcagtag
 251 ctatgccatg agctgggtcc gccaggctcc aggcaagggg ctcgagtggg
 301 tgtccgccat aaacgccagc ggtacccgca cctactatgc agactccgtg
 351 aagggccgat tcaccatctc cagagacaat tccaagaaca cgctgtatct
 401 gcaaatgaac agcctgagag ccgaggacac ggctgtgtat tactgtgcga
 451 gaggcaaggg gaacacccac aagccctacg gctacgtacg ctactttgac
 501 gtgtggggcc aaggaaccct ggtcaccgtc tcctcaggtg agtcctcaca
 551 acctctctcc tgcggccgca gcttgaagtc tgaggcagaa tcttgtccag
 601 ggtctatcgg actcttgtga gaattagggg ctgacagttg atggtgacaa
 651 tttcagggtc agtgactgtc tggtttctct gaggtgagac tggaatatag
 701 gtcaccttga agactaaaga ggggtccagg ggcttttctg cacaggcagg
 751 gaacagaatg tggaacaatg acttgaatgg ttgattcttg tgtgacacca
 801 agaattggca taatgtctga gttgcccaag ggtgatctta gctagactct
 851 ggggtttttg tcgggtacag aggaaaaacc cactattgtg attactatgc
 901 tatggactac tggggtcaag gaacctcagt caccgtctcc tcaggtaaga
 951 atggcctctc caggtctttta tttttaacct ttgttatgga gttttctgag
1001 cattgcagac taatcttgga tatttgccct gagggagccg gctgagagaa
1051 gttgggaaat aaatctgtct agggatctca gagcctttag gacagattat
1101 ctccacatct ttgaaaaact aagaatctgt gtgatggtgt tggtggagtc
1151 cctggatgat gggataggga cttcggaggc tcatttgagg gagatgctaa
1201 aacaatccta tggctggagg gatagttggg gctgtagttg gagattttca
1251 gtttttagaa tgaagtatta gctgcaatac ttcaaggacc acctctgtga
1301 caaccatttt atacagtatc caggcatagg gacaaaaagt ggagtggggc
1351 actttcttta gatttgtgag gaatgttcca cactagattg tttaaaactt
1401 catttgttgg aaggagctgt cttagtgatt gagtcaaggg agaaaggcat
1451 ctagcctcgg tctcaaaagg gtagttgctg tctagagagg tctggtggag
1501 cctgcaaaag tccagctttc aaaggaacac agaagtatgt gtatggaata
1551 ttagaagatg ttgcttttac tcttaagttg gttcctagga aaaatagtta
```

-continued

```
1601  aatactgtga ctttaaaatg tgagagggtt ttcaagtact catttttttta
1651  aatgtccaaa attttttgtca atcaatttga ggtcttgttt gtgtagaact
1701  gacattactt aaagtttaac cgaggaatgg gagtgaggct ctctcatacc
1751  ctattcagaa ctgacttta acaataataa attaagttta aaatattttt
1801  aaatgaattg agcaatgttg agttgagtca agatggccga tcagaaccgg
1851  aacacctgca gcagctggca ggaagcaggt catgtggcaa ggctatttgg
1901  ggaagggaaa ataaaaccac taggtaaact tgtagctgtg gtttgaagaa
1951  gtggttttga aacactctgt ccagccccac caaaccgaaa gtccaggctg
2001  agcaaaacac cacctgggta atttgcattt ctaaaataag ttgaggattc
2051  agccgaaact ggagaggtcc tcttttaact tattgagttc aacctttaa
2101  ttttagcttg agtagttcta gtttcccaa acttaagttt atcgacttct
2151  aaaatgtatt tagaattcga gctcggtaca gctttctggg gcaggccagg
2201  cctgaccttg gctttgggc agggagggg ctaaggtgag gcaggtggcg
2251  ccagcaggtg cacacccaat gcccatgagc ccagacactg gacgctgaac
2301  ctcgcggaca gttaagaacc caggggcctc tgcgcctggg cccagctctg
2351  tcccacaccg cggtcacatg gcaccacctc tcttgcagcc tccaccaagg
2401  gcccatcggt cttcccctg gcaccctcct ccaagagcac ctctggggc
2451  acagcggccc tgggctgcct ggtcaaggac tacttccccg aaccggtgac
2501  ggtgtcgtgg aactcaggcg ccctgaccag cggcgtgcac accttcccgg
2551  ctgtcctaca gtcctcagga ctctactccc tcagcagcgt ggtgaccgtg
2601  ccctccagca gcttgggcac ccagacctac atctgcaacg tgaatcacaa
2651  gcccagcaac accaaggtgg acaagaaagt tggtgagagg ccagcacagg
2701  gagggagggt gtctgctgga agccaggctc agcgctcctg cctggacgca
2751  tcccggctat gcagccccag tccagggcag caaggcaggc cccgtctgcc
2801  tcttcacccg gagcctctgc ccgccccact catgctcagg gagagggtct
2851  tctggctttt tcccaggctc tgggcaggca caggctaggt gcccctaacc
2901  caggccctgc acacaaaggg gcaggtgctg ggctcagacc tgccaagagc
2951  catatccggg aggaccctgc ccctgaccta agcccacccc aaaggccaaa
3001  ctctccactc cctcagctcg gacaccttct ctcctcccag attccagtaa
3051  ctcccaatct tctctctgca gagcccaaat cttgtgacaa aactcacaca
3101  tgcccaccgt gcccaggtaa gccagcccag gcctcgccct ccagctcaag
3151  gcgggacagg tgccctagag tagcctgcat ccagggacag gccccagccg
3201  ggtgctgaca cgtccacctc catctcttcc tcagcacctg aactcctggg
3251  gggaccgtca gtcttcctct tccccccaaa acccaaggac accctcatga
3301  tctcccggac ccctgaggtc acatgcgtgg tggtggacgt gagccacgaa
3351  gaccctgagg tcaagttcaa ctggtacgtg gacggcgtgg aggtgcataa
3401  tgccaagaca aagccgcggg aggagcagta caacagcacg taccgtgtgg
3451  tcagcgtcct caccgtcctg caccaggact ggctgaatgg caaggagtac
3501  aagtgcaagg tctccaacaa agccctccca gcccccatcg agaaaaccat
```

```
3551 ctccaaagcc aaaggtggga cccgtggggt gcgagggcca catggacaga 3601 ggccggctcg gcccaccctc tgccctgaga gtgaccgctg taccaacctc 3651 tgtccctaca gggcagcccc gagaaccaca ggtgtacacc ctgcccccat 3701 cccgggatga gctgaccaag aaccaggtca gcctgacctg cctggtcaaa 3751 ggcttctatc ccagcgacat cgccgtggag tgggagagca atgggcagcc 3801 ggagaacaac tacaagacca cgcctcccgt gctggactcc gacggctcct 3851 tcttcctcta cagcaagctc accgtggaca agagcaggtg gcagcagggg 3901 aacgtcttct catgctccgt gatgcatgag gctctgcaca accactacac 3951 gcagaagagc ctctccctgt ccccgggcaa atga
```

The "alternative" protein sequence as shown above as SEQ ID NO: 23 comprises the same coding sequence as the first alternative, however in a slightly different genomic organization, like additional introns and a slightly different "leader sequence"/"signal sequence". Said "leader sequence" may also comprise, as shown above an (additional) intron(s). The person skilled in the art is readily in a position to deduce in the sequence as shown herein the corresponding exon/intron structure by conventional methods.

The exemplified antibody described herein may also comprise a light chain, said light-chain may comprise or have the following amino acid sequence (SEQ ID NO: 8)
DIVLTQSPATLSLSPGERATLSCRASQSVSSSYLAWYQQKPGQAPRLLIY

GASSRATGVPARFSGSGSGTDFTLTISSLEPEDFATYYCLQIYNMPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC which may be encoded by the following nucleic acid sequence:

(SEQ ID NO: 7)
gatatcgtgctgacccagagcccggcgaccctgagcctgtctccgggcga acgtgcgaccctgagctgcagagcgagccagagcgtgagcagcagctatc tggcgtggtaccagcagaaaccaggtcaagcaccgcgtctattaatttat ggcgcgagcagccgtgcaactgggtcccggcgcgttttagcggctctgg atccggcacggattttaccctgaccattagcagcctggaacctgaagact ttgcgacttattattgccttcagatttataatatgcctattacctttggc cagggtacgaaagttgaaattaaacgtacggtggctgcaccatctgtctt catcttcccgccatctgatgagcagttgaaatctggaactgcctctgttg tgtgcctgctgaataacttctatcccagagaggccaaagtacagtggaag gtggataacgccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgttag.

Also the "light chain" of exemplified antibody described herein may comprise a "leader sequence" which is particularly useful in the technical production. A corresponding sequence may be (or may be comprised e.g. in a vector system) the following sequence:

(SEQ ID NO: 27)
atggtgttgcagacccaggtcttcatttctctgttgctctggatctctgg tgcctacggg (followed by) gatatcgtgctgacccagagcccgg cgaccctgagcctgtctccgggcgaacgtgcgaccctgagctgcagagcg agccagagcgtgagcagcagctatctggcgtggtaccagcagaaaccagg tcaagcaccgcgtctattaatttatggcgcgagcagccgtgcaactgggg tcccggcgcgttttagcggctctggatccggcacggattttaccctgacc attagcagcctggaacctgaagactttgcgacttattattgccttcagat ttataatatgcctattacctttggccagggtacgaaagttgaaattaaac gtacggtggctgcaccatctgtcttcatcttcccgccatctgatgagcag ttgaaatctggaactgcctctgttgtgtgcctgctgaataacttctatcc cagagaggccaaagtacagtggaaggtggataacgccctccaatcgggta actcccaggagagtgtcacagagcaggacagcaaggacagcacctacagc ctcagcagcaccctgacgctgagcaaagcagactacgagaaacacaaagt ctacgcctgcgaagtcacccatcagggcctgagctcgcccgtcacaaaga gcttcaacaggggagagtgttag Said sequence encodes the following amino acid sequence (SEQ ID NO: 28)
MVLQTQVFISLLLWISGAYG (followed by) DIVLTQSPATLSLSP

GERATLSCRASQSVSSSYLAWYQQKPGQAPRLLIYGASSRATGVPARFSG

SGSGTDFTLTISSLEPEDFATYYCLQIYNMPITFGQGTKVEIKRTVAAPS

VFIPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

Alternatively, said light chain may also be encoded by a nucleic acid sequence that is optimized for recombinant production as exemplified by the following sequence:

```
  1 atggacatga gggtcctcgc tcagctcctg gggctcctgc tgctctgttt
 51 cccaggtaag gatggagaac actagcagtt tactcagccc agggtgctca
101 gtactgcttt actattcagg gaaattctct tacaacatga ttaattgtgt
151 ggacatttgt ttttatgttt ccaatctcag gcgccagatg t
``` followed by

```
                                                 (SEQ ID NO: 24)
                                                 gatatcgtg
201 ttgacgcagt ctccagccac cctgtctttg tctccagggg aaagagccac
251 cctctcctgc cgggccagtc agagtgttag cagcagctac ttagcctggt
301 accagcagaa acctggccag gcgcccaggc tcctcatcta tggcgcatcc
351 agcagggcca ctggcgtgcc agccaggttc agtggcagtg gtctgggac
401 agacttcact ctcaccatca gcagcctgga gcctgaagat ttcgcgacct
451 attactgtct gcagatttac aacatgccta tcacgttcgg ccaagggacc
501 aaggtggaaa tcaaacgtga gtagaattta aactttgcgg ccgcctagac
551 gtttaagtgg gagatttgga ggggatgagg aatgaaggaa cttcaggata
601 gaaaagggct gaagtcaagt tcagctccta aaatggatgt gggagcaaac
651 tttgaagata aactgaatga cccagaggat gaaacagcgc agatcaaaga
701 ggggcctgga gctctgagaa gagaaggaga ctcatccgtg ttgagtttcc
751 acaagtactg tcttgagttt tgcaataaaa gtgggatagc agagttgagt
801 gagccgtagg ctgagttctc tcttttgtct cctaagtttt tatgactaca
851 aaaatcagta gtatgtcctg aaataatcat taagctgttt gaaagtatga
901 ctgcttgcca tgtagatacc atgtcttgct gaatgatcag aagaggtgtg
951 actcttattc taaaatttgt cacaaaatgt caaaatgaga gactctgtag
1001 gaacgagtcc ttgacagaca gctcaagggg ttttttttcct ttgtctcatt
1051 tctacatgaa agtaaatttg aaatgatctt ttttattata agagtagaaa
1101 tacagttggg tttgaactat atgttttaat ggccacggtt ttgtaagaca
1151 tttggtcctt tgttttccca gttattactc gattgtaatt ttatatcgcc
1201 agcaatggac tgaaacggtc cgcaacctct tctttacaac tgggtgacct
1251 cgcggctgtg ccagccattt ggcgttcacc ctgccgctaa gggccatgtg
1301 aaccccgcg gtagcatccc ttgctccgcg tggaccactt tcctgaggca
1351 cagtgatagg aacagagcca ctaatctgaa gagaacagag atgtgacaga
1401 ctacactaat gtgagaaaaa caaggaaagg gtgacttatt ggagatttca
1451 gaaataaaat gcatttatta ttatattccc ttatttttaat tttctattag
1501 ggaattagaa agggcataaa ctgctttatc cagtgttata ttaaaagctt
1551 aatgtatata atcttttaga ggtaaaatct acagccagca aaagtcatgg
1601 taaatattct ttgactgaac tctcactaaa ctcctctaaa ttatatgtca
1651 tattaactgg ttaaattaat ataaatttgt gacatgacct taactggtta
1701 ggtaggatat ttttcttcat gcaaaaatat gactaataat aatttagcac
1751 aaaaatattt cccaatactt taattctgtg atagaaaaat gtttaactca
1801 gctactataa tcccataatt ttgaaaacta tttattagct tttgtgtttg
```

```
                              -continued
1851  acccttccct  agccaaaggc  aactatttaa  ggacccttta  aaactcttga 1901  aactacttta  gagtcattaa  gttatttaac  cacttttaat  tactttaaaa 1951  tgatgtcaat  tcccttttaa  ctattaattt  attttaaggg  gggaaaggct 2001  gctcataatt  ctattgtttt  tcttggtaaa  gaactctcag  ttttcgtttt 2051  tactacctct  gtcacccaag  agttggcatc  tcaacagagg  ggactttccg 2101  agaggccatc  tggcagttgc  ttaagatcag  aagtgaagtc  tgccagttcc 2151  tcccaggcag  gtggcccaga  ttacagttga  cctgttctgg  tgtggctaaa 2201  aattgtccca  tgtggttaca  aaccattaga  ccagggtctg  atgaattgct 2251  cagaatattt  ctggacaccc  aaatacagac  cctggcttaa  ggccctgtcc 2301  atacagtagg  tttagcttgg  ctacaccaaa  ggaagccata  cagaggctaa 2351  tatcagagta  ttcttggaag  agacaggaga  aaatgaaagc  cagtttctgc 2401  tcttacctta  tgtgcttgtg  ttcagactcc  caaacatcag  gagtgtcaga 2451  taaactggtc  tgaatctctg  tctgaagcat  ggaactgaaa  agaatgtagt 2501  ttcagggaag  aaaggcaata  gaaggaagcc  tgagaatacg  gatcaattct 2551  aaactctgag  ggggtcggat  gacgtggcca  ttctttgcct  aaagcattga 2601  gtttactgca  aggtcagaaa  agcatgcaaa  gccctcagaa  tggctgcaaa 2651  gagctccaac  aaaacaattt  agaactttat  taaggaatag  ggggaagcta 2701  ggaagaaact  caaaacatca  agattttaaa  tacgcttctt  ggtctccttg 2751  ctataattat  ctgggataag  catgctgttt  tctgtctgtc  cctaacatgc 2801  cctgtgatta  tccgcaaaca  acacacccaa  gggcagaact  ttgttactta 2851  aacaccatcc  tgtttgcttc  tttcctcagg  aactgtggct  gcaccatctg 2901  tcttcatctt  cccgccatct  gatgagcagt  tgaaatctgg  aactgcctct 2951  gttgtgtgcc  tgctgaataa  cttctatccc  agagaggcca  aagtacagtg 3001  gaaggtggat  aacgccctcc  aatcgggtaa  ctcccaggag  agtgtcacag 3051  agcaggacag  caaggacagc  acctacagcc  tcagcagcac  cctgacgctg 3101  agcaaagcag  actacgagaa  acacaaagtc  tacgcctgcg  aagtcaccca 3151  tcagggcctg  agctcgcccg  tcacaaagag  cttcaacagg  ggagagtgtt 3201  ag
```

The above "sequence" for an exemplified light chain has also a slightly different genomic structure. This "alternative sequence" comprises different and/or additional introns. Accordingly the embodiments describing for the "heavy chain" apply here mutatis mutandis.

In context of the present invention, the term "antibody molecule" relates to full immunoglobulin molecules, e.g. IgMs, IgDs, IgEs, IgAs or IgGs, like IgG1, IgG2, IgG2b, IgG3 or IgG4 as well as to parts of such immunoglobulin molecules, like Fab-fragments, Fab'-fragments, F(ab)$_2$-fragments, chimeric F(ab)$_2$ or chimeric Fab' fragments, chimeric Fab-fragments or isolated V$_H$- or CDR-regions (said isolated V$_H$- or CDR-regions being, e.g. to be integrated or engineered in corresponding "framework(s)") Also comprised in the term "antibody molecule" are diabodies and molecules that comprise an antibody Fc domain as a vehicle attached to at least one antigen binding moiety/peptide, e.g. peptibodies as described in WO 00/24782. Accordingly, and in context of this invention, the term "variable region of the heavy chain (V$_H$)" is not limited to a variable region in a full immunoglobulin but also relates to the corresponding parts of said variable region of the heavy chain (V$_H$), like the CDRs, either alone or in combination of the CDR1, 2, and/or 3 or the corresponding "framework" of the variable region. Therefore, an antibody molecule of the present invention may also be an antibody construct which comprises, as antigen binding site, the CDRs or at least one CDR of a given variable region of the glycosylated heavy chain (V$_H$). Said corresponding part of said variable region of the heavy chain (V$_H$) in the antibody construct of the invention is glycosylated as defined herein, e.g. comprises a glycosylated asparagine (Asn) in the antigen binding site. An example of such an "isolated part" a variable region of the heavy chain (V$_H$) is the herein exemplified CDR2 region comprised in SEQ ID NO: 12 (or encoded by a nucleic acid sequence as shown in SEQ ID NO: 11).

Furthermore, the term "antibody molecule" relates to modified and/or altered antibody molecules, like chimeric, humanized or fully humanized antibodies.

Said "fully humanized antibody" molecules are also characterized and described as "completely human" antibodies.

All these antibodies can be generated by methods known in the art. For example, by phage display technology, recombinant antibody molecules may be generated due to the use of in vitro maturation which is the usage of a complete human immunoglobulin γ, subclass-1 framework (IgG1) as described by Knappik (2000) J Mol. Biol. 296(1), 57-86. and Rauchenberger (2003) J Biol. Chem. 278(40), 38194-205.

As documented in the appended examples, the term antibody, relates, e.g. to an IgG molecule and e.g. to an IgG1. The term also relates to modified or altered monoclonal or polyclonal antibodies as well as to recombinantly or synthetically generated/synthesized antibodies. The term also relates to intact antibodies as well as to antibody fragments/parts thereof, like, separated light and heavy chains, Fab, Fab/c, Fv, Fab', F(ab')$_2$. The term "antibody molecule" also comprises antibody derivatives, the bifunctional antibodies and antibody constructs, like single chain Fvs (scFv) or antibody-fusion proteins. Also envisaged are catalytic and/or proteolytic antibodies which comprise a glycosylated $V_H$ domain, e.g. a glycosylated $V_H$-CDR as defined herein. The term "antibody molecule" relates also to recombinantly produced antibody molecules/antibody constructs which may comprise, besides one specificity (e.g. against Aβ/Aβ), another or a further specificity. Such constructs may comprise, but a not limited to "bi-specific" or "tri-specific" constructs. Further details on the term "antibody molecule" of the invention are provided herein below.

As pointed out above, also envisaged are a single-chain antibody, a chimeric antibody, a CDR-grafted antibody, a bivalent antibody-construct, an antibody-fusion protein, a cross-cloned antibody or a synthetic antibody comprising the herein defined glycosylation in at least one antigen binding site, e.g. in at least one variable region of a/the heavy chain defined herein and being glycosylated. When for example single-chain antibodies are produced, the herein defined "variable region of the heavy chain" is not limited to a heavy chain per se, but is meant to also relate to the corresponding parts derived from a heavy chain of a full antibody, e.g. a full immunoglobulin, like an IgG. Such parts may be the corresponding CDRs either alone or with parts of their corresponding framework. Furthermore, genetic variants of immunoglobulin genes are also envisaged in context of this invention. Genetic variants of, e.g., immunoglobulin heavy G chain subclass 1 (IgG1) may comprise the G1m(17) or G1m(3) allotypic markers in the CH1 domain, or the (G1m(1) or the G1m(non-1) allotypic marker in the CH3 domain. Here, preferably an IgG1 of the Gm(17)(z) and Gm(1)(a) allotype is employed. The antibody molecule of the invention also comprises modified or mutant antibodies, like mutant IgG with enhanced or attenuated Fc-receptor binding or complement activation. In one embodiment, the antibody provided in accordance with this invention is a fully-humanized antibody or "completely human" antibody.

Accordingly, the antibodies of the invention may also comprise cross-cloned antibodies, i.e. antibodies comprising different antibody regions (e.g. CDR-regions) from one or more parental or affinity-optimized antibody(ies) as described herein. These cross-cloned antibodies may be antibodies in several, different frameworks, e.g. an IgG-framework, e.g. a (human) IgG1-, IgG2a or an IgG2b-framework. For example, said antibody framework is a mammalian, e.g. a human framework. The domains on the light and heavy chains have the same general structure and each domain comprises four framework regions, whose sequences are relatively conserved, joined by three hypervariable domains known as complementarity determining regions (CDR1-3).

As used herein, a "human framework region" relates to a framework region that is substantially identical (about 85% or more, usually 90-95% or more) to the framework region of a naturally occurring human immunoglobulin. The framework region of an antibody (e.g. the combined framework regions of the constituent light and heavy chains) serves to position and align the CDR's. The CDR's are primarily responsible for binding to an epitope of an antigen. It is of note that not only cross-cloned antibodies described herein may be presented in a preferred (human) antibody framework, but also antibody molecules comprising CDRs from antibodies as described herein, may be introduced in an immunoglobulin framework. Examples for frameworks include IgG1, IgG2a and IgG2b. Most preferred are human frameworks and human IgG1 frameworks, such as the heavy chain of an ANTIBODY as shown in, inter alia, SEQ ID NO: 6.

In one embodiment ANTIBODY isoforms may comprise in the variable heavy chain region a CDR1 comprising the following amino acids:

```
GFTFSSYAMS          (SEQ ID NO: 10)
```

Said CDR1 may be encoded by the following nucleic acid sequence:

```
ggatttacctttagcagctatgcgatgagc    (SEQ ID NO: 9)
```

ANTIBODY isoforms may comprise the following CDR2 in the variable region of the heavy chain:

```
AINASGTRTYYADSVKG       (SEQ ID NO: 12)
```

(N: N-linked glycosylation site at Asn-52 of a Full Heavy Chain)

Said CDR2 may be encoded by the following nucleic acid sequence:

```
                                  (SEQ ID NO: 11)
gctattaatgcttctggtactcgtacttattatgctgattctgttaagg
gt
```

The N-glycosylation in accordance with this invention is e.g. comprised in said CDR2 region and is located on the corresponding Asn52 of the variable region of the heavy chain, said variable region ($V_H$) being encoded by a nucleic acid molecule as shown in SEQ ID NO: 1 and having an amino acid sequence as shown in SEQ ID NO: 2.

Furthermore, ANTIBODY isoforms may comprise in their variable heavy chain region a CDR3 comprising the following amino acid sequence:

```
GKGNTHKPYGYVRYFDV       (SEQ ID NO: 14)
```

Said CDR3 may be encoded by the following nucleic acid sequence:

```
                                  (SEQ ID NO: 13)
ggtaagggtaatactcataagccttatggttatgttcgttattttgatgtt
```

ANTIBODY isoforms may comprise a light (L) chain which may be characterized by the following CDRs:

```
CDR1:
                                    (SEQ ID NO: 16)
RASQSVSSSYLA (SEQ ID NO: 15)
agagcgagccagagcgtgagcagcagctatctggcg

CDR2:
                                    (SEQ ID NO: 18)
GASSRAT (SEQ ID NO: 17)
ggcgcgagcagccgtgcaact

CDR3:
                                    (SEQ ID NO: 20)
LQIYNMPI (SEQ ID NO: 19)
cttcagatttataatatgcctatt
```

ANTIBODY isoforms may comprise additional potential glycosylation sites (as known in the art comprising the Asn-X-Ser/Thr motives) in the amino acid sequence of the heavy chains of the antibody, e.g. in the well conserved glycosylation site at Asn 306 in the non-variable Fc-part (corresponding to "Asn297" in the Kabat-system (Kabat (1991) Sequences of Proteins of Immunological Interest, 5th ed., Bethesda, Md.: National Center for Biotechnology Information, National Library of Medicine), said heavy chains being or comprising the sequence as provided above, namely in SEQ ID NO: 6 (as encoded by SEQ ID NO: 5).

In one embodiment of the present invention, the ANTIBODY isoforms are characterized in that at least one antigen binding site comprises a glycosylated asparagine (Asn) in the variable region of the heavy chain ($V_H$), said $V_H$ being encoded by (a) a nucleic acid molecule comprising the nucleotide sequence as shown in SEQ ID NO: 1:

```
                                              (SEQ ID NO: 1)
CAGGTGGAATTGGTGGAAAGCGGCGGCGGCCTGGTGCAACCGGGCGGCAG

CCTGCGTCTGAGCTGCGCGGCCTCCGGATTTACCTTTAGCAGCTATGCGA

TGAGCTGGGTGCGCCAAGCCCCTGGGAAGGGTCTCGAGTGGGTGAGCGCT

ATTAATGCTTCTGGTACTCGTACTTATTATGCTGATTCTGTTAAGGGTCG

TTTTACCATTTCACGTGATAATTCGAAAAACACCCTGTATCTGCAAATGA

ACAGCCTGCGTGCGGAAGATACGGCCGTGTATTATTGCGCGCGTGGTAAG

GGTAATACTCATAAGCCTTATGGTTATGTTCGTTATTTTGATGTTTGGGG

CCAAGGCACCCTGGTGACGGTTAGCTCA;
```

(b) a nucleic acid molecule which encodes a polypeptide having the amino acid sequence as shown in SEQ ID NO: 2:

```
QVELVESGGGLVQPGGSLRLSCAASGFTFSSYAMSWVRQAPGKGLEWVSA

INASGTRTYYADSVKGRFTISRDNSKNTLYLQMNSLRAEDTAVYYCARGK

GNTHKPYGYVRYFDVWGQGTLVTVSS (SEQ ID NO: 2; "N" in bold representing the herein
defined Asn on position 52 of the variable region
of the heavy chain);
```

(c) a nucleic acid molecule that hybridizes to the nucleic acid molecule of (a) or (b) and which encodes a polypeptide which is capable of binding to the β-A4 peptide/Aβ4 as shown in the following amino acid sequence

```
                                              (SEQ ID NO: 3)
DAEFRHDSGYEVHHQKLVFFAEDVGSNKGAIIGLMVGGVVIA
``` or a fragment thereof which comprises at least 15 amino acids;

(d) a nucleic acid molecule that hybridizes to the nucleic acid molecule of (a) or (b) and which encodes a polypeptide which is capable of binding to at least two regions on the β-A4 peptide/Aβ4 as shown in the following amino acid sequence

```
                                              (SEQ ID NO: 3)
DAEFRHDSGYEVHHQKLVFFAEDVGSNKGAIIGLMVGGVVIA
``` or to at least two regions of a fragment of SEQ ID NO. 3 which comprises at least 15 amino acids whereby said two regions on the β-A4 peptide Aβ4 or said fragment thereof comprise the amino acids on position 3 to 6 and on position 18 to 26 of SEQ ID No. 3; or (e) a nucleic acid sequence that is degenerate to a nucleic acid sequence as defined in any one of (a) to (d).

The person skilled in the art is aware of the fact that the term "nucleic acid molecule that hybridizes to the nucleic acid molecule of (a) or (b) and which encodes a polypeptide which is capable of binding to at least two regions on the β-A4 peptide/Aβ4" as employed herein relates to a coding strand of a double stranded nucleic acid molecule whereby the non-coding strand hybridizes to the above identified nucleic acid molecule of (a) and (b).

As pointed out above, the purified antibody molecule comprising the herein defined Asn-glycosylation may, inter alia, be characterized and described as an antibody molecule wherein the variable region comprising a glycosylated Asn is comprised in a heavy chain selected from the group consisting of:

(a) a heavy chain polypeptide encoded by a nucleic acid molecule as shown in SEQ ID NOS: 5, 23 or 25;

(b) a heavy chain polypeptide having the amino acid sequence as shown in SEQ ID NO: 6 or 26;

(c) a heavy chain polypeptide encoded by a nucleic acid molecule that hybridizes to the nucleic acid molecule of (a) and which encodes a polypeptide which is capable of binding to the β-A4 peptide/Aβ4 as shown in the following amino acid sequence

```
                                              (SEQ ID NO: 3)
DAEFRHDSGYEVHHQKLVFFAEDVGSNKGAIIGLMVGGVVIA
``` or a fragment thereof which comprises at least 15 amino acids; or (d) a heavy chain polypeptide encoded by a nucleic acid molecule that hybridizes to the nucleic acid molecule of (a) and which encodes a polypeptide which is capable of binding to at least two regions on the β-A4 peptide/Aβ4 as shown in the following amino acid sequence

```
                                              (SEQ ID NO:3)
DAEFRHDSGYEVHHQKLVFFAEDVGSNKGAIIGLMVGGVVIA
``` or to at least two regions of a fragment of SEQ ID NO. 3 which comprises at least 15 amino acids whereby said two regions on the β-A4 peptide Aβ4 or said fragment thereof comprise the amino acids on position 3 to 6 and on position 18 to 26.

The above-identified antibody (e.g. an exemplified antibody of the invention) may also comprise an L-chain with the following amino acid sequence:

(SEQ ID NO: 22)
DIVLTQSPATLSLSPGERATLSCRASQSVSSSYLAWYQQKPGQAPRLLIY

GASSRATGVPARFSGSGSGTDFTLTISSLEPEDFATYYCLQIYNMPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC or an L-chain as, e.g. encoded by the following nucleic acid sequence:

(SEQ ID NO: 21)
gatatcgtgctgacccagagcccggcgaccctgagcctgtctccgggcga acgtgcgaccctgagctgcagagcgagccagagcgtgagcagcagctatc tggcgtggtaccagcagaaaccaggtcaagcaccgcgtctattaatttat ggcgcgagcagccgtgcaactggggtcccggcgcgttttagcggctctgg atccggcacggatttaccctgaccattagcagcctggaacctgaagact ttgcgacttattattgccttcagatttataatatgcctattacctttggc cagggtacgaaagttgaaattaaacgtacggtggctgcaccatctgtctt catcttccgccatctgatgagcagttgaaatctggaactgcctctgttg tgtgcctgctgaataacttctatcccagagaggccaaagtacagtggaag gtggataacgccctccaatcgggtaactccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacagggagagtgttag As printed out above, the purified antibody molecule comprising the herein defined Asn-glycosylation in the heavy chain may further comprise a light chain selected from the group consisting of:
(a) a light chain polypeptide encoded by a nucleic acid molecule as shown in SEQ ID NOS: 7, 21, 24 or 27;
(b) a light chain polypeptide having the amino acid sequence as shown in SEQ ID NO: 8, 22 or 28;
(c) a light chain polypeptide encoded by a nucleic acid molecule that hybridizes to the nucleic acid molecule of (a) and which encodes a polypeptide which is capable of binding to the β-A4 peptide/Aβ4 as shown in the following amino acid sequence (SEQ ID NO: 3)
DAEFRHDSGYEVHHQKLVFEAEDVGSNKGAIIGLMVGGVVIA or a fragment thereof which comprises at least 15 amino acids; or
(d) a light chain polypeptide encoded by a nucleic acid molecule that hybridizes to the nucleic acid molecule of (a) and which encodes a polypeptide which is capable of binding to at least two regions on the β-A4 peptide/Aβ4 as shown in the following amino acid sequence (SEQ ID NO: 3)
DAEFRHDSGYEVHHQKLVFFAEDVGSNKGAIIGLMVGGVVLA or to at least two regions of a fragment of SEQ ID NO. 3 which comprises at least 15 amino acids The term "hybridization" or "hybridizes" as used herein in context of nucleic acid molecules/DNA sequences may relate to hybridizations under stringent or non-stringent conditions. If not further specified, the conditions are preferably non-stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Such fragments may represent nucleic acid sequences which code for a non-functional antibody molecule or a non-functional fragment thereof or for a CDR as defined herein, and which have a length of at least 12 nucleotides, preferably at least 15, more preferably at least 18, more preferably of at least 21 nucleotides, more preferably at least 30 nucleotides, even more preferably at least 40 nucleotides and most preferably at least 60 nucleotides. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

The term "hybridizing sequences" preferably refers to sequences which display a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity with a nucleic acid sequence as described above encoding an antibody molecule. Moreover, the term "hybridizing sequences" preferably refers to sequences encoding an antibody molecule having a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity with an amino acid sequence of the antibody molecule as described herein above.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, Nucl. Acids Res. 25 (1997), 3389-3402; Altschul, J. Mol. Evol. 36 (1993), 290-300; Altschul, J. Mol. Biol. 215 (1990), 403-410). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands.

Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid.

In order to determine whether an amino acid residue or nucleotide residue in a given antibody sequence corresponds to a certain position in the amino acid sequence or nucleotide sequence of any of e.g. SEQ ID NOS: 1, 5, 23 and 25, the skilled person can use means and methods well-known in the art, e.g., alignments, either manually or by using computer programs such as those mentioned further down below in connection with the definition of the term "hybridization" and degrees of homology.

For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules. Another example for a program capable of generating sequence alignments is the CLUSTALW computer program (Thompson, Nucl. Acids Res. 2 (1994), 4673-4680) or FASTDB (Brutlag Comp. App. Biosci. 6 (1990), 237-245), as known in the art.

In one embodiment the present invention provides glycosylated ANTIBODY isoforms wherein the glycosylation on Asn in the $V_H$ region is selected from the group consisting of
(a) a sugar structure of the biantennary complex type without core fucosylation;
(b) a sugar structures of the biantennary hybrid type;
(c) a sugar structures of the biantennary oligomannose type; and
(d) a bi-antennary structure of any of the structures as provided in appended FIG. 5 or appended FIG. 27.

The corresponding sugar structure does, in one embodiment of the antibody/antibodies of this invention not comprise a core fucosylation.

The corresponding N-glycosylation may predominantly consist of sugar structures of the biantennary complex type (≥75%; mainly 80-90%) without core fucosylation and highly sialidated with up to 80% of antennae. Minor sugar structures belong to the biantennary hybrid and the oligomannose type (≤25%), respectively and are also shown in appended FIGS. 5 and 27. The glycosylation structures in the variable region are resistant to cleavage by N-glycosidase F from the protein (amino acid polypeptide).

In one embodiment the dominant complex biantennary sugar structures are further characterized
- by containing one or two sialic acids attached to either the one or the other antenna or to both antennae. The sialic acid is of the N-acetyl neuraminic acid type and is most likely bound in alpha 2,3 linkage to the terminal beta 1,4 linked galactoses.
- by lacking core fucosylation, i.e. lacking the fucose residue attached in alpha 1,6 linkage to the innermost N-acetyl-glucosamine at the reducing end of the sugar chain.

In one embodiment the hybrid sugar structures are further characterized
- by containing a complex type antenna (a lactosaminyl unit (GlcNAc-Gal) attached to the core sugar structure) as one arm of the bi-antennary structure. This arm predominantly contains N-acetyl neuraminic acid attached to the terminal beta 1,4 linked galactose.
- by having one up to 3 additional mannose subunits attached to the core sugar structure as the other antenna.
- by lacking core fucosylation, i.e. lacking the fucose residue attached in alpha 1,6 linkage to the innermost N-acetyl-glucosamine at the reducing end of the sugar chain.

In one embodiment the oligomannose type sugar structures are further characterized
- by containing 4 (Man4→GlcNAc2), 5 (Man5→GlcNAc2) or 6 (Man6→GlcNAc2) mannose subunits in the complete sugar structure, i.e. including the 3 branching mannose subunits present in a typical N-linked core sugar structure.
- by lacking core fucosylation, i.e. lacking the fucose residue attached in alpha 1→6 linkage to the innermost N-acetyl-glucosamine at the reducing end of the sugar chain.

In another embodiment of the present invention, a composition is provided which comprises an antibody molecule being characterized in that one antigen binding site comprises a glycosylated asparagine (Asn) in the variable region of the heavy chain ($V_H$) and an antibody molecule being characterized in that two antigen binding sites comprise a glycosylated asparagine (Asn) in the variable region of the heavy chain ($V_H$), i.e. a composition comprising mono-glycosylated ANTIBODY and double-glycosylated ANTIBODY, and is hereinafter referred to as ANTIBODY COMPOSITION. The term ANTIBODY COMPOSITION also relates to compositions which comprise molecules comprising at least one glycosylated $V_H$ region as defined herein or at least one glycosylated CDR of said $V_H$ region, whereby said molecules may, inter alia be immunoglobulins or immunoglobulin isoforms and modifications as described above. For example said composition may also comprise single chain antibodies (scFvs) or bispecific molecules comprising glycosylated, $V_H$-derived CDR regions.

Further definitions of the ANTIBODY COMPOSITION of this invention are provided below.

The ANTIBODY COMPOSITION does not or does merely to a very low extent comprise "in $V_H$ non-glycosylated" antibody molecules, i.e. antibodies that do not comprise the herein defined glycosylation in the variable region, in particular the variable part of the heavy chain ($V_H$).

In context of this invention and in particular in context of the antibody mixtures provided herein, the term "does not or does merely to a very low extent comprise non-glycosylated antibody molecules" means that the ANTIBODY COMPOSITION comprises less than 10%, e.g. less than 5%, for example less than 4%, for example less than 3%, for example less than 2%, for example less than 1%, for example less than 0.5 or less of the/a non-glycosylated isoform as described herein.

Accordingly, in one embodiment, the present invention provides for an antibody preparation comprising mono-glycosylated and/or double-glycosylated antibodies (said glycosylation being located in the variable region of the heavy chain) and being devoid of antibody molecules without glycosylation in the variable region.

Again, the term "devoid of antibody molecules without glycosylation in the variable region" relates to antibody preparations/antibody mixtures/antibody pools which comprise at the most 10%, e.g. at the most 5%, e.g. at the most 4%, e.g. at the most 3%, e.g. at the most 2%, e.g. at the most 1%, e.g. at the most 0.5%, e.g. at the most 4%, e.g. at the most 3%, e.g. at the most 2%, e.g. at the most 1%, e.g. at the most 0.5%, e.g. at the most 0.3%, e.g. at the most 0.2% non-glycosylated isoforms as described herein.

In one embodiment the present invention provides a composition which does not comprise more than 0.5% antibody isoforms which are non-glycosylated in their variable regions, e.g. are non-glycosylated in the variable region of the heavy chain.

As pointed out above, in one embodiment of the present invention, a mixture of mono- and double-glycosylated antibodies, e.g. immunoglobulins, is provided, said mixture being devoid of antibody molecules without glycosylation in the variable region. Antibodies devoid of such a post-translational modification in the variable region, e.g. in both variable regions of the heavy chain (both ($V_H$)-regions) is, in context of this invention considered as an "non-glycosylated form", comprising no glycosylation in the variable region of the heavy chain. Yet, this "non-glycosylated form" may nevertheless comprise (a) glycosylation(s) in the constant region (C-region) of the antibody, for example, and most commonly at the well conserved glycosylation site of the Fc-part, in particular the asparagine (Asn) 306 in the non-variable/constant Fc-part as defined herein.

The glycosylated ANTIBODY isoforms on their own or as a combination of mono-glycosylated and double-glycosylated isoforms are very useful and advantageous therapeutic antibody preparations for the treatment of Alzheimer Disease (AD), and other amyloid related disorders like Down's syndrome, Hereditary cerebral hemorrhage with amyloidosis Dutch type, Parkinson's disease, ALS (amyotrophic lateral sclerosis), Creutzfeld Jacob disease, HIV-related dementia and motor neuropathy. The glycosylated ANTIBODY isoforms on their own or as a combination of mono-glycosylated and double-glycosylated isoforms are also unique diagnostic tools.

Both glycosylated isoforms as described herein show improved and highly effective brain penetration in vivo. Effective brain penetration and specific binding to amyloid-β plaques can be demonstrated in PS2APP mice, a mouse model for AD-related amyloidosis.

Furthermore, improved specificity for genuine human amyloid-β plaques by immunohistochemical stainings in vitro with significantly reduced unspecific stickiness could be detected. The minimal effective concentration for consistent staining of human amyloid-β plaques was determined to be 10 ng/ml, as documented in the appended examples.

As documented in the appended examples, the separation and characterization of differently glycosylated antibodies, e.g. immunoglobulins revealed that the glycosylation of the variable region of the heavy chain has a surprising influence on the antigen binding to Aβ peptides, the diagnostic value, the pharmacological profile and functional activity. The purified antibody molecules may be submitted to MS-analytics, binding studies (Biacore) and epitope mapping (Pepspot analysis) binding to soluble Aβ, dissociation of aggregated Aβ and microscopical analysis of binding to β-amyloid plaques in vivo and in vitro.

In one embodiment of the present invention, the purified ANTIBODY or the ANTIBODY COMPOSITION is capable of specifically recognizing the β-A4 peptide/Aβ4.

Accordingly, and as described herein, purified ANTIBODY or ANTIBODY COMPOSITION relates in a specific embodiment to ANTIBODY or ANTIBODY COMPOSITION capable of specifically recognizing two regions (the N-terminal region and the central/middle part) of Aβ/Aβ4.

The term "specifically recognizing" means in accordance with this invention that the antibody molecule is capable of specifically interacting with and/or binding to at least two amino acids of each of the two regions of β-A4 as defined herein. Said term relates to the specificity of the antibody molecule, i.e. to its ability to discriminate between the specific regions of the β-A4 peptide as defined herein and another, not related region of the β-A4 peptide or another, not APP-related protein/peptide/(unrelated) tests-peptide. Accordingly, specificity can be determined experimentally by methods known in the art and methods as disclosed and described herein. Such methods comprise, but are not limited to Western blots, ELISA-, RIA-, ECL-, IRMA-tests and peptide scans. Such methods also comprise the determination of $K_D$-values as, inter alia, illustrated in the appended examples. The peptide scan (pepspot assay) is routinely employed to map linear epitopes in a polypeptide antigen. The primary sequence of the polypeptide is synthesized successively on activated cellulose with peptides overlapping one another. The recognition of certain peptides by the antibody to be tested for its ability to detect or recognize a specific antigen/epitope is scored by routine colour development (secondary antibody with an enzyme or a dye, like horseradish peroxidase or 4-chloronaphthol or hydrogenperoxide), by a chemoluminescence reaction or similar means known in the art. In the case of, inter alia, chemoluminescence reactions or the use of a secondary fluorescent antibody, the reaction can be quantified. If the antibody reacts with a certain set of overlapping peptides one can deduce the minimum sequence of amino acids that is necessary for reaction; see illustrative examples provided in accordance with this invention.

The same assay can reveal two distant clusters of reactive peptides, which indicate the recognition of a discontinuous, i.e. conformational epitope in the antigenic polypeptide (Geysen (1986), Mol. Immunol. 23, 709-715).

In addition to the pepspot assay, standard ELISA assay can be carried out. As demonstrated in the appended examples small hexapeptides may be coupled to a protein and coated to an immunoplate and reacted with antibodies to be tested. The scoring may be carried out by standard colour development (e.g. secondary antibody with horseradish peroxidase and tetramethyl benzidine with hydrogenperoxide). The reaction in certain wells is scored by the optical density, for example at 450 nm. Typical background (=negative reaction) may be 0.1 OD, typical positive reaction may be 1 OD. This means the difference (ratio) positive/negative can be more than 10 fold. Further details are given in the appended examples. Additional, quantitative methods for determining the specificity and the ability of "specifically recognizing" the herein defined two regions of the β-A4 peptide are given herein below.

The term "two regions of the β-A4 peptide" relates to two regions relating e.g. to the N-terminal amino acids 3 to 6 and a central/middle epitope on position amino acids 18 to 24 of SEQ ID No. 3 (the β-A4 peptide). As documented in the appended examples, in particular the double-glycosylated ANTIBODY A isoform provided and exemplified herein (see appended examples) detects two parts of the Aβ molecule, the first part comprising amino acid 1 to 10 in the N-terminus and the second part comprising amino acids 17 to 26 of the central/middle part of Aβ (as shown in SEQ ID No. 3). Accordingly, in the antibody mixtures provided herein and comprising the mono- as well as the double-glycosylated isoforms of the antibodies as provided herein, the two regions may also somewhat broadened, then comprising, e.g. amino acids 1 to 10 (or to 11 or to 12) or a shorter part thereof and amino acids 17 to 26 (or amino acids 16 to 27) or a shorter part comprised between amino acids 17 to 26, like e.g. amino acids 19 to 26 or 20 to 26). The term "β-A4 peptide" in context of this invention relates to the herein above described Aβ39, Aβ41, Aβ43, in particular to Aβ40 and Aβ42. Aβ42 is also depicted in appended SEQ ID NO: 3. It is of note that the term "two regions of the β-A4 peptide" also relates to an "epitope" and/or an "antigenic determinant" which comprises the herein defined two regions of the β-A4 peptide or parts thereof. In accordance with this invention, said two regions of the β-A4 peptide are separated (on the level of the amino acid sequence) in the primary structure of the β-A4 peptide by at least one amino acid, e.g. by at least two amino acids, e.g. by at least three amino acids, e.g. by at least four amino acids, e.g. by at least five amino acids, e.g. by at least six amino acids. As shown herein and as documented in the appended examples, the inventive antibodies/antibody molecules detect/interact with and/or bind to two regions of the β-A4 peptide as defined herein, whereby said two regions are separated (on the primary structure level of the amino acid sequence) by at least one amino acid and wherein the sequence separating said two regions/"epitope" may comprise more then seven, amino acids, more than 8 amino acids, more than 10 amino acids or even about 14 amino acids.

The term "two regions of the β-A4 peptide" may also relate to a conformational epitope or a discontinuous epitope consisting of said two regions or parts thereof; see also Geysen (1986), loc. cit. In context of this invention, a conformational epitope is defined by two or more discrete amino acid sequences separated in the primary sequence which come together on the surface when the polypeptide folds to the native protein (Sela, (1969) Science 166, 1365 and Layer, (1990) Cell 61, 553-6). The antibody molecules of the present invention are envisaged to specifically bind to/interact with a conformational epitope(s) composed of and/or comprising the two regions of β-A4 described herein or parts thereof as disclosed herein below. The "antibody molecules" of the present invention are thought to comprise a simultaneous and independent dual specificity to (a) an amino acid stretch comprising amino acids 1 to 11 (or (a) part(s) thereof) of β-A4 and (b) an amino acid stretch comprising amino acids 16 to 27 (or (a) part(s) thereof) of β-A4 (SEQ ID NO. 3). Fragments or parts of these stretches comprise at least two, in most cases at least three amino acids.

Antibody molecules, e.g. immunoglobulins could, inter alia, be expressed in three systems: a) in transiently transfected human embryonic kidney cells containing the Epstein barr virus nuclear antigen (HEK 293 EBNA, Invitrogen), b) in transiently transfected Chinese hamster ovary cells (CHO), and c) in stably transfected CHO cell lines (CHO K1 and CHO K1 SV, Lonza Biologics). The three different antibody molecules (non-, mono or double-glycosylated) may be separated by specific purification steps, comprising protein A purification, cation exchange chromatography as well as size column separation as detailed below.

In one embodiment of the invention, the antibody molecule is recombinantly produced, e.g. in a CHO-cell or in a HEK 293 cell, preferably CHO-cells. In a particular embodiment the above identified glycosylation patterns may be obtained after expression in CHO-cells. CHO-cells are very well known in the art and comprise, inter alia, the CHO-cells as employed in the experimental part, like CHO K1 or CHO K1 SV cells. Commonly used HEK 293 cells are HEK 293 EBNA.

The recombinant expression of the glycosylated, inventive antibody is carried out, as shown in the examples in a eukaryotic expression system in particular in CHO-cells. However, further expression cells, i.e. eukaryotic cells may be envisaged. Eukaryotic cells comprise, for example, fungal or animal cells. Examples for suitable fungal cells are yeast cells, e.g. those of the genus *Saccharomyces*, e.g. those of the species *Saccharomyces cerevisiae*. Suitable animal cells are, for instance, insect cells, vertebrate cells, e.g. mammalian cells, such as e.g. NSO, MDCK, U2-OSHela, NIH3T3, MOLT-4, Jurkat, PC-12, PC-3, IMR, NT2N, Sk-n-sh, CaSki, C33A. Also human cell lines are envisaged. These host cells, e.g. CHO-cells, provide post-translational modifications to the antibody molecules of the invention, including leader peptide or signal sequence removal, folding and assembly of H (heavy) and L (light) chains and most importantly glycosylation of the molecule at correct sides, namely in the variable region of the heavy chain. Such signal peptide or leader sequence is proteolytically cleaved by the host signal peptidase during the secretory pathway during its recombinant production e.g. in CHO cells. Further suitable cell lines known in the art are obtainable from cell line depositories, like the American Type Culture Collection (ATCC). In accordance with the present invention, it is furthermore envisaged that primary cells/cell cultures may function as host cells. Said cells are in particular derived from insects (like insects of the species *Drosophila* or *Blatta*) or mammals (like human, swine, mouse or rat). Said host cells may also comprise cells from and/or derived from cell lines like neuroblastoma cell lines.

Accordingly, the antibody molecule of the invention is prepared using a recombinant expression system. An example for such system, as pointed out above, is a mammalian expression system using Chinese hamster ovary (CHO) cells. These may be used with the glutamine synthetase (GS) system (WO 87/04462; WO 89/01036; Bebbington, 1992, Biotechnology (NY), 10, 169-75). This system involves the transfection of a CHO cell with a gene encoding the GS enzyme and the desired antibody genes. CHO cells are then selected which grow in glutamine free media and are also subjected to inhibition of the GS enzyme using methionine sulphoximine (MSX). In order to survive, the cells will amplify the GS enzyme expression and concomitantly the expression of the mAb.

Another possible expression system is the CHO dhfr− system, where the CHO cells are deficient for dihydrofolate reductase (dhfr−) and dependent on thymidine and hypoxanthine for growth. The parenteral CHO dhfr− cell line is transfected with the antibody and the dhfr gene thus enabling the selection of CHO cell transformants of the dhfr+ phenotype. Selection is carried out in the absence of thymidine and hypoxanthine. Expression of the antibody gene may be increased by amplification using methotrexate (MTX). This drug is a direct inhibitor of the dhfr enzyme and allows for isolation of resistant colonies which amplify their dhfr gene copy number and therefore the antibody gene sufficiently to survive under these conditions.

Purified antibody molecules, e.g. immunoglobulins, may be prepared by a method comprising the steps of
(a) recombinantly expressing a heterologous nucleic acid molecule encoding an antibody molecule as defined herein above in a mammalian cell, e.g. a CHO or a HEK 293 cell; and
(b) purifying said recombinantly expressed antibody molecule by a method comprising the steps of
  (b1) protein A column purification;
  (b2) ion exchange column purification, e.g. a cation exchange chromatography; and, optionally,
  (b3) size exclusion column purification.

The purification protocol may comprise further steps, like further concentration steps, e.g. diafiltration or analytical steps, e.g. involving analytical columns. The method/process may also comprise virus inactivation steps and/or viral removal steps e.g. via filtrations/nano-filtrations. It is also envisaged and feasible that particular certain steps are repeated (e.g. two ion exchange chromatography steps may be carried out) or that certain steps (e.g. size exclusion chromatography) may be omitted.

Protein A is a group specific ligand which binds to the Fc region of most IgG1 isotypes. It is synthesized by some strains of *Staphylococcus aureus* and can be isolated therefrom and coupled to chromatographic beads. Several types of gel preparations are available commercially.

An example for a protein A column which may be used is a MabSelect (Trademark) column. Ideally the column is equilibrated with 25 mM Tris/HCl, 25 mM NaCl, 5 mM EDTA, the cell culture supernatant is loaded onto the column, the column is washed with 1 M Tris/HCl pH 7.2 and the antibody is eluted at pH 3.2 using 100 mM acetic acid.

Cation-exchange chromatography exploits interactions between positively charged groups in a stationary phase and the sample which is in the mobile phase. When a weak cation exchanger (e.g. CM Toyopearl 650®) is used, the following chromatographic steps are performed: After preequilibration with 100 mM acetic acid pH 4, loading of Protein A eluate and washing with 100 mM acetic acid pH 4 the antibody is eluted and fractionated by applying steps of 250 mM sodium acetate (pH 7.8-8.5) and 500 mM sodium acetate (pH 7.8-8.5). With the first step a mixture of double-glycosylated isoform fraction and mono-glycosylated isoform fraction are normally eluted, using the second step the non-glycosylated isoform fraction is normally eluted.

From a strong cation exchanger (e.g. SP Toyopearl 650) the antibody can be eluted by salt steps: After equilibration of the column with 50 mM acetic acid pH 5.0, loading the Protein A eluate with pH 4 the first elution step using 50 mM acetic acid and 210 mM sodium chloride is performed. Then a second elution step of 50 mM acetic acid and 350 mM sodium chloride is applied. By the first salt step a mixture of the double-glycosylated isoform fraction and mono-glycosylated isoform fraction are normally eluted, by the second salt step the non-glycosylated isoform is normally eluted.

In addition the antibody may also be eluted from a strong cation exchanger column (e.g. SP-Sepharose®) by a salt gradient: After preequilibration, loading and washing the column at pH 4.5 a salt gradient is applied from 50 mM MES pH 5.8 to 50 mM MES/1 M sodium chloride pH 5.8. Here the double-glycosylated isoform, mono-glycosylated isoform and non-glycosylated isoform fractions are normally eluted separately. In the following double-glycosylated isoform fraction and mono-glycosylated isoform fraction may be pooled to result in the product pool and/or a desired antibody mixture.

Further purification of the mixture of double- and mono-glycosylated antibody molecules, e.g. immunoglobulins, may be performed by size exclusion chromatography. An example of a useful column is a Superdex 200® column. Examples of running buffers include histidine/sodium chloride, e.g. 10 mM histidine/125 mM sodium chloride/pH 6, and phosphate buffered saline (PBS).

Anion exchange chromatography in the flow through mode followed by a concentration/diafiltration is an alternative purification step. Q Sepharose® is an example for a resin for the anion exchange step. For example, the eluate from the SP chromatography may be threefold diluted with 37.5 mM Tris/HCl pH 7.9 and passed over a Q-Sepharose column pre-equilibrated with 25 mM Tris/83 mM sodium acetate. The flow through is collected, adjusted to pH 5.5 and concentrated by ultrafiltration using e.g. a Hydrosart 30 kD® membrane. In the following the concentrate may be diafiltrated against for example 10 volumes of 20 mM histidine/HCl pH 5.5.

The above recited purification protocol may also comprise as an additional step (c) an analytical chromatography step, like the use of a Mono-S HR5/5 column. However, also further steps, like diafiltration, for example for concentration of the antibody molecules, is envisaged.

In one embodiment of the present invention, a composition, antibody preparation or antibody pool is provided comprising antibody molecules as described herein or antibody molecules as prepared by the method provided above. In this embodiment of the invention, said composition comprises mono- or double-glycosylated antibodies. In another embodiment, said composition comprises mono- and double-glycosylated (in the variable region(s) of the heavy chain(s)) antibodies and said composition is derived of antibody molecules which lack the glycosylation in the variable region. In context of this embodiment, the term "antibody pool" relates to a mixture of mono- and double-glycosylated (in the variable region(s) of the heavy chain(s)) antibodies which may have been individually isolated and then are combined to one mixture. The antibody mixtures or antibody pools provided herein may comprise 50% mono-glycosylated and 50% double-glycosylated antibodies as defined herein. However, also envisaged are the ratios of 30/70 to 70/30. Yet, the person skilled in the art is aware that also other ratios are envisaged in the antibody mixtures of this invention. For example, also 10/90 or 90/10, 20/80 or 80/20 as well as 40/60 or 60/40 may be employed in context of this invention. As also documented in the examples, a particular useful ratio in the ANTIBODY MIXTURES of the invention comprises double-glycosylated and mono-glycosylated antibody as defined herein above is a ratio from 40/60 to 45/55.

The compositions provided herein are particularly useful in diagnostic or in a pharmaceutical composition.

Accordingly, the invention provides for diagnostic or pharmaceutical compositions comprising
(a) an antibody molecule as defined above comprising one antigen binding site with a glycosylated Asn;
(b) an antibody molecule as defined above, comprising two antigen binding sites with a glycosylated Asn; or, most preferably,
(c) a combination of antibody molecules (a) to (b).

The combination (c) as provided herein, comprising the antibody molecule(s) comprising one antigen binding site with a glycosylated Asn and the antibody molecule(s) comprising two antigen binding sites with a glycosylated Asn are devoid of non-glycosylated (in respect to the variable region of the heavy chain) isoforms. As pointed out above, the term "devoid of non-glycosylated (in respect to the variable region of the heavy chain) isoform" relates to combinations/antibody pools/antibody preparations, wherein less than 5%, e.g. less than 4%, less than 3%, less than 2%, less than 1% or even less than 0.5% of the antibody species in said combination is non-glycosylated in the variable region of the heavy chain. As demonstrated in the examples, said combinations/antibody pools/antibody preparations may comprise almost no (less than 0.5%) non-glycosylated isoforms. The percentage and/or the amount of a given glycosylation isoform (as defined herein, e.g. glycosylation in the variable region of the heavy chain, see inter alia appended FIG. 14) in a given ANTIBODY COMPOSITION may easily be determined by methods known in the art. These methods comprise, but are not limited to, mass spectrometry, SDS-PAGE analysis ion exchange, HPLL, ELISA and the like.

As shown in the appended examples, the specific and sensitive immuno-decoration of genuine Alzheimer's β-amyloid plaques by the antibodies of the invention is demonstrated in vitro with immunohistochemical staining experiments using cryo-sections of human brain tissue from Aβ patients. Effective staining of β-amyloid plaques from brain slices was demonstrated also with human anti-Aβ antibodies from patients vaccinated with Aβ (Hock, 2002, Nature Medicine, 8, 1270-1275). Further, immuno-decoration is also demonstrated in a transgenic animal model featuring human β-amyloid plaque burden (Richards, 2003, J. Neuroscience, 23, 8989-9003). In similar animal models it had been demonstrated that this plaque binding led to their clearance and subsequently to an improvement of disease related symptoms, whereas the involvement of Fc-dependent processes had been discussed (Bard, 2000, Nature Medicine, 6, 916-919; Wilcock, 2003, Neurobiology Disease, 15, 11-20; Wilcock, 2004, J. Neuroscience, 24, 6144-6151). Furthermore, effective binding of anti-Aβ antibodies to β-amyloid plaques was reported to correlate with slower disease progression (Hock, 2002, Nature Medicine, 8, 1270-1275; Hock, 2003, Neuron, 38, 547-554). This and post-mortem analysis of human brain tissue suggests that phagocytosis of microglia cells is mechanistically involved in the plaque clearance in man (Nicoll, 2003, Nature Medicine, 9, 448-452). Therefore the antibody of the present invention or comprised in particular in pharmaceutical compositions is a human IgG1, which is mainly responsible for FcR-dependent processes in humans. The efficient β-amyloid plaque immuno-decoration of the antibodies of the invention/the mixture of the invention suggests that the drug will be efficacious for passive immunization to clear existing and prevent formation of β-amyloid plaques in humans.

In addition antibodies should preferably cross the blood-brain-barrier to reach their place of destination. For large size molecules as human IgGs this process is dramatically reduced, so that only about 0.1 to 0.2% of the plasma concentration of an antibody can be reached in CSF. The mechanism of plaque clearance is still a subject of controversial debates, which might involve peripheral effects on the Aβ peptide (Dodart, 2002, Nature Neuroscience, 5: 452-457). Thus, the generated therapeutic antibody or the corresponding inventive mixtures of mono- and double glycosylated (in the variable region heavy chain) of the invention have also the property to depolymerize Aβ multimers in vitro without involvement of Fc-dependent processes and to bind to soluble Aβ monomers and oligomers in CSF, since neutralization of soluble monomeric Aβ peptides or oligomeric Aβ peptides (e.g. aggregation intermediates) may also contribute to overall amyloid lowering effect (Du, 2003, Brain, 126: 1-5).

The compositions of the invention may be administered in solid or liquid form and may be, inter alia, in a form of (a) powder(s), (a) tablet(s), (a) solution(s) or (an) aerosol(s). Said composition may comprise on or more antibodies/antibody molecules of the invention most preferably a mixture of mono- and double-glycosylated antibodies as provided herein.

It is preferred that said pharmaceutical composition, optionally comprises a pharmaceutically acceptable carrier and/or diluent. The herein disclosed pharmaceutical composition may be particularly useful for the treatment of neurological and/or neurodegenerative disorders. Said disorders comprise, but are not limited to Alzheimer's disease, amyothrophic lateral sclerosis (ALS), hereditary cerebral hemorrhage with amyloidosis Dutch type, Down's syndrome, HIV-dementia, Parkinson's disease and neuronal disorders related to aging. The pharmaceutical composition of the invention is, inter alia, envisaged as potent inhibitor of amyloid plaque formation or as a potent stimulator for the de-polymerization of amyloid plaques. Therefore, the present invention provides for pharmaceutical compositions comprising the compounds of the invention to be used for the treatment of amyloidogenic diseases/disorders. The term "amyloidogenic disease/disorder" includes any disease associated with or caused by the formation or deposition of amyloid fibrils and/or pathological APP proteolysis. Exemplary amyloidogenic disease include, but are not limited to Alzheimer's disease (AD), Down's Syndrome, dementia associated with Lewy body formation, Parkinson's Disease with dementia, mild cognitive impairment, cerebral amyloid angiopathy and vascular dementia. Different amyloidogenic diseases are defined and/or characterized by the nature of the polypeptide-component of the amyloid deposits. For example, the amyloid-β protein is characteristic for the amyloid deposits found in subjects having Alzheimer's disease.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. Suitable carriers may comprise any material which, when combined with the anti-Aβ specific binding agent or antibody, retains the high-affinity binding of Aβ and is nonreactive with the subject's immune systems including excipients, surfactants, tonicity agents and the like; see Remington's Pharmaceutical Sciences (1980) 16th edition, Osol, A. Ed. These pharmaceutical compositions can be administered to the subject at a suitable dose. Administration of the suitable compositions may be effected by different ways, e.g., by parenteral, subcutaneous, intraperitoneal, topical, intrabronchial, intrapulmonary and intranasal administration and, if desired for local treatment, intralesional administration. Parenteral administrations include intraperitoneal, intramuscular, intradermal, subcutaneous intravenous or intraarterial, administration. It is particularly preferred that said administration is carried out by injection and/or delivery, e.g., to a site in a brain artery or directly into brain tissue. The compositions of the invention may also be administered directly to the target site, e.g., by biolistic delivery to an external or internal target site, like the brain.

Pharmaceutical compositions comprising the herein described glycosylated antibodies are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-Methylglucosamine (so-called "Meglumine"), galactosamine and neuraminic acid; and/or non-ionic surfactants such as Tween, Brij Pluronics, Triton-X or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization), however also solutions comprising antibacterial agents may be used for the production of pharmaceutical compositions for parenteral administration; see also Chen (1992) Drug Dev Ind Pharm 18, 1311-54.

Exemplary antibody concentrations in the pharmaceutical composition may range from about 1 mg/mL to about 200 mg/ml or from about 50 mg/mL to about 200 mg/mL, or from about 150 mg/mL to about 200 mg/mL. For clarity reasons, it is emphasized that the concentrations as indicated herein relate to the concentration in a liquid or in a liquid that is accurately reconstituted from a solid form.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. Preferably the aqueous formulation is isotonic, although hypertonic or hypotonic solutions may be suitable. The term "isotonic" denotes a solution having the same tonicity as some other solution with which it is compared, such as physiological salt solution and the blood serum. Tonicity agents may be used in an amount of about 5 mM to about 350 mM, in particular in an amount of 105 mM to 305 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Preferred polyoxyethylenesorbitan-fatty acid esters are polysorbate 20, (sold under the trademark Tween 20™) and polysorbate 80 (sold under the trademark Tween 80™). Preferred polyethylene-polypropylene copolymers are those sold under the names Pluronic® F68 or Poloxamer 188™. Preferred Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants are generally used in an amount of about 10 mM to 500 nM.

In one embodiment, the formulation contains the above-identified agents (i.e. glycosylated antibody, surfactant, buffer, stabilizer and/or tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In another embodiment, a preservative may be included in the formulation, e.g., at concentrations ranging from about 0.001 to about 2% (w/v).

In one embodiment, the antibody formulation of the invention is a liquid or lyophilized formulation suitable for parenteral administration that may comprise:
  about 1 to about 200 mg/mL of the herein described glycosylated antibodies or ANTIBODY COMPOSITION,
  about 0.001 to about 1% of at least one surfactant;
  about 1 to about 100 mM of a buffer;
  optionally about 10 to about 500 mM of a stabilizer and/or about 5 to about 305 mM of a tonicity agent;
  at a pH of about 4.0 to about 7.0.

In a preferred embodiment, the parenteral formulation of the invention is a liquid or lyophilized formulation comprising:
  about 1 to about 200 mg/mL of the herein described glycosylated antibodies or ANTIBODY COMPOSITION,
  0.04% Tween 20 w/v,
  20 mM L-histidine,
  250 mM Sucrose,
  at pH 5.5.

In a more preferred embodiment, the parenteral formulation according to the invention also comprises a lyophilized formulation comprising:
  15 mg/mL of the herein described glycosylated antibodies or ANTIBODY COMPOSITION,
  0.04% Tween 20 w/v,
  20 mM L-histidine,
  250 mM Sucrose,
  at pH 5.5;
or
  75 mg/mL of the herein described glycosylated antibodies or ANTIBODY COMPOSITION,
  0.04% Tween 20 w/v,
  20 mM L-histidine,
  250 mM Sucrose,
  at pH 5.5;
or
  75 mg/mL of the herein described glycosylated antibodies or ANTIBODY COMPOSITION,
  0.02% Tween 20 w/v,
  20 mM L-histidine,
  250 mM Sucrose,
  at pH 5.5;
or
  75 mg/mL of the herein described glycosylated antibodies or ANTIBODY COMPOSITION,
  0.04% Tween 20 w/v,
  20 mM L-histidine,
  250 mM Trehalose,
  at pH 5.5;
or
  75 mg/mL of the herein described glycosylated antibodies or ANTIBODY COMPOSITION,
  0.02% Tween 20 w/v,
  20 mM L-histidine,
  250 mM Trehalose,
  at pH 5.5

In another more preferred embodiment, the parenteral formulation according to the invention also comprises a liquid formulation comprising:
  7.5 mg/mL of the herein described glycosylated antibodies or ANTIBODY COMPOSITION,
  0.022% Tween 20 w/v,
  120 mM L-histidine,
  250 125 mM Sucrose,
  at pH 5.5;
or
  37.5 mg/mL of the herein described glycosylated antibodies or ANTIBODY COMPOSITION,
  0.02% Tween 20 w/v,
  10 mM L-histidine,
  125 mM Sucrose,
  at pH 5.5;
or
  37.5 mg/mL of the herein described glycosylated antibodies or ANTIBODY COMPOSITION,
  0.01% Tween 20 w/v,
  10 mM L-histidine,
  125 mM Sucrose,
  at pH 5.5;
or
  37.5 mg/mL of the herein described glycosylated antibodies or ANTIBODY COMPOSITION,
  0.02% Tween 20 w/v,
  10 mM L-histidine,
  125 mM Trehalose,
  at pH 5.5;
or
  37.5 mg/mL of the herein described glycosylated antibodies or ANTIBODY COMPOSITION,
  0.01% Tween 20 w/v,
  10 mM L-histidine,
  125 mM Trehalose,
  at pH 5.5;

or
75 mg/mL of the herein described glycosylated antibodies or ANTIBODY COMPOSITION,
0.02% Tween 20 w/v,
20 mM L-histidine,
250 mM Trehalose,
at pH 5.5;
or
75 mg/mL of the herein described glycosylated antibodies or ANTIBODY COMPOSITION,
0.02% Tween 20 w/v,
20 mM L-histidine,
250 mM Mannitol,
at pH 5.5;
or
75 mg/mL of the herein described glycosylated antibodies or ANTIBODY COMPOSITION,
0.02% Tween 20 w/v,
20 mM L histidine,
140 mM Sodium chloride,
at pH 5.5;
or
150 mg/mL of the herein described glycosylated antibodies or ANTIBODY COMPOSITION,
0.02% Tween 20 w/v,
20 mM L-histidine,
250 mM Trehalose,
at pH 5.5.
or
150 mg/mL of the herein described glycosylated antibodies or ANTIBODY COMPOSITION,
0.02% Tween 20 w/v,
20 mM L-histidine,
250 mM Mannitol,
at pH 5.5.
or
150 mg/mL of the herein described glycosylated antibodies or ANTIBODY COMPOSITION,
0.02% Tween 20 w/v,
20 mM L-histidine,
140 mM Sodium chloride,
at pH 5.5.
or
10 mg/mL Abeta antibody,
0.01% Tween 20 w/v,
20 mM L-histidine,
140 mM Sodium chloride,
at pH 5.5.

In one embodiment, the pharmaceutical composition of the present invention is the liquid formulation which comprises:
10 mg/mL Abeta antibody,
0.01% Tween 20 w/v,
20 mM L-histidine,
140 mM Sodium chloride,
at pH 5.5.

In another embodiment, the pharmaceutical composition of the present invention is the lyophilized formulation which comprises:
75 mg/mL Abeta antibody,
0.04% Tween 20 w/v,
20 mM L-histidine,
250 mM Sucrose,
at pH 5.5.

The term "herein described glycosylated antibodies" in context of exemplified formulations may comprise in this invention the herein defined mono-glycosylated antibodies, the herein defined double-glycosylated antibodies as well as mixtures thereof.

The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Proteinaceous pharmaceutically active matter may be present in amounts between 1 ng and 20 mg/kg body weight per dose, e.g. between 0.1 mg to 10 mg/kg body weight, e.g. between 0.5 mg to 5 mg/kg body weight; however, doses below or above this exemplary range are envisioned, especially considering the aforementioned factors. If the regimen is a continuous infusion, it should also be in the range of 1 µg to 10 mg per kilogram of body weight per minute.

The pharmaceutical compositions as described herein may be formulated to be short-acting, fast-releasing, long-acting, or sustained-releasing. Hence, the pharmaceutical compositions may also be suitable for slow release or for controlled release.

Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Progress can be monitored by periodic assessment. The compositions, i.e. the mono- and/or double-glycosylated antibodies of the invention or a mixture thereof, may be administered locally or systemically. It is of note that peripherally administered antibodies can enter the central nervous system, see, inter alia, Bard (2000), Nature Med. 6, 916-919. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents depending on the intended use of the pharmaceutical composition. Said agents may be drugs acting on the central nervous system, like, neuroprotective factors, cholinesterase inhibitors, agonists of Ml muscarinic receptor, hormones, antioxidants, inhibitors of inflammation etc. It is particularly preferred that said pharmaceutical composition comprises further agents like, e.g. neurotransmitters and/or substitution molecules for neurotransmitters, vitamin E or alpha-lipoic acid.

The person skilled in the art, in particular but not limiting biochemists, biologists, chemists, pharmacists and groups of said professionals are readily in a position to work and generate the above recited pharmaceutical compositions. Also medical personal skilled in they art, like attending physicians are aware how such pharmaceutical compositions may be administered to a patient in need of a treatment with the herein defined pharmaceutical compositions. Such an administration may comprise systemic administration, e.g. via infusions and/or injections. However, also the direct administration of the compounds and/or compound mixtures of the invention to the brain is envisaged. For example, the compound or compound mixture or compound formulation may be administered by direct intraventricular or intrathecal injection to the brain, preferably via slow infusion to minimize impact on brain parenchyma. Also slow release implant in the brain may be employed. It is also envisaged that gene therapy approaches are employed, for example by use of implanted recombinant cells that produce the antibodies as defined in this invention. These "recombinant cells" should be capable of providing the herein defined glycosylations in the variable regions/parts of the antibodies described herein, in particular the anti-Aβ antibodies of the invention. Yet, as pointed out above one advantage of the antibodies/antibody mixtures of the present invention is their capability to cross the blood-brain barrier and to bind to amyloid plaques. The pharmaceutical compositions of the invention described infra can be used for the treatment of all kinds of diseases hitherto unknown or being related to or dependent on pathological APP aggregation or pathological APP processing. They may be particularly useful for the treatment of Alzheimer's disease and other diseases where extracellular deposits of amyloid-β, appear to play a role. They may be desirably employed in humans, although animal treatment is also encompassed by the methods, uses and compositions described herein.

In a preferred embodiment of the invention, the composition of the present invention as disclosed herein above is a diagnostic composition further comprising, optionally, suitable means for detection. The diagnostic composition comprises at least one of the aforementioned compounds of the invention, namely the glycosylated antibodies described herein.

Said diagnostic composition may comprise the compounds of the invention, in particular the glycosylated antibody molecules of the present invention, soluble form/liquid phase but it is also envisaged that said compounds are bound to/attached to and/or linked to a solid support.

Solid supports may be used in combination with the diagnostic composition as defined herein or the compounds of the present invention may be directly bound to said solid supports. Such supports are well known in the art and comprise, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The compound(s) of the invention, in particular the antibodies of the present invention, may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Appropriate labels and methods for labeling have been identified above and are furthermore mentioned herein below. Suitable methods for fixing/immobilizing said compound(s) of the invention are well known and include, but are not limited to ionic, hydrophobic, covalent interactions and the like.

It is particularly preferred that the diagnostic composition of the invention is employed for the detection and/or quantification of APP and/or APP-processing products, like amyloid-β or for the detection and/or quantification of pathological and/or (genetically) modified APP-cleavage sides.

As illustrated in the appended examples, the inventive glycosylated antibody molecules are particularly useful as diagnostic reagents in the detection of genuine human amyloid plaques in brain sections of Alzheimer's Disease patients by indirect immunofluorescence.

It is preferred that said compounds of the present invention to be employed in a diagnostic composition are detectably labeled. A variety of techniques are available for labeling biomolecules, are well known to the person skilled in the art and are considered to be within the scope of the present invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Commonly used labels comprise, inter alia, fluorochromes (like fluorescein, rhodamine, Texas Red, etc.), enzymes (like horse radish peroxidase, β-galactosidase, alkaline phosphatase), radioactive isotopes (like $^{32}$P or $^{125}$I), biotin, digoxygenin, colloidal metals, chemi- or bioluminescent compounds (like dioxetanes, luminol or acridiniums). Labeling procedures, like covalent coupling of enzymes or biotinyl groups, iodinations, phosphorylations, biotinylations, etc. are well known in the art.

Detection methods comprise, but are not limited to, autoradiography, fluorescence microscopy, direct and indirect enzymatic reactions, etc. Commonly used detection assays comprise radioisotopic or non-radioisotopic methods. These comprise, inter alia, Westernblotting, overlay-assays, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay), and CLIA (Chemioluminescent Immune Assay).

Furthermore, the present invention provides for the use of the glycosylated antibody molecules of invention, or an antibody molecule produced by the method of the invention, or a mixture of mono- and double-glycosylation antibodies as provided herein for the preparation of a pharmaceutical or a diagnostic composition for the prevention, treatment and/or diagnosis of a disease associated with amyloidogenesis and/or amyloid-plaque formation. It is further preferred that the compounds described herein, in particular the antibody molecules of the invention, be employed in the prevention and/or treatment of neuropathologies associated with modified or abnormal APP-processing and/or amyloidogenesis. The antibody molecules, e.g. in the format of (engineered) immunoglobulins, like antibodies in a IgG framework, in particular in an IgG1-framework, or in the format of chimeric antibodies (in particular fully humanized antibodies or complete antibodies), bispecific antibodies, single chain Fvs (scFvs) or bispecific scFvs and the like are employed in the preparation of the pharmaceutical compositions provided herein. Yet, the antibody molecules and mixtures provided herein are also useful in diagnostic settings as documented in the appended examples, since the antibody molecules of the invention specifically interact with/detect Aβ4 and/or amyloid deposits/plaques.

Therefore an inventive use of the compounds of the present invention is the use for the preparation of a pharmaceutical composition for a neurological disorder which calls for amelioration, for example by disintegration of β-amyloid plaques, by amyloid (plaque) clearance or by passive immunization against β-amyloid plaque formation. As illustrated in the appended examples, the inventive antibody molecules are particularly useful in preventing Aβ aggregation and in depolymerization of already formed amyloid aggregates. Accordingly, the inventive glycosylated antibodies or a mixture of mono- and double-glycosylated antibodies as described herein are to be employed in the reduction of pathological amyloid deposits/plaques, in the clearance of amyloid plaques/plaque precursors as well as in neuronal protection. It is in particular envisaged that the antibody molecules of the invention be employed in the in vivo prevention of amyloid plaques as well as in in vivo clearance of pre-existing amyloid plaques/deposits. Furthermore, the antibody molecules or the mixtures of the invention may be employed in passive immunization approaches against Aβ peptide and aggregates of Aβ, namely amyloid-β plaques. Clearance of Aβ4/Aβ4 deposits may, inter alia, be achieved by the medical use of antibodies of the present invention which comprise an Fc-part. Said Fc-part of an antibody may be particularly useful in Fc-receptor mediated immune responses, e.g. the attraction of macrophages (phagocytic cells and/or microglia) and/or helper cells. For the mediation of Fc-part-related immunoresponses, the antibody molecule of the invention is preferably in an (human) IgG1-framework. As discussed herein, the preferred subject to be treated with the inventive antibody molecules, or antibody mixtures is a human subject. Other frameworks, like IgG2a- or IgG2b-frameworks for the inventive antibody molecules are also envisaged. Immunoglobulin frameworks in IgG2a and IgG2b format are particular envisaged in mouse settings, for example in scientific uses of the inventive antibody molecules, e.g. in tests on transgenic mice expressing (human) wild type or mutated APP, APP-fragments and/or Aβ4.

The above recited diseases associated with amyloidogenesis and/or amyloid-plaque formation comprise, but are not limited to dementia, Alzheimer's disease, motor neuropathy, Parkinson's disease, ALS (amyotrophic lateral sclerosis), scrapie, HIV-related dementia as well as Creutzfeld-Jakob disease, hereditary cerebral hemorrhage, with amyloidosis Dutch type, Down's syndrome and neuronal disorders related to aging. The antibody molecules of the invention and the compositions provided herein may also be useful in the amelioration and or prevention of inflammatory processes relating to amyloidogenesis and/or amyloid plaque formation.

Accordingly, the present invention also provides for a method for treating, preventing and/or delaying neurological and/or neurodegenerative disorders comprising the step of administering to a subject suffering from said neurological and/or neurodegenerative disorder and/or to a subject susceptible to said neurological and/or neurodegenerative disorder an effective amount of a an anti Aβ antibody molecule or a mixture of the inventive mono- and/or double-glycosylated A-beta antibodies as provided herein and/or a composition as defined herein above. The treatment as provided herein may comprise the administration for the compounds/compositions of this invention alone or in form of a co-therapy treatment, i.e. in combination with other drugs or medicaments. In a particular preferred embodiment of the invention, a method for treating, preventing and/or delaying neurological and/or neurodegenerative disorders is provided that comprises the step of administering to a patient in need of a corresponding medical intervention the antibody mixture comprising mono- and double-glycosylated antibodies directed against Aβ and as provided herein.

The term "treatment" used herein envisages the administration of mono- and/or double-glycosylated antibodies (or mixtures thereof) as described herein to a patient in need thereof. Said patient may be a human patient, in one embodiment an human suffering from or being susceptible to a disorder related to pathological APP processing. Accordingly, the term "treatment" as used herein comprises the prophylactic as well as the curative administration of the compounds or compound mixtures provided herein.

An disorder to be treated by the compounds and composition provided herein is Alzheimer's disease. Patients having a diagnosis of probable Alzheimer's disease based on the National Institute of Neurological and Communicative Disorders and Stroke/Alzheimer's Disease and Related Disorders Association criteria for this diagnosis (NINCDS/ADRDA criteria) Mckhann et al., 1984.

Also envisaged in context of this invention is the medical use of the compounds and/or compositions provided herein in a "co-therapy" setting. for example in the case of APP-related disorders, like Alzheimer's disease. In said case, co-therapy with approved medicaments, like memantine, donepezil, rivastigmine or galantamine, is envisaged.

In yet another embodiment, the present invention provides for a kit comprising at least one glycosylated antibody molecule as defined herein or the mixture of the inventive mono- and/or double-glycosylated methods as provided herein. Advantageously, the kit of the present invention further comprises, optionally (a) buffer(s), storage solutions and/or remaining reagents or materials required for the conduct of medical, scientific or diagnostic assays and purposes. Furthermore, parts of the kit of the invention can be packaged individually in vials or bottles or in combination in containers or multicontainer units.

The kit of the present invention may be advantageously used, inter alia, for carrying out the method of the invention and could be employed in a variety of applications referred herein, e.g., as diagnostic kits, as research tools or medical tools. Additionally, the kit of the invention may contain means for detection suitable for scientific, medical and/or diagnostic purposes. The manufacture of the kits follows preferably standard procedures which are known to the person skilled in the alt.

BRIEF DESCRIPTION OF THE DRAWINGS

The figures show:
FIG. 4: Whole IgG ESI-MS analysis of ANTIBODY A isoforms. Molecular mass of main peak is indicated in Da. A: non-glycosylated ANTIBODY A; B: mono-glycosylated ANTIBODY A; C: double-glycosylated ANTIBODY A
FIG. 5: Scheme of deduced ANTIBODY N-glycosylation patterns. Structures that occur only partially are indicated by parenthesis. A: Complex Type; B: Hybrid Type; C: Oligomannose Type; GlcNAc=N-acetyl-glucosamine, Man=mannose; Gal=galactose; Fuc=fucose; NeuAc=N-acetyl-neuraminic acid

FIG. 27: Table showing different glycan structures of ANTIBODY A in the constant region of the heavy chain (Asn 306; first two columns) and in the variable region of the heavy chain (Asn 52; third and fourth column).

EXAMPLES

Figure 1A:
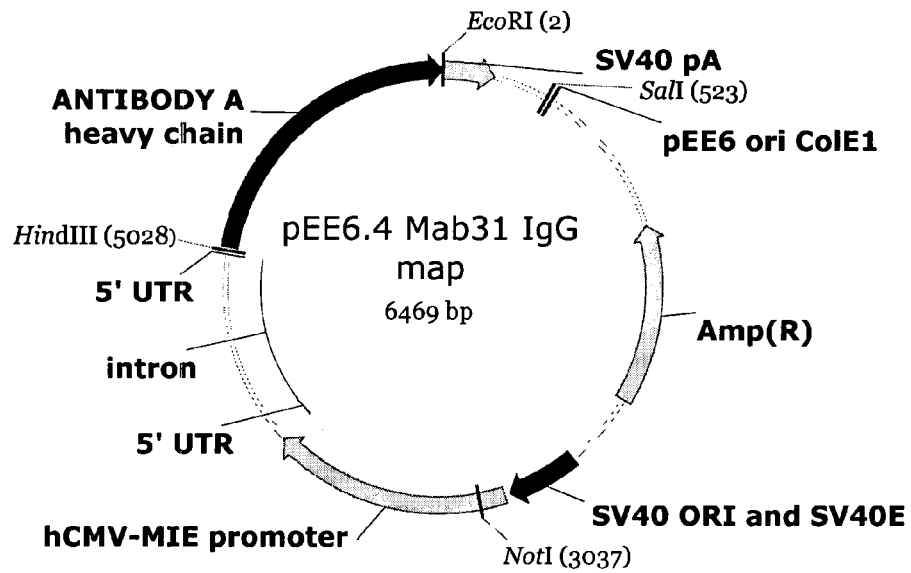
FIG. 1: Plasmid map showing the insertion sites for the heavy and light chain sequences

The following, non-limiting examples illustrate the invention.

Example 1

Generation of ANTIBODY A Via Cloning Techniques

In accordance with the present invention, an IgG1 molecule was generated via common cloning techniques. ANTIBODY A is, in its coding sequence and in its expressed amino acid sequence characterized by its variable region of the heavy chain ($V_H$). The corresponding example of a heavy encoded by a DNA sequence as follows:

```
                                          (SEQ ID NO: 5)
caggtggaattggtggaaagcggcggcggcctggtgcaaccgggcggcag cctgcgtctgagctgcgcggcctccggatttacctttagcagctatgcga tgagctgggtgcgccaagcccctgggaagggtctcgagtgggtgagcgct attaatgcttctggtactcgtacttattatgctgattctgttaagggtcg ttttaccatttcacgtgataattcgaaaaacaccctgtatctgcaaatga acagcctgcgtgcggaagatacggccgtgtattattgcgcgcgtggtaag ggtaatactcataagccttatggttatgttcgttattttgatgtttgggg ccaaggcaccctggtgacggttagctcagcctccaccaagggtccatcgg
```

```
-continued
tcttcccctggcaccctcctccaagagcacctctgggggcacagcggcc ctgggctgcctggtcaaggactacttccccgaaccggtgacggtgtcgtg gaactcaggcgccctgaccagcggcgtgcacaccttcccggctgtcctac agtcctcaggactctactccctcagcagcgtggtgaccgtgccctccagc agcttgggcacccagacctacatctgcaacgtgaatcacaagcccagcaa caccaaggtggacaagaaagttgagcccagatatcgtgcgatatcgtgca atcttgtgacaaaactcacacatgcccaccgtgcccagcacctgaactcc tgggggaccgtcagtcttcctcttccccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgg gtggtcagcgtcctcaccgtcctgcaccaggactggctgaatggcaagga gtacaagtgcaaggtctccaacaaagccctcccagcccccatcgagaaaa ccatctccaaagccaaagggcagccccgagaaccacaggtgtacaccctg cccccatcccgggatgagctgaccaagaaccaggtcagcctgacctgcct ggtcaaaggcttctatcccagcgacatcgccgtggagtgggagagcaatg ggcagccggagaacaactacaagaccacgcctcccgtgctggactccgac ggctccttcttcctctacagcaagctcaccgtggacaagagcaggtggca gcaggggaacgtcttctcatgctccgtgatgcatgaggctctgcacaacc actacacgcagaagagcctctccctgtctccgggtaaatga.
``` and codes for the following immunoglobulin H-chain:

```
                                          (SEQ ID NO: 6)
QVELVESGGGLVQPGGSLRLSCAASGFTFSSYAMSWVRQAPGKGLEWVSA

INASGTRTYYADSVKGRFTISRDNSKNTLYLQMNSLRAEDTAVYYCARGK

GNTHKPYGYVRYFDVWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVF

LFPPKPKDTLMISRTPEVTCVVVDVSHEDPEVKPNWYVDGVEVHNAKTKP

REEQYNSTYRVVSVLTVLHQDWLNGKEYKCKVSNKALPAPTEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK
```

The same heavy chain may also be encoded by a sequence comprising an additional "leader sequence" as shown in the following sequence

```
                                          (SEQ ID NO: 25)
atgaaacacctgtggttcttcctcctgctggtggcagctcccagatgggt cctgtcccaggtggaattggtggaaagcggcggcggcctggtgcaaccgg gcggcagcctgcgtctgagctgcgcggcctccggatttacctttagcagc tatgcgatgagctgggtgcgccaagcccctgggaagggtctcgagtgggt gagcgctattaatgcttctggtactcgtacttattatgctgattctgtta
```

-continued

```
agggtcgttttaccatttcacgtgataattcgaaaaacaccctgtatctg caaatgaacagcctgcgtgcggaagatacggccgtgtattattgcgcgcg tggtaagggtaatactcataagccttatggttatgttcgttattttgatg tttggggccaaggcaccctggtgacggttagctcagcctccaccaagggt ccatcggtcttcccctggcaccctcctccaagagcacctctgggggcac agcggccctgggctgcctggtcaaggactacttccccgaaccggtgacgg tgtcgtggaactcaggcgccctgaccagcggcgtgcacaccttcccggct gtcctacagtcctcaggactctactccctcagcagcgtggtgaccgtgcc ctccagcagcttgggcacccagacctacatctgcaacgtgaatcacaagc ccagcaacaccaaggtggacaagaaagttgagcccaaatcttgtgacaaa actcacatgcccaccgtgcccagcacctgaactcctgggggaccgtc agtcttcctcttccccccaaaacccaaggacaccctcatgatctcccgga cccctgaggtcacatgcgtggtggtggacgtgagccacgaagaccctgag gtcaagttcaactggtacgtggacggcgtggaggtgcataatgccaagac aaagccgcgggaggagcagtacaacagcacgtaccgggtggtcagcgtcc tcaccgtcctgcaccaggactggctgaatggcaaggagtacaagtgcaag gtctccaacaaagcccccagccccatcgagaaaaccatctccaaagc caaagggcagccccgagaaccacaggtgtacaccctgcccccatcccggg atgagctgaccaagaaccaggtcagcctgacctgcctggtcaaaggcttc tatcccagcgacatcgccgtggagtgggagagcaatgggcagccggagaa caactacaagaccacgcctcccgtgctggactccgacggctccttcttcc tctacagcaagctcaccgtggacaagagcaggtggcagcaggggaacgtc ttctcatgctccgtgatgcatgaggctctgcacaaccactacacgcagaa gagcctctccctgtctccgggtaaatga
```

The corresponding amino acid sequence would be (SEQ ID NO: 26)
MKHLWFFLLLVAAPRWVLSQVELVESGGGLVQPGGSLRLSCAASGFTFSS

YAMSWVRQAPGKGLEWVSAINASGTRTYYADSVKGRFTISRDNSKNTLYL

QMNSLRAEDTAVYYCARGKGNTHKPYGYVRYFDVWGQGTLVTVSSASTKG

PSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

Similarly, the light chain of ANTIBODY A is encoded by the following nucleotide sequence:

(SEQ ID NO: 7)
```
gatatcgtgctgacccagagcccggcgaccctgagcctgtctccgggcga acgtgcgaccctgagctgcagagcgagccagagcgtgagcagcagctatc tggcgtggtaccagcagaaaccaggtcaagcaccgcgtctattaatttat ggcgcgagcagccgtgcaactgggtcccggcgcgttttagcggctctgg atccggcacggattttaccctgaccattagcagcctggaacctgaagact ttgcgacttattattgccttcagatttataatatgcctattacctttggc cagggtacgaaagttgaaattaaacgtacggtggctgcaccatctgtctt catcttcccgccatctgatgagcagttgaaatctggaactgcctctgttg tgtgcctgctgaataacttctatcccagagaggccaaagtacagtggaag gtggataacgcccctccaatcgggtaactcccaggagagtgtcacagagca ggacagcaaggacagcacctacagcctcagcagcaccctgacgctgagca aagcagactacgagaaacacaaagtctacgcctgcgaagtcacccatcag ggcctgagctcgcccgtcacaaagagcttcaacaggggagagtgttag
``` and codes for the following amino acid sequence (L-chain):

(SEQ ID NO: 8)
DIVLTQSPATLSLSPGERATLSCRASQSVSSSYLAWYQQKPGQAPRLLIY

GASSRATGVPARFSGSGSGTDFTLTISSLEPEDFATYYCLQIYNMPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Again, also here, a "leader sequence" may be employed and the corresponding sequences would be (SEQ ID NO: 27)
```
atggtgttgcagacccaggtcttcatttctctgttgctctggatctctgg tgcctacggggatatcgtgctgacccagagcccggcgaccctgagcctgt ctccgggcgaacgtgcgaccctgagctgcagagcgagccagagcgtgagc agcagctatctggcgtggtaccagcagaaaccaggtcaagcaccgcgtct attaatttatggcgcgagcagccgtgcaactgggtcccggcgcgttttta gcggctctggatccggcacggattttaccctgaccattagcagcctggaa cctgaagactttgcgacttattattgccttcagatttataatatgcctat tacctttggccagggtacgaaagttgaaattaaacgtacggtggctgcac catctgtcttcatcttcccgccatctgatgagcagttgaaatctggaact gcctctgttgtgtgcctgctgaataacttctatcccagagaggccaaagt acagtggaaggtggataacgcccctccaatcgggtaactcccaggagagtg tcacagagcaggacagcaaggacagcacctacagcctcagcagcaccctg acgctgagcaaagcagactacgagaaacacaaagtctacgcctgcgaagt cacccatcagggcctgagctcgcccgtcacaaagagcttcaacaggggag agtgttag
```

This sequence encodes the following amino acid sequence (SEQ ID NO: 28)
MVLQTQVFISLLLWISGAYGDIVLTQSPATLSLSPGERATLSCRASQSVS

SSYLAWYQQKPGQAPRLLIYGASSRATGVPARFSGSGSGTDFTLTISSLE

PEDFATYYCLQIYNMPITFGQGTKVEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

These sequences above are known from MAB31 as disclosed in WO 03/070760.

However, the heavy and light chains of the exemplified ANTIBODY A may also be encoded by a sequence as shown below:

a) the heavy chain (SEQ ID NO: 23)
atggagtttgggctgagctgggttttcctcgttgctcttttaagaggtga ttcatggagaaatagagagactgagtgtgagtgaacatgagtgagaaaaa ctggatttgtgtggcattttctgataacggtgtccttctgtttgcaggtg tccagtgtcaggtggagctggtggagtctgggggaggcctggtccagcct ggggggtccctgagactctcctgtgcagcgtctggattcaccttcagtag ctatgccatgagctgggtccgccaggctccaggcaaggggctcgagtggg tgtccgccataaacgccagcggtaccgcacctactatgcagactccgtg aagggccgattcaccatctccagagacaattccaagaacacgctgtatct gcaaatgaacagcctgagagccgaggacacggctgtgtattactgtgcga gaggcaaggggaacacccacaagccctacggctacgtacgctactttgac gtgtggggccaaggaaccctggtcaccgtctcctcaggtgagtcctcaca acctctctcctgcggccgcagcttgaagtctgaggcagaatcttgtccag ggtctatcggactcttgtgagaattagggggctgacagttgatggtgacaa tttcagggtcagtgactgtctggtttctctgaggtgagactggaatatag gtcaccttgaagactaaagaggggtccaggggcttttctgcacaggcagg gaacagaatgtggaacaatgacttgaatggttgattcttgtgtgacacca agaattggcataatgtctgagttgcccaagggtgatcttagctagactct gggggttttttgtcgggtacagaggaaaaacccactattgtgattactatgc tatggactactggggtcaaggaacctcagtcaccgtctcctcaggtaaga atggcctctccaggtctttattttaacctttgttatggagttttctgag cattgcagactaatcttggatatttgccctgagggagccggctgagagaa gttgggaaataaatctgtctagggatctcagagcctttaggacagattat ctccacatctttgaaaaactaagaatctgtgtgatggtgttggtggagtc cctgatgatgggataggaactttggaggctcatttgagggagatgctaa aacaatcctatggctggagggatagttggggctgtagttggagattttca gttttagaatgaagtattagctgcaatacttcaaggaccacctctgtga caaccattttatacagtatccaggcatagggacaaaaagtggagtggggc actttctttagatttgtgaggaatgttccacactagattgtttaaaactt catttgttggaaggagctgtcttagtgattgagtcaagggagaaaggcat ctagcctcggtctcaaaagggtagttgctgtctagagaggtctggtggag cctgcaaaagtccagcttttcaaaggaacacagaagtatgtgtatggaata ttagaagatgttgcttttactcttaagttggttcctaggaaaaatagtta aatactgtgactttaaaatgtgagagggtttttcaagtactcattttttta aatgtccaaaattttttgtcaatcaatttgaggtcttgtttgtgtagaact gacattacttaaagtttaaccgaggaatgggagtgaggctctctcatacc ctattcagaactgacttttaacaataataaattaagtttaaaatattttt aaatgaattgagcaatgttgagttgagtcaagatggccgatcagaaccgg aacacctgcagcagctggcaggaagcaggtcatgtggcaaggctatttgg ggaagggaaaataaaaccactaggtaaacttgtagctgtggtttgaagaa gtggttttgaaacactctgtccagccccaccaaaccgaaagtccaggctg agcaaaacaccacctgggtaatttgcatttctaaaataagttgaggattc agccgaaactggagaggtcctcttttaacttattgagttcaacctttaa ttttagcttgagtagttctagtttccccaaacttaagtttatcgacttct aaaatgtatttagaattcgagctcggtacagctttctggggcaggccagg cctgaccttggctttggggcagggaggggctaaggtgaggcaggtggcg ccagcaggtgcacacccaatgccatgagcccagacactggacgctgaac ctcgcggacagttaagaacccaggggcctctgcgcctgggcccagctctg tcccacaccgcggtcacatggcaccacctctcttgcagcctccaccaagg gcccatcggtcttccccctggcacctcctccaagagcacctctgggggc acagcggccctgggctgcctggtcaaggactacttccccgaaccggtgac ggtgtcgtggaactcaggcgccctgaccagcggcgtgcacaccttcccgg ctgtcctacagtcctcaggactctactccctcagcagcgtggtgaccgtg ccctccagcagcttgggcacccagacctacatctgcaacgtgaatcacaa gcccagcaacaccaaggtggacaagaaagttggtgagaggccagcacagg gagggagggtgtctgctggaagccaggctcagcgctcctgcctggacgca tcccggctatgcagccccagtccagggcagcaaggcaggccccgtctgcc tcttcacccggagcctctgcccgccccactcatgctcagggagagggtct tctggcttttttcccaggctctgggcaggcacaggctaggtgcccctaacc caggccctgcacacaaaggggcaggtgctgggctcagacctgccaagagc catatccgggaggaccctgcccctgacctaagcccaccccaaaggccaaa ctctccactccctcagctcggacaccttctctcctcccagattccagtaa ctcccaatcttctctctgcagagcccaaatcttgtgacaaaactcacaca tgcccaccgtgcccaggtaagccagcccaggcctcgccctccagctcaag gcgggacaggtgcctagagtagcctgcatccagggacaggccccagccg ggtgctgacacgtccacctccatctcttcctcagcacctgaactcctggg gggaccgtcagtcttcctcttcccccaaaacccaaggacaccctcatga tctcccggaccctgaggtcacatgcgtggtggtggacgtgagccacgaa gaccctgaggtcaagttcaactggtacgtggacggcgtggaggtgcataa tgccaagacaaagccgcggggaggagcagtacaacagcacgtaccgtgtgg tcagcgtcctcaccgtcctgcaccaggactggctgaatggcaaggagtac
aagtgcaaggtctccaacaaagccctcccagcccccatcgagaaaaccat
ctccaaagccaaaggtgggacccgtggggtgcgagggccacatggacaga
ggccggctcggcccacccctctgccctgagagtgaccgctgtaccaacctc
tgtccctacagggcagccccgagaaccacaggtgtacaccctgcccccat
cccgggatgagctgaccaagaaccaggtcagcctgacctgcctggtcaaa
ggcttctatcccagcgacatcgccgtggagtgggagagcaatgggcagcc
ggagaacaactacaagaccacgcctcccgtgctggactccgacggctcct
tcttcctctacagcaagctcaccgtggacaagagcaggtggcagcagggg
aacgtcttctcatgctccgtgatgcatgaggctctgcacaaccactacac
gcagaagagcctctccctgtccccgggcaaatga b) the light chain (SEQ ID NO: 24)
atggacatgagggtcctcgctcagctcctggggctcctgctgctctgttt
cccaggtaaggatggagaacactagcagtttactcagcccagggtgctca
gtactgcttactattcagggaaattctcttacaacatgattaattgtgt
ggacatttgttttatgtttccaatctcaggcgccagatgtgatatcgtg
ttgacgcagtctccagccaccctgtctttgtctccaggggaaagagccac
cctctcctgcgggccagtcagagtgttagcagcagctacttagcctggt
accagcagaaacctggccaggcgcccaggctcctcatctatggcgcatcc
agcagggccactggcgtgccagccaggttcagtggcagtgggtctgggac
agacttcactctcaccatcagcagcctggagcctgaagatttcgcgacct
attactgtctgcagatttacaacatgcctatcacgttcggccaagggacc
aaggtggaaatcaaacgtgagtagaatttaaactttgcggccgcctagac
gtttaagtgggagatttggagggatgaggaatgaaggaacttcaggata
gaaaagggctgaagtcaagttcagctcctaaaatggatgtgggagcaaac
tttgaagataaactgaatgacccagaggatgaaacagcgcagatcaaaga
ggggcctggagctctgagaagagaaggagactcatccgtgttgagtttcc
acaagtactgtcttgagttttgcaataaaagtgggatagcagagttgagt
gagccgtaggctgagttctctcttttgtctcctaagttttatgactaca
aaaatcagtagtatgtcctgaaataatcattaagctgtttgaaagtatga
ctgcttgccatgtagataccatgtcttgctgaatgatcagaagaggtgtg
actcttattctaaaatttgtcacaaaatgtcaaatgagagactctgtag
gaacgagtccttgacagacagctcaagggttttttttcctttgtctcatt
tctacatgaaagtaaatttgaaatgatcttttttattataagagtagaaa
tacagttgggtttgaactatatgttttaatggccacggttttgtaagaca
tttggtcctttgttttcccagttattactcgattgtaattttatatcgcc
agcaatggactgaaacggtccgcaacctcttctttacaactgggtgacct
cgcggctgtgccagccatttggcgttcaccctgccgctaagggccatgtg
aacccccgcgggtagcatcccttgctccgcgtggaccactttcctgaggca
cagtgataggaacagagccactaatctgaagagaacagagatgtgacaga
ctacactaatgtgagaaaaacaaggaaagggtgacttattggagatttca
gaaataaaatgcatttattattatattcccttatttaattttctattag
ggaattagaaagggcataaactgctttatccagtgttatattaaaagctt
aatgtatataatctttagaggtaaaatctacagccagcaaagtcatgg
taaatattctttgactgaactctcactaaactcctctaaattatatgtca
tattaactggttaaattaatataaatttgtgacatgaccttaactggtta
ggtaggatattttcttcatgcaaaaatatgactaataataatttagcac
aaaaatatttcccaatactttaattctgtgatagaaaatgtttaactca
gctactataatcccataatttgaaaactatttattagcttttgtgtttg
accctttccctagccaaaggcaactatttaaggaccctttaaaactcttga
aactactttagagtcattaagttatttaaccacttttaattactttaaaa
tgatgtcaattcccttttaactattaattttattttaaggggggaaaggct
gctcataattctattgttttcttggtaaagaactctcagttttcgtttt
tactacctctgtcacccaagagttggcatctcaacagagggactttccg
agaggccatctggcagttgcttaagatcagaagtgaagtctgccagttcc
tcccaggcaggtggcccagattacagttgacctgttctggtgtggctaaa
aattgtcccatgtggttacaaaccattagaccagggtctgatgaattgct
cagaatatttctggacacccaaatacagaccctggcttaaggccctgtcc
atacagtaggtttagcttggctacaccaaaggaagccatacagaggctaa
tatcagagtattcttggaagagacaggagaaaatgaaagccagtttctgc
tcttaccttatgtgcttgtgttcagactcccaaacatcaggagtgtcaga
taaactggtctgaatctctgtctgaagcatggaactgaaaagaatgtagt
ttcagggaagaaaggcaatagaaggaagcctgagaatacggatcaattct
aaactctgaggggggtcggatgacgtggccattctttgcctaaagcattga
gtttactgcaaggtcagaaaagcatgcaaagccctcagaatggctgcaaa
gagctccaacaaaacaatttagaactttattaaggaatagggggaagcta
ggaagaaactcaaaacatcaagattttaaatacgcttcttggtctccttg
ctataattatctgggataagcatgctgttttctgtctgtccctaacatgc
cctgtgattatccgcaaacaacacacccaagggcagaactttgttactta
aacaccatcctgtttgcttctttcctcaggaactgtggctgcaccatctg
tcttcatcttcccgccatctgatgagcagttgaaatctggaactgcctct
gttgtgtgcctgctgaataacttctatcccagagaggccaaagtacagtg
gaaggtggataacgccctccaatcgggtaactcccaggagagtgtcacag
agcaggacagcaaggacagcacctacagcctcagcagcaccctgacgctg
agcaaagcagactacgagaaacacaaagtctacgcctgcgaagtcaccca
tcagggcctgagctcgcccgtcacaaagagcttcaacaggggagagtgtt
ag

Example 1.1

Vector Construction

Figure 1B:
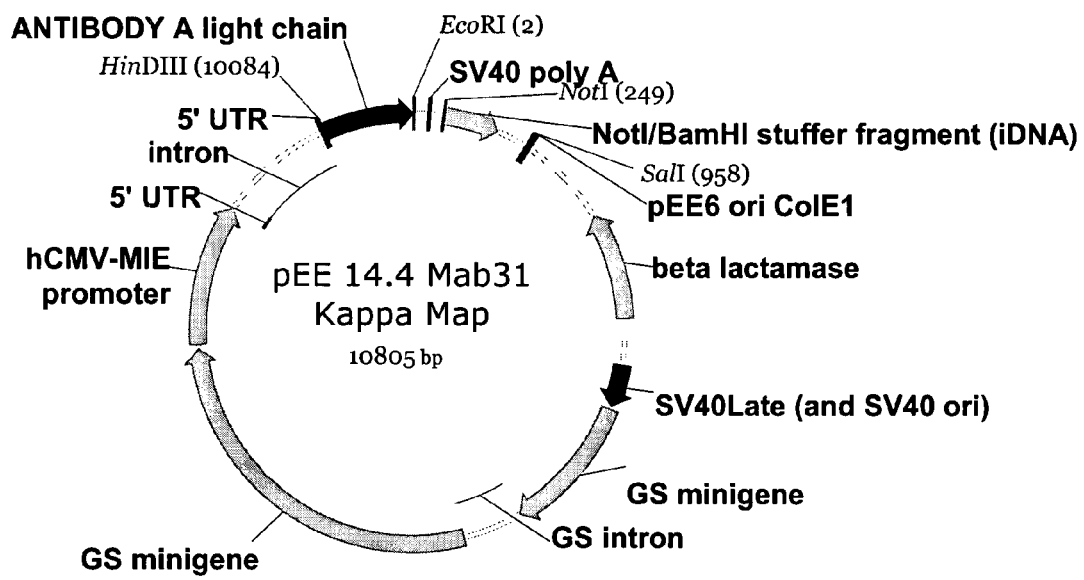
Figure 1C:
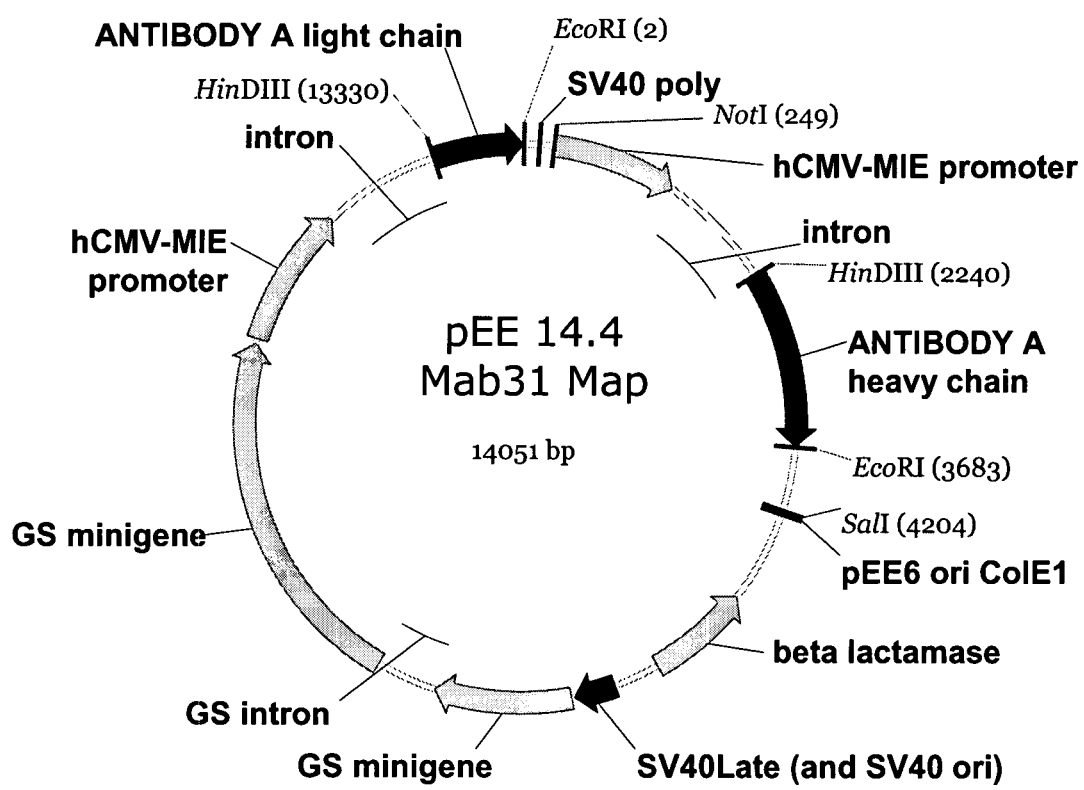

Sequences for ANTIBODY A originated from the 2nd maturation round after primary screening of the MorphoSys HuCAL Library, a synthetic phage display library. The DNA for ANTIBODY A was originally provided in vectors pMorph from MorphoSys, Germany and corresponds to Fab expressing vectors in FIG. 2 in WO 03/070760, appendix p 6/43. In the vector construction for the purposes of the present invention, vectors pEE6.1 and pEE 14.4 (both commercially available from Lonza Biologics are encoded to obtain a construct with both chains in one vector, see appended FIG. 1; see WO 87/04462 or WO 89/01036. The following cloning strategy was applied:

The Ig kappa chain was isolated from vector MS-Roche #7.9.H7_Ig_kappa chain (as described in WO 03/070760) by PCR with primer ACGTAAGCTTGCCGCCACCATGGT-GTTGCAG (sense, HindIII; SEQ ID NO. 29) and primer ACGTGAATTCCTAACACTCTCCCCTGTT (antisense, EcoRI; SEQ ID NO. 30), inserted into pCR 2.1 Topo TA and the insert was completely sequenced. The Ig kappa chain insert was removed from pCR Topo 2.1 by HinDIII/EcoRI digest and ligated into vector pEE14.4 as HindIII/EcoRI insert.

The Ig gamma 1 heavy chain was cloned from vector pMorph MS-Roche #7.9.H7_IgG1 by PCR with primer ACGTAAGCTTGCCGCCACCATGAAACACCTG (sense, HindIII; SEQ ID NO: 31) and primer ACGTGAATTCT-CATTTACCCGGAGACAG (antisense, EcoRI; SEQ ID NO: 32), inserted into pCR 2.1 Topo TA, and the insert was completely sequenced. The Ig gamma1 heavy chain insert was removed from pCR Topo 2.1 by HindIII/EcoRI digest and ligated into vector pEE 6.4 as HindIII/EcoRI insert. The heavy chain expression cassette was removed from pEE 6.4 IgG1 by NotI/SalI digest and the isolated fragment was inserted into SalI/NotI digested pEE14.4 kappa resulting in the final double-gene construct pEE 14.4 mAb-31.

Example 1.2

Transfection of CHO Cells and Expression of ANTIBODY A

Transfections were carried out according to standard protocols. The host cell line CHO K1 was derived from the Lonza Biologics working cell bank (WCB) #028-W2 (Lonza, 2002, 1-179) and the host cell line CHO K1 SV was derived from the Lonza Biologics master cell bank (MCB) #269-M (Lonza, 2003, 1-87).

Adherent CHO K1 cells derived from the WCB #028-W2 were transfected with the vector pEE 14.4 MAb31 containing both heavy and kappa light chain genes by liposomal transfection (Fugene, Roche Diagnostics). Transfection isolates were selected in DMEM, GS supplement (both JRH Biosciences), 10% dialysed FCS (PAA Laboratories, CoS#R0-CEP 2001-083-Rev 00) and 50 µM methionine sulphoximine (MSX from Sigma). 2 weeks later, colonies were picked and transferred to 96 well plates and tested with ELISA for antibody production. 4 colonies with the highest expression of ANTIBODY A were cloned by serial limited dilution to obtain single-cell derived cultures, of which 82 clones were derived after one week and expanded.

One of these clones was selected as the one with the highest specific production rate of 48 pg/cell/day in adherent state. It was further sub-cloned by limiting dilution to obtain the good producers expressing ANTIBODY A with high stability (Pu, (1998) Mol Biotechnol, 10, 17-25). Additionally, a suspension variant of the CHO K1 cells, the CHO K1 SV cells from MCB #269-M were transfected with the vector pEE 14.4 MAb31 by electroporation. Transfectants were selected as before and the resulting clones were subjected to single cell cloning by limiting dilution resulting in several high producer clones of ANTIBODY A.

Example 1.3

Adaptation of Clones Expressing ANTIBODY A to Suspension Culture

Best growth properties of CHO K1 clones were determined in DHI media with different protein hydrolysates: Cells were finally adapted to DHI media w/o glutamine (Invitrogen), which is a mixture of DMEM, Ham's F12 and IMDM in the respective proportions of 1:1:2 (v:v:v) (Schlaeger and Schumpp, 1992, J Immunol Methods, 146, 111-20) with the following modifications: soy and rice hydrolysate: 0.2% soy HyPep 1510 and 0.2% rice HyPep 5603 (Kerry Bioscience), 0.03% Pluronic F68 (Invitrogen), 25 µM MSX (Sigma) and 5% dialysed FCS (PAA Laboratories). FCS concentration was decreased gradually until cells did grow exponentially in serum-free media DHI media. Primary seed banks in serum-free DHI media were frozen for the several recombinant cell clones.

CHO K1 SV clones were adapted from DMEM containing 10% dialysed FCS to suspension culture in the chemically defined CD-CHO media with 25 µM MSX (Gibco-Invitrogen) in a two step procedure (Lonza). Cell banks were created in CD-CHO. Optionally, any other serum-free and protein-free media for CHO cells could be used for suspension culture and as a base for expressing the antibody.

Example 2

Production of ANTIBODY A

Production of ANTIBODY A (by Fed-Batch Fermentation)

CHO clones were prepared for fermentation from stock cultures in either shake flasks or spinner cultures as follows:

A cryo vial of the respective clones was thawed in the respective culture media containing 25 µM MSX in a 100 ml shake flask or spinner with a nominal volume of 50-75 ml.

Cells were then expanded in consecutive splits of 1:5 to reach a stock culture of 400-500 ml volume in either shake flasks or spinners. Cells used for inoculation of fermenters could be derived from these stock cultures up to 90 days after thawing. The seed train constitutes of a 2×1000 ml step in 2 L shake flasks or spinners, followed by inoculation of a 10 L fermenter as a further vessel. Alternatively, the 10 L fermenter could function as the fed-batch vessel itself or as inoculate for the 100 L fed-batch fermenter. MSX was present in the culture media for selection until the inoculation of the 10 L fermenter where it was excluded.

Fermentation Process:

Day 0: Start with 3-4×10$^5$/ml cells (1:4-1:5 split from seed culture)

Day 2-3: start of feeding, cell density should be above 1.5×10$^6$/ml.

Feeding: Continuous or bolus feed at 2% per day.

The isoform composition of ANTIBODY A was monitored throughout the fermentation by ion exchange chromatography (see below).

Day 14-18: When the viability of the cells started to drop (50%) and the expected titers were reached, the cell supernatant was harvested by centrifugation and/or filtration and filter-sterilised. It was stored aseptically and further processed as described in the next section.

The fermentation was carried out in accordance with standard protocols, see e.g. Werner, (1993), Arzneimittelforschung, 43, 1242-9 or Rendall, (2003). Proceedings of the 18th ESACT meeting, May 11-14, 2003, 1, 701-704).

Example 3

Purification of ANTIBODY A

The purification process was based on three chromatographic steps and a diafiltration step: Protein A affinity chromatography, cation exchange chromatography, anion exchange chromatography and diafiltration using a 100 kD membrane. The gel types and column sizes were 1 l MabSelect (GE Healthcare, Art. 17-5199, column diameter 9 cm, bed length 18+/−2 cm), 0.4 l CM-Toyopearl 650M (Toso Bioscience, Art. 007972, small ion capacity=85 microequivalents/ml, diameter 5.0 cm, bed length 20+/−2 cm), 1.3 l Q-Sepharose FF (GE Healthcare, Art. 17-0510-04), diameter 9 cm, bed length 20+/−2 cm. Columns were run at room temperature. Fractions were stored at 2-8° C. Detection was at 280 nm. A Biomax 100 ultrafiltration module with an area of 0.1 m² (Millipore Corp. Art. P2B100A01) was used for concentration and diafiltration.

Protein A Chromatography

The following solutions were prepared using purified water:
Solution A (equilibration buffer): 25 mM Tris, 25 mM NaCl, 5 mM EDTA, adjusted to pH 7.1+/0.1 by HCl
Solution B (washing buffer 1): 100 mM acetic acid adjusted to pH 4.5+/−0.1 by NaOH
Solution C (elution buffer): 100 mM acetic acid adjusted to pH 3.2+/−0.1 by NaOH
Solution D (washing buffer 2): 100 mM acetic acid, 75 mM NaCl, pH 3+/−0.1
Solution E: (regeneration buffer): 2 M guanidinium hydrochloride, 100 mM Tris, adjusted to pH 7.5+/−0.1 by HCl
Solution F (storage buffer): 200 mM benzyl alcohol, 100 mM acetic acid, adjusted to pH 5.0+/0.1 by sodium hydroxide The column was first equilibrated with 3 bed volumes of solution A In the following it was charged with the clarified cell culture supernatant (45 l, 386 mg/l antibody)
washed with 5 bed volumes of solution A,
washed with 3 bed volumes of solution B,
eluted with 3.5 bed volumes of solution C and the eluate was collected,
washed with 3 column volumes of solution D and
regenerated with 2 column volumes of solution E
equilibrated with 3 bed volumes of buffer A
and washed with bed volumes of buffer F for storage.

A linear flow rate of 100 cm/h was used for all chromatographic steps.

The column load was 17.4 g antibody/l Mabselect gel and the yield for the total mixture of isoforms was 96%.

Viral Inactivation

The following solution was prepared using purified water:
Solution G (adjusting solution): 2 M sodium acetate The pH of the protein A eluate was adjusted to a pH between 3.5 to 3.7 by addition of concentrated acetic acid or 2 M sodium acetate (solution G). It was stirred for 15 min and than adjusted to pH 4+/−0.1 by adding 2 M sodium acetate (solution G).

Cation Exchange Chromatography

The following solutions were prepared using purified water:
Solution H (equilibration buffer): 100 mM acetic acid, adjusted to pH 4.0+/−0.1 by NaOH
Solution I (elution buffer 1): 250 mM sodium acetate without pH-adjusting, pH 7.8-8.5
Solution J: (elution buffer 2): 500 mM sodium acetate without pH adjusting, pH 7.8-8.5
Solution K (regeneration solution): 0.5 M sodium hydroxide
Solution L (storage buffer): 0.01 M sodium hydroxide The column was first regenerated with 2 bed volumes of solution K and then equilibrated with 5 bed volumes of solution H.

In the following it was charged with an aliquot of the protein A eluate and washed with 1 bed volume of solution H.

Enclosed it was eluted with 6 bed volumes of solution I. In this step a mixture of the double-glycosylated and the mono-glycosylated isoforms eluted. In the next step 3 bed volumes of solution J were used to elute the non-glycosylated isoforms.

After use the column was regenerated with 2 bed volumes of solution K, stored for 24 h in this buffer and was then washed again with 2 bed volumes of solution K. For storing it was washed with 3 bed volumes of solution L.

Figure 3:
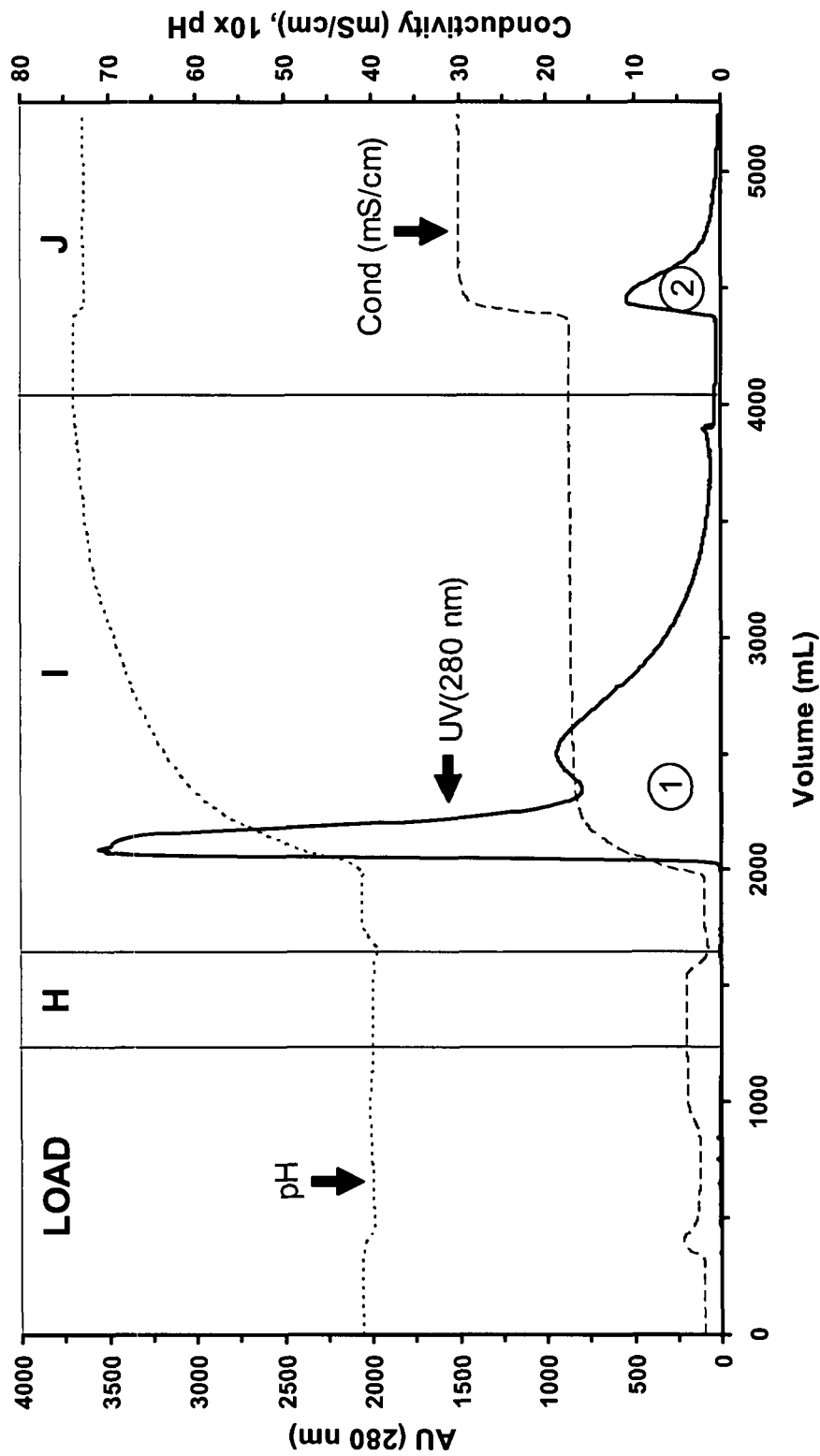
FIG. 3: Chromatogram of a CMT column as described in the text. Double-glycosylated and mono-glycosylated isoforms are eluting in double peak 1, the non-glycosylated isoform is eluting in peak 2

An example chromatogram is shown in FIG. 3.

Fractions of the chromatography were analyzed by analytical IEX as described below.

A linear flow rate of 100 cm/h was used for all chromatographic steps.

The column load was 14.3 g antibody/l CM-Toyopearl 650 M, and the yield was 79% for the mixture of double-glycosylated and mono-glycosylated isoforms and 6.2% for the non-glycosylated isoforms.

Flow Through Chromatography Using Q-Sepharose FF

The following solutions were prepared in purified water:
Solution M (dilution buffer): 37.5 mM Tris, adjusted to pH 7.9+/−0.1 by acetic acid
Solution N (adjusting solution): 2 M Tris
Solution O (equilibration buffer): 83 mM sodium acetate, 25 mM Tris, pH 7.5+/−0.1
Solution P (regeneration buffer 1): 0.5 M NaOH/1M NaCl
Solution Q (regeneration buffer 2): 0.2 M acetic acid/1 M NaCl
Solution R (storage buffer): 0.01 M NaOH The eluate from the CMT column (acidic) was first diluted 1:3 with solution M and then adjusted to pH 7.5 with solution N.

The column was first equilibrated with 2 bed volumes of solution O and in the following the diluted eluate from the CMT column was processed over the column and the flow through was collected. Product was washed off the column with solution with solution O until the absorption at 280 nm was lower than 0.1 (flow through collected).

The column was regenerated with 1.5 bed volumes of solution P, stored for 1 h and then regenerated with another 1.5 bed volumes of solution P. Then the column was regenerated with 2 bed volumes of solution Q and washed with 3 bed volumes of solution R and stored.

A linear flow rate of 100 cm/h was used for all chromatographic steps.

The column load was 3.5 g antibody/l Q Sepharose FF, and the yield was 91% for the mixture of double-glycosylated and mono-glycosylated isoforms.

Diafiltration

The following solution was prepared using purified water:
Solution S (diafiltration buffer): 20 mM Histidine, adjusted to pH 5.5 by HCl A filter holder Pellicon 2 (Millipore Corp.) was equipped with 1 ultrafiltration module type Biomax 100 (Millipore Corp., area=0.1 m², Art.P2B100A01). A WATSON-MARLOW 501 U pump equipped with a silicone tubing was used for pumping. The system was rinsed with buffer O and then 3.8 liters (1.1 g antibody/l) of the flow through from QS chromatography (adjusted tp pH 5.5 by concentrated acetic acid) were concentrated to 250-300 ml within 1 h at 4-11° C. In the following a diafiltration (V=const.) against 3 liters of buffer S (about 10 volumes) was performed (4-11°). Finally the product was sterile filtrated using a Millipac 20 filter (Millipore Corp.). The yield of the ultrafiltration/diafiltration step was 91%. The concentration of the product was 15 mg/ml. The product could be frozen at −70° C.

Analytical IEX Method for Analysis of Fractions
Column: Mono-S HR 5/5 (GE Healthcare, Art. 17-0547-01)
Buffer 1: 50 mM Morpholinoethansulfonic acid, adjusted to pH 5.8 by sodium hydroxide
Buffer 2: 50 mM Morpholinoethansulfonic acid, 1 M NaCl adjusted to pH 5.8 by sodium hydroxide
Flow rate: 1 ml/min
Detection: 280 nm
Sample load: 36-72μ
Gradient: Time % Buffer 2

|        |    |
|--------|----|
| 0 min  | 0  |
| 1      | 0  |
| 25     | 63 |
| 27     | 63 |
| 28     | 0  |
| 35     | 0  |

Figure 2:
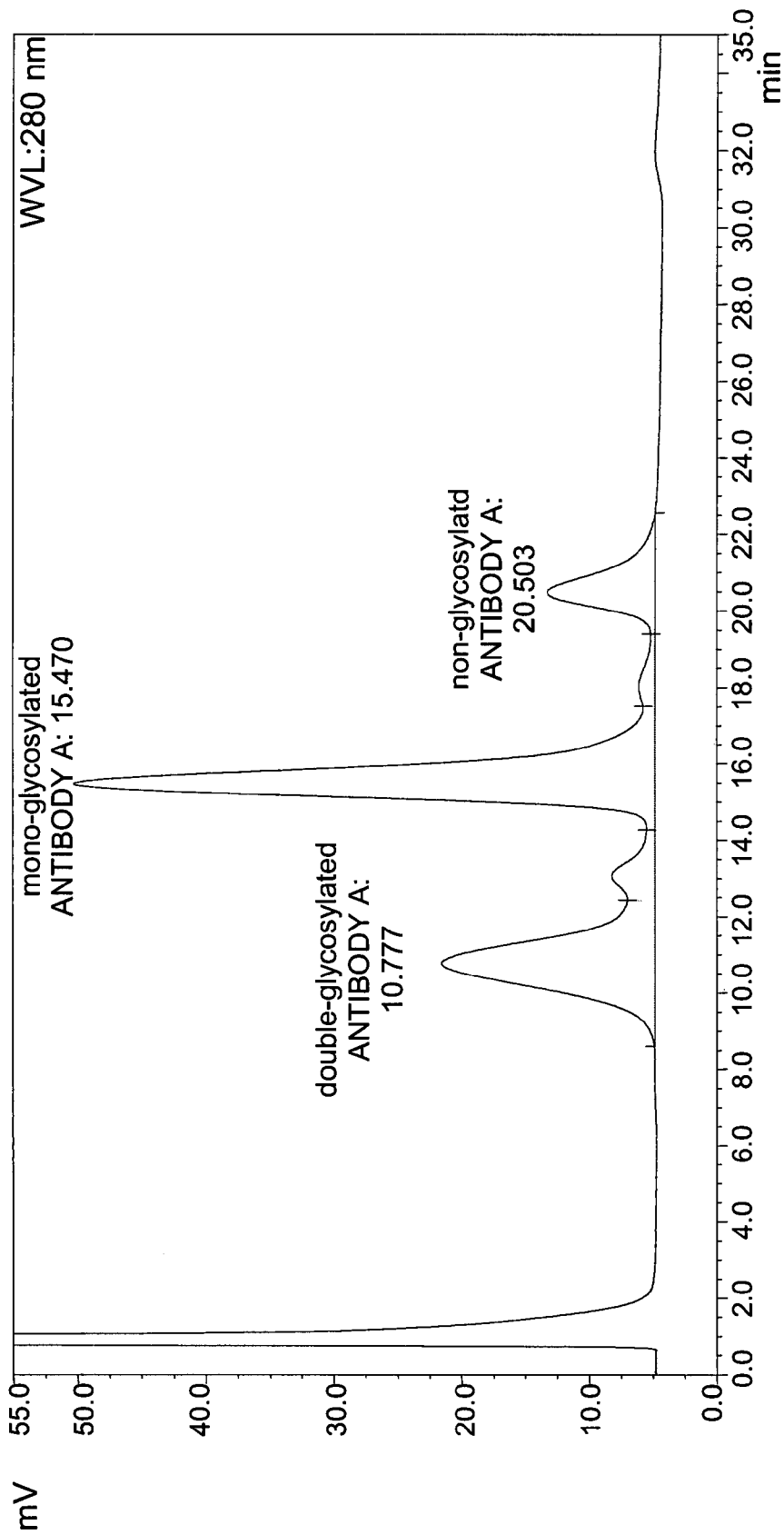
FIG. 2: Example of an analytical chromatogram

An exemplary chromatogram is given in FIG. 2

Yields

| Step | Isoform | Step yield |
|------|---------|------------|
| MabSelect (Protein A) | Mixture of all isoforms | 96% |
| CM-Toyopearl 650 M | Mixture of mono-glycosylated ANTIBODY A and double-glycosylated ANTIBODY A Content of non-glycosylated ANTIBODY A < 0.5% | 79% |
|  | Non-glycosylated ANTIBODY A | 6.2% |
| Q-Sepharose FF | Mixture of mono-glycosylated ANTIBODY A and double-glycosylated ANTIBODY A Content of non-glycosylated ANTIBODY A < 0.5% | 91% |
| Concentration and Diafiltration | Mixture of mono-glycosylated ANTIBODY A and double-glycosylated ANTIBODY A Content of non-glycosylated ANTIBODY A < 0.5% | 91% |

Example 4

Characterization of ANTIBODY A Isoforms by SDS-PAGE

SDS-PAGE analysis was carried out using standard protocols with 4-12% NuPage gradient Bis-Tris gel (Invitrogen) and marker MARK12 (Invitrogen) as control. 1-3 ug of ProteinA purified supernatants from fermentations (Prod 01, 02, 03) or spinner cultures (all other lanes) were loaded per well. The analysis under reducing conditions resulted in a single band for peak 1 (double-glycosylated ANTIBODY A), a double band for peak 2 (mono-glycosylated ANTIBODY A) and a single band for peak 3 (non-glycosylated ANTIBODY A) in the range of the molecular weight of the heavy chains. The molecular weights of the two bands of peak 2 corresponded to the molecular weights of peak 1 and peak 2, respectively.

Similar results were obtained employing several expression systems like: transient transfection in HEK 293 EBNA cells, transient transfection in CHO cells, and stable expression in CHO cells.

Example 5

Characterization of ANTIBODY A Isoforms by Mass Spectrometric (MS) Analysis

A complete antibody mass profile of all ANTIBODY A isoforms was determined by electron spray ionization mass spectroscopy (ESI-MS).

For this, samples of ANTIBODY A were prepared under non-reducing conditions. The samples were desalted into 2% formic acid and 40% acetonitril by G25 gel filtration and used for ESI-MS analysis in a Q-T of 2 or LCT-mass spectrometer instrument from Waters.

A separation by molecular mass is obtained with a difference of 1623 between non-glycosylated ANTIBODY A and mono-glycosylated ANTIBODY A. The expected mass for non-glycosylated ANTIBODY A from the amino acid sequence is 145,987 Da, which is in good agreement with the experimentally determined mass of 145,979 Da. Similarly, mono- and double-glycosylated ANTIBODY A isoforms differ by 1624 Da as indicated in FIG. 4. The observed differences in molecular masses are compatible with N-glycosylation patterns that are described in more detail herein below.

Example 6

Asn-52 Glycosylation Structure of ANTIBODY A

Asn52 is part of the sequence aaa-aaa-Asn-Ala-Ser-aaa-aaa of the variable part of the heavy chain, which corresponds to the N-glycosylation consensus sequence Asn-aaa-Ser/Thr. N-linked glycosylation of Asn52 was confirmed by tryptic peptide mapping of ANTIBODY A isoforms and mass spectrometric evaluation of peptide HC/T4 containing Asn52. In tryptic peptide maps of non-glycosylated ANTIBODY A, exclusively a peptide corresponding by mass to non-glycosylated HC/T4 peptide appears, indicating that Asn52 was not glycosylated, whereas in the mono- or double glycosylated ANTIBODY A peptides were detected corresponding by mass to HC/T4 containing N-linked sugar structures.

To further confirm glycosylation of the consensus sequence in the tryptic peptide HC/T4 of the heavy chain, the glycosylated HC/T4 peptide was isolated from peptide maps of glycosylated ANTIBODY A isoforms and analysed by MALDI-mass spectrometry before and after incubation with N-glycosidase F. Before N-Glycosidase F treatment, masses were obtained corresponding to HC/T4 peptide containing N-linked sugar structures. However, the mass of HC/T4 peptide treated with N-Glycosidase F corresponded to the mass expected to non-glycosylated HC/T4+1 Da, as expected if a sugar chain was removed from the asparagine by N-Glycosidase F (Asn to Asp-conversion).

The presence of N-acetyl-neuraminic acids at the sugar structures attached to Asn52, furthermore, indicates the presence of N-linked complex and hybride type sugar structures. For this, glycosylated ANTIBODY A isoforms were treated with N-Glycosidase F, which removes N-sugar at Asn306, but not at Asn52 and with or without Neuraminidase and analysed after separation of HC and LC by denaturation and reduction and desalting. The masses obtained for the HC from both approaches differed by about 291 Da or 582 Da corresponding to one or 2 sialic acids. From this, it also was concluded that N-linked sugars of the complex and/or hybride type were attached to Asn52.

This Asn-52 glycosylation, an N-glycosylation, predominantly consisted of sugar structures of the biantennary complex type (≥75%; mainly 80-90%) without core fucosylation and highly sialidated with up to 80% of the complex type antennae containing N-acetyl-neuraminic acids. Minor sugar structures belonged to the biantennary hybrid and the oligomannose type (≤25%), respectively (FIG. 5 or FIG. 27). Common to all Asn52 glycosylation structures was the resistance to cleavage by N-glycosidase F from intact ANTIBODY A.

Example 7

Asn306 Glycosylation Structure of ANTIBODY A

As pointed out above, ANTIBODY A contained attached to asparagine 306 (Asn306) in the Fc-part of the heavy chain (HC) an antibody type glycosylation consisting of a complex biantennary oligosaccharide chain. It is well known that antibodies contain different isoforms of such a complex bi-antennenary oligosaccharide chain, varying in the degree of terminal galactosylation, sialyation and in the degree of core fucosylation. In addition it is known that the degree of lacking core fucosylation in the Fc-located sugar chain is important for in vivo efficacy of antibodies, as it is well accepted that the degree of core fucosylation modulates effector functions of antibodies.

For ANTIBODY A major, antibody typical variations (Routier (1997), Glyoconjugate 14(2), 201-207; Raju (2003), BioProcess International, 44-52) in the Fc-located sugar chains attached to Asn306 were found regarding terminal galactosylation and core fucosylation.

Figure 6:
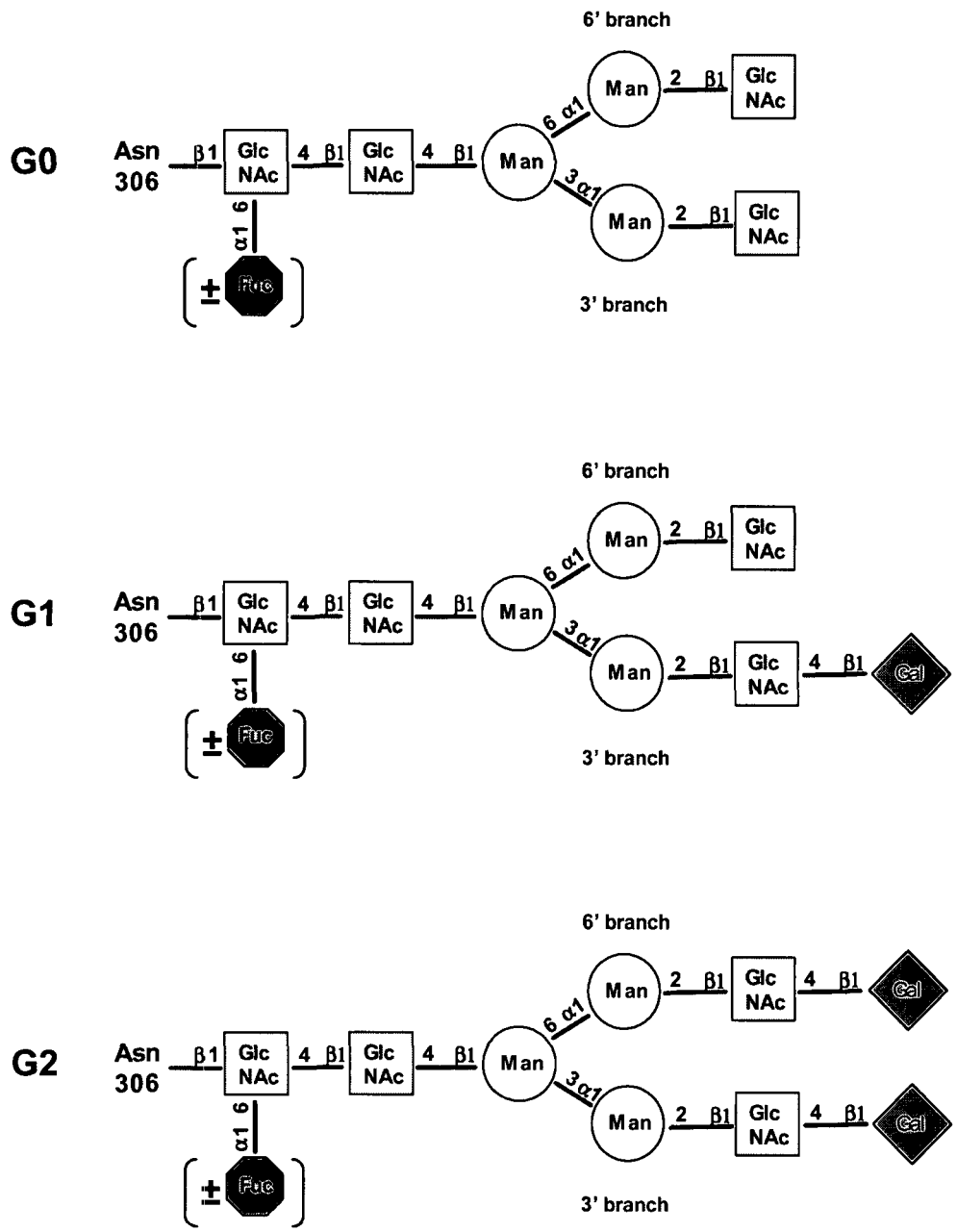
FIG. 6: Schematic presentation of carbohydrate structures at Asn306 of ANTIBODY A deduced from MS and HPAEC-PAD analysis. Structures that occur only partially are indicated by parenthesis. GlcNAc=N-acetyl-glucosamine, Man=mannose; Gal=galactose; Fuc=fucose; NeuAc=N-acetyl-neuraminic acid

The heterogeneity in the degree of terminal galactosylation (G0:G1:G2 structures) was determined to about 35-40% G0-structures, about 45% G1-structures and about 15-20% G2-structures (for schematic demonstration of the structures see FIG. 6 or FIG. 27).

The content of Fc-sugar structures lacking core fucosylation, i.e. lacking the fucose unit attached to the innermost N-acetyl-glucosamine of the core sugar structure, probably is important for an antibody, as the presence or absence of this fucose unit may modulate the binding of the antibody to Fc-receptors of effector cells, thereby influencing activity of these cells.

For ANTIBODY A the relative content of sugar chain isoforms lacking core fucosylation at Asn 306 was determined by two different methods, as described in the following:

A) Mass Spectrometry of Complete, Glycosylated HC:

Samples of ANTIBODY A were denatured and reduced into light chain (LC) and glycosylated HC in the presence of 6M guanidine-hydrochloride and 250 mM TCEP. The reduced samples were desalted into 2% formic acid and 40% acetonitrile and used for ESI-MS analysis in a Q-T of 2 or LCT-mass spectrometer instrument from Waters. From the m/z spectra obtained the relative content of the individual oligosaccharide isoforms were calculated by peak height of glycosylated HCs containing the individual oligosaccharide isoforms from selected single m/z states. For calculation of the relative content of sugar structures lacking core fucosylation, peak height of G0-structure lacking core fucose (G0-Fuc) related to the sum of G0+(G0-Fuc).

The respective carbohydrate structures were assigned according to the differences of the masses obtained for glycosylated HC and for HC, whose oligosaccharide structures were removed by incubation with N-Glycosidase F prior to MS-analysis in control experiments.

B) Chromatographic Analysis of Released Oligosaccharides by HPEAC-PAD:

Samples of ANTIBODY A were incubated with N-Glycosidase F in sodium phosphate buffer at pH 7.2 in order to release the oligosaccharide chains from Asn306 (the sugar structures at Asn52 were not removed from the intact, non-denatured antibody under the conditions used). The released sugar chains were separated from the ANTIBODY A protein by centrifugation filtration and were analysed on a Carbo Pac PA200 column from Dionex in a BioLC system, using a sodium acetate gradient at strong alkaline pH (pH, 13). The column used was capable of resolving non-fucosylated from fucosylated oligosaccharide chains. Assignment of the individual peaks obtained to respective carbohydrate structures was done by comparing the retention times to the ones of suitable oligosaccharide standards analysed on the Carbo Pac PA200 column and by determining the molar mass of the peaks separated and collected by MALDI mass spectrometry, respectively. For calculation of the relative content of sugar structures lacking core fucosylation, the sum of area-% of all structures lacking core fucose was formed.

The analysis of several batches (combinations of double- and mono-glycosylated ANTIBODY A isoforms) and of purified ANTIBODY A isoforms, respectively, revealed that the content of non-fucosylated Asn306 linked oligosaccharide chains was in the range of ~14%-27% (measured by MS) and 6%-26% (measured by HPAEC-PAD), respectively.

Example 8

Determination of $K_D$ Values for ANTIBODY A COMPOSITION and Isoforms (e.g. Non-, Mono- or Double-Glycosylated Antibody of the Invention) Binding to Aβ1-40 and Aβ1-42 Fibers In Vitro by Surface Plasmon Resonance (SPR)

Binding of ANTIBODY A to fibrillar Aβ was measured online by surface plasmon resonance (SPR), and the affinities of the molecular interactions were determined as follows: Biacore2000 and Biacore3000 instruments were used for these measurements. Aβ1-40 and Aβ1-42 fibers were generated in vitro by incubation of synthetic peptides at a concentration of 200 μg/ml in 10 mM Na-acetate buffer (pH 4.0) for three days at 37° C. Electron microscopic analysis confirmed a fibrillar structure for both peptides, Aβ1-40 showing predominantly shorter (<1 micron) and Aβ1-42 predominantly longer (>1 micron) fibers. These fibers were assumed to represent aggregated Aβ peptides in human AD brain more closely than ill-defined mixtures of amorphous aggregates and unstructured precipitates. The fibers were diluted 1:10 and directly coupled to a CM5 as described in the Instruction Manual of the manufacturer (BIAapplication Handbook, version AB, Biacore AB, Uppsala, 1998).

This coupling procedure included an activation step, during which the carboxylic acid groups on the surface were transferred into chemically reactive succinimide ester groups by contacting the surface with an aqueous mixture of N-hydroxysuccinimide and 1-ethyl-1-(3-diaminopropyl)-carbodiimide hydrochloride, and an immobilization step, during which the activated surface was contacted with the fibres dissolved in 10 mM acetate buffer (pH 4.5) at 200-350 resonance units (1 resonance unit (RU) corresponds approximately to a surface loading of 1 picogram/mm$^2$). The fiber loaded surface was then contacted with the antibody solutions in the concentration range 200 nM≥C≥0.15 nM. Typical time dependent response curves (=sensograms) monitored during the association phase (during contact with buffer) and the dissociation phase (subsequent contact with buffer) are shown in FIG. 7.

The $K_D$ values for binding to Aβ1-40 and Aβ1-42 fibers of the ANTIBODY A isoforms are given in the table below. Briefly, $K_D$ values were calculated by Scatchard type analysis using concentration dependent equilibrium binding responses. These equilibrium binding constants could be obtained in two ways.

Figure 7:
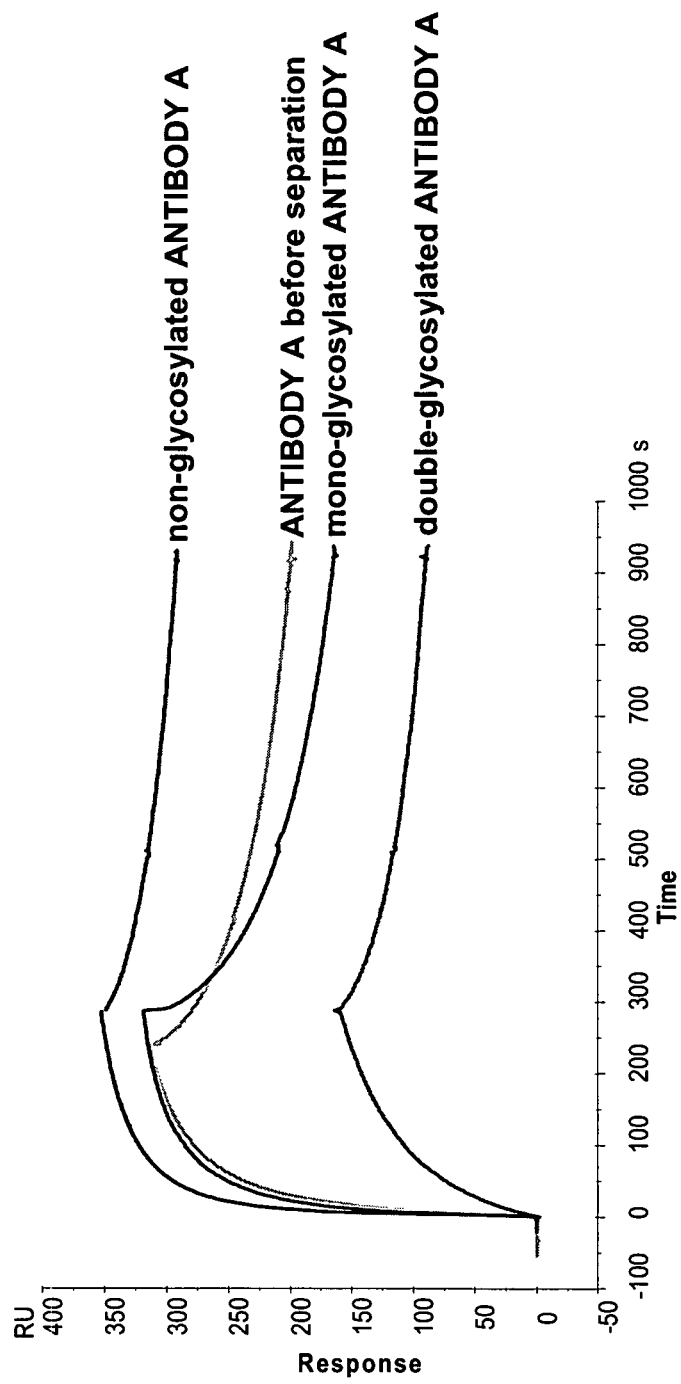
FIG. 7: Binding of ANTIBODY A isoforms to immobilized fibrillar Aβ40 (Biacore sensor chip). Antibody concentration 60 nM. Binding curve of a mixture of all isoforms, i.e. before purification is also shown as indicated.

Due to the very slow association process at low antibody concentration contact intervals to reach equilibrium were very long (FIG. 7). Nevertheless, such contact intervals could be realized on Biacore instruments and the experimental equilibrium responses could be subjected to a Scatchard analysis.

Equilibrium binding data were also obtained by extrapolating shorter time dependent association curves to infinity. These theoretically obtained equilibrium binding levels were then again used for the determination of the $K_D$ values.

Independently from the way of determining equilibrium sensor responses curvilinear Scatchard plots were obtained. From the curvilinear Scatchard plot a higher (bivalent) and lower (monovalent) affinity interaction was derived for ANTIBODY A isoforms derived from the second affinity maturation cycle. These two affinities represent the lower and upper $K_D$ values of the range indicated the following table:

|  |  | 1-40 high affinity $K_D$ values (nM) | 1-40 low affinity $K_D$ values (nM) |
| --- | --- | --- | --- |
| ANTIBODY A COMPOSITION (mixture of mono- and double-glycosylated ANTIBODY A) | extrapolation | 0.49 | 27.25 |
|  | stdev | 0.10 | 8.40 |
|  | equilibrium | 0.41 | 21.00 |
| double-glycosylated ANTIBODY A | extrapolation | 1.43 | 18.51 |
|  | stdev | 0.02 | 22.33 |
|  | equilibrium | 1.54 | 29.00 |
| mono-glycosylated ANTIBODY A | extrapolation | 0.25 | 7.55 |
|  | stdev | 0.02 | 2.06 |
|  | equilibrium | 0.12 | 11.10 |
| non-glycosylated ANTIBODY A | extrapolation | 0.19 | 1.99 |
|  | stdev | 0.03 | 0.15 |
|  | equilibrium | 0.42 | 2.82 |

The table above shows $K_D$ values of the low affinity complex (monovalent) and the high affinity complex (bivalent) formed by the interaction of ANTIBODY A isoforms and Aβ1-40 fibrils as determined by surface plasmon resonance. $K_D$ determined by using extrapolated equilibrium responses (marked "extrapolation") and KD values determined by using experimentally determined equilibrium responses (marked "experimental") are given. The extrapolated values were determined at least six times and a standard deviation is given. The $K_D$'s based on experimental and extrapolated equilibrium sensor responses are equal within the limits given by these standard deviations.

Example 9

Epitope Mapping of ANTIBODY A COMPOSITION and Isoforms (e.g. Non-, Mono- or Double-Glycosylated Antibody of the Invention) by Pepspot Analysis with Decapeptides An epitope (antigenic determinant) can be linear or conformational. The herein described dual epitope specificity was defined by reactivity of the antibody with two non-sequential linear peptides.

Epitope mapping approaches which were used to define specific epitope recognition are based on ELISA technology with hexapeptide conjugates coated on to microplates or on pepspot technology. The latter technology allows the detection and quantitation of the antibody by protocols that are commonly known for Western Blotting of proteins to PVDF membranes.

Applied epitope mapping technologies are designed to specifically detect linear epitopes, whereas they cannot be applied to map more spatially complex epitopes like discontinuous or conformational epitopes. Techniques available for conformational or discontinuous epitope mapping, like domain scanning and combinatorial peptide arrays require long peptides up to 36 amino acids (domains) or combined peptides each consisting of 12 amino acids.

The applied techniques are therefore considered to be specific for linear epitopes, excluding that conformational epitopes either discontinuous or discontinuously scattered epitopes are involved.

In conclusion, the presented data show that the two regions within the Aβ peptide defined herein resemble independent linear epitopes simultaneously recognized based on the unique dual epitope specificity of the investigated antibodies on single hexameric or decameric Aβ-peptides.

The following amino acid sequence encompassing Aβ (1-42) was divided into 43 overlapping decapeptides with a frameshift of 1 amino acid. The numbers refer to the essential amino acids from the Aβ1-40 sequence which have to be present in the decapeptide for optimal binding of antibody.

ISEVKM$^1$DAEF RHDSGYEVHH QKLVFFAEDV GSNKGAIIGL MVGGVVI$^{42}$ATV IV (SEQ ID NO: 4). Accordingly, DAEF RHDSGYEVHH QKLVFFAEDV GSNKGAIIGL MVGGVVIA (SEQ ID NO: 3) represents amino acids 1 to 42 of Aβ4/β-A4 peptide.

The 43 decapeptides were synthesized with N-terminal acetylation and C-terminal covalent attachment to a cellulose sheet ("pepspot") by a commercial supplier (Jerini BioTools, Berlin). The cellulose sheet was incubated for 2 hours on a rocking platform with monoclonal antibody (1 μg/ml) in blocking buffer (50 mM Tris.HCl, 140 mM NaCl, 5 mM NaEDTA, 0.05% NP40 (Fluka), 0.25% gelatin (Sigma), 1% bovine serum albumin fraction V (Sigma), pH 7.4). The sheet was washed 3 times 3 minutes on a rocking platform with TBS (10 mM Tris.HCl, 150 mM NaCl, pH 7.5). It was then pressed on filter paper, wetted with cathode buffer (25 mM Tris base, 40 mM 6-aminohexane acid, 0.01% SDS, 20% methanol) and transferred to a semi-dry blotting stack with the peptide side facing a PVDF membrane (Biorad) of equal size.

The semi-dry blotting stack consisted of freshly wetted filter papers (Whatman No. 3) slightly larger than the peptide sheet:
3 papers wetted with Cathode buffer
the peptide sheet
a sheet of PVDF membrane wetted with methanol
3 papers wetted with Anode buffer 1 (30 mM Tris base, 20% methanol)
3 papers wetted with Anode buffer 2 (0.3 mM Tris base, 20% methanol)

Figure 8A:
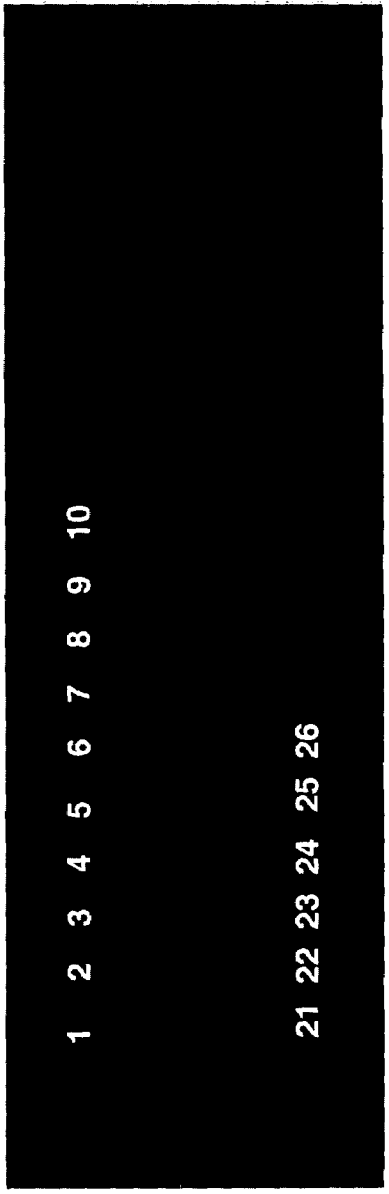
FIG. 8: Epitope mapping of ANTIBODY A COMPOSITION by pepspot analysis. A) pepspot signals of indicated single overlapping decapeptide spots: 1. ISEVKMDAEF (SEQ ID NO: 33); 2. SEVKMDAEFR (SEQ ID NO: 34); 3. EVKMDAEFRH (SEQ ID NO: 35); 4. VKMDAEFRHD (SEQ ID NO: 36); 5. KMDAEFRHDS (SEQ ID NO: 37); 6. MDAEFRHDS (SEQ ID NO: 38); 7. DAEFRHDSGY (SEQ ID NO: 39); 8. AEFRHDSGYE (SEQ ID NO: 40); 9. EFRHDSGYEV (SEQ ID NO: 41); 10. FRHDSGYEVH (SEQ ID NO: 42); 21. QKLVFFAEDV (SEQ ID NO: 43); 22. KLVFFAEDVG (SEQ ID NO: 44); 23. LVFFAEDVGS (SEQ ID NO: 45); 24. VFFAEDVGSN (SEQ ID NO: 46); 25. FFAEDVGSNK (SEQ ID NO: 47); 26. FAEDVGSNK (SEQ ID NO: 48). B) densitometric analysis of signal intensity of single overlapping decapeptide spots. The sequences of the decapeptides were: ISEVKMDAEF (SEQ ID NO: 33); SEVKMDAEFR (SEQ ID NO: 34); EVKMDAEFRH (SEQ ID NO: 35); VKMDAEFRHD (SEQ ID NO: 36); KMDAEFRHDS (SEQ ID NO: 37); MDAEFRHDS (SEQ ID NO: 38); DAEFRHDSGY (SEQ ID NO: 39); AEFRHDSGYE (SEQ ID NO: 40); EFRHDSGYEV (SEQ ID NO: 41); FRHDSGYEVH (SEQ ID NO: 42); RHDSGYEVHH (SEQ ID NO: 49); HDSGYEVHHQ (SEQ ID NO: 50); DSGYEVHHQK (SEQ ID NO: 51); SGYEVHHQKL (SEQ ID NO: 52); GYEVHHQKLV (SEQ ID NO: 53); YEVHHQKLVF (SEQ ID NO: 54); EVHHQKLVFF (SEQ ID NO: 55); VHHQKLVFFA (SEQ ID NO: 56); HHQKLVFFAE (SEQ ID NO: 57); HQKLVFFAED (SEQ ID NO: 58); QKLVFFAEDV (SEQ ID NO: 43); KLVFFAEDVG (SEQ ID NO: 44); LVFFAEDVGS (SEQ ID NO: 45); VFFAEDVGSN (SEQ ID NO: 46); FFAEDVGSNK (SEQ ID NO: 47); FAEDVGSNKG (SEQ ID NO: 59); AEDVGSNKGA (SEQ ID NO: 60); EDVGSNKGAI (SEQ ID NO: 61); DVGSNKGAII (SEQ ID NO: 62); VGSNKGAIIG (SEQ ID NO: 63); GSNKGAIIGL (SEQ ID NO: 64); SNKGAIIGLM (SEQ ID NO: 65); NKGAIIGLMV (SEQ ID NO: 66); KGAIIGLMVG (SEQ ID NO: 67); GAIIGLMVGG (SEQ ID NO: 68); AIIGLMVGGV (SEQ ID NO: 69); IIGLMVGGVV (SEQ ID NO: 70); IGLMVGGVVI (SEQ ID NO: 71); GLMVGGVVIA (SEQ ID NO: 72); LMVGGVVIAT (SEQ ID NO: 73); MVGGVVIATV (SEQ ID NO: 74); VGGVVIATVI (SEQ ID NO: 75); and VGGVVIATVIV (SEQ ID NO: 76).
Figure 8B:
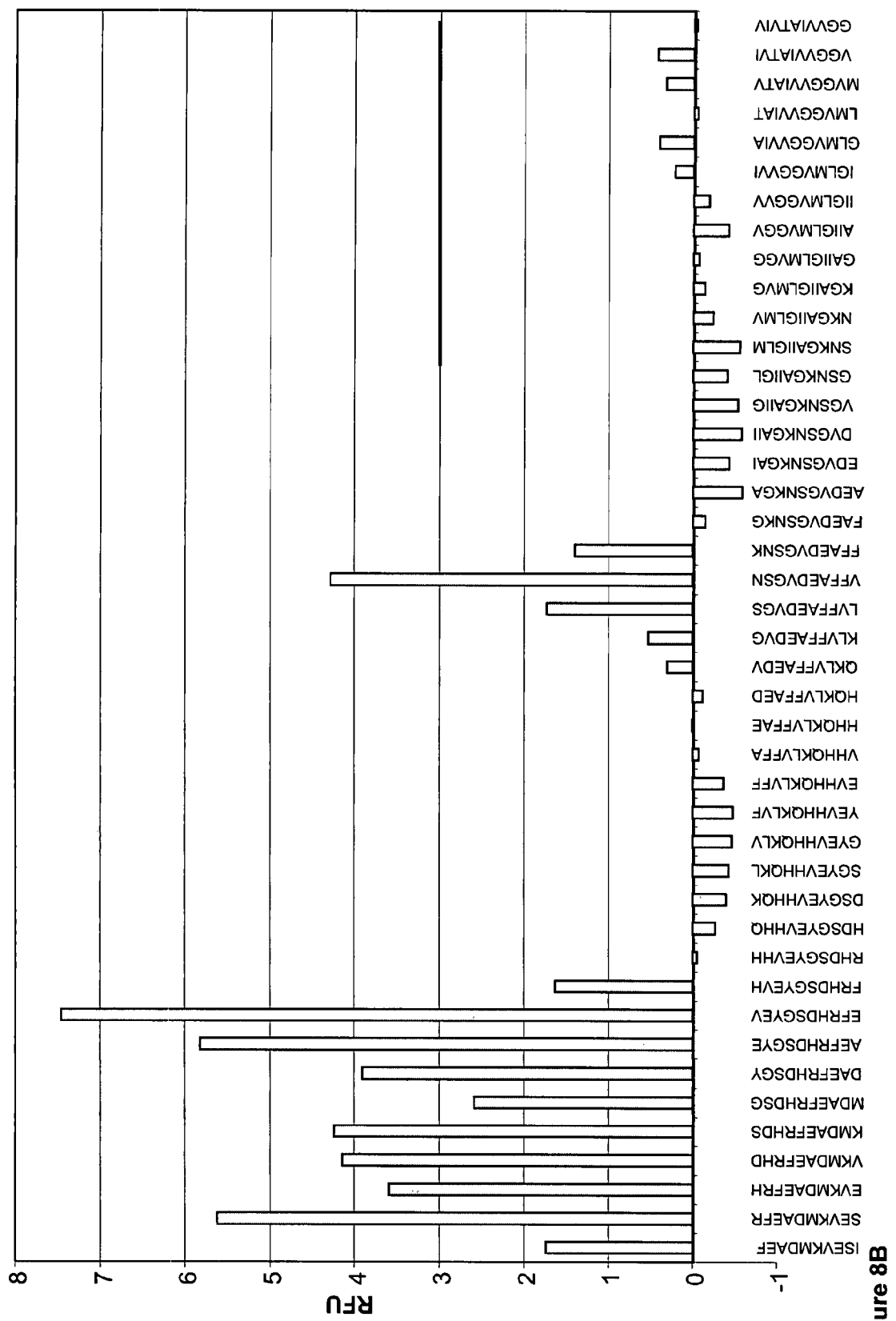

The transfer was conducted at a current density between Cathode and Anode of 0.8 mA/cm² for one hour which was sufficient to elute the antibody completely from the cellulose sheet and transfer it on the PVDF membrane. The PVDF membrane was immersed in blocking buffer for 10 minutes. Goat anti-human IgG(H+L) labeled with fluorochrome IRdye800 (Rockland code #609-132-123) was added at 1:10, 000 dilution in Odyssey blocking buffer (Li-Cor) and further diluted 1:1 with PBS, 0.05% Tween20. The membrane was incubated on a rocking platform for 1 hour. It was washed 3×10 minutes with TBST (TBS with 0.005% Tween20). The membrane was dried and scanned for 800 nm fluorescence using a long wavelength fluorescence scanner (Odyssey) as shown in FIG. 8.

The exact assignment of antibody-reactive spots was achieved by marking the PVDF membrane with a needle puncture. The epitopes of the antibody in question was defined as the minimal amino acid sequence in reactive peptides. The fluorescence intensity was integrated over each spot and recorded as relative fluorescence unit (RFU). For comparison two mouse monoclonal antibodies (BAP-1 which is equivalent to antibody 6E10 (Kim (1998).) with specificity for the N-terminal domain, and BAP-44 which is equivalent to antibody 4G8 (Kim (1998),) with specificity for the middle domain) were analyzed in the same way, except for using anti-mouse Ig instead of anti-human Ig for detection.

It is of note that affinity maturation and conversion of the monovalent Fab fragments into full-length IgG1 antibodies results usually in some broadening of the epitope recognition sequence as indicated by pepspot and ELISA analyses. This may be related to the recruitment of more contact points in the antibody-antigen interaction area as a consequence of the affinity maturation or to a stronger binding to the minimal epitope such that also weak interactions with adjacent amino acids can be detected. The latter may be the case when Aβ-derived peptides are probed with full-length IgG antibodies. As illustrated in the table below, the recognition sequences of the N-terminal and middle epitopes were extended by up to three amino acids when parent Fabs and corresponding fully maturated IgG antibodies were compared. However, it has to be kept in mind that the decapeptides were modified for covalent attachment at the C-terminal amino acid and this amino acid may therefore not easily be accessible to the full-length antibody due to steric hindrance. If this is the case the last C-terminal amino acid does not significantly contribute to the epitope recognition sequence and a potential reduction of the minimal recognition sequence by one amino acid at the C-terminal end has to be considered in the pepspot analysis as used in the present invention.

| antibody | Amino acid position | Amino acid position |
|---|---|---|
| double-glycosylated ANTIBODY A | 3-4 (1-10) | 18-24 (17-26) |
| mono-glycosylated ANTIBODY A | 4-5 (3-11) | 20-26 |
| non-glycosylated ANTIBODY A | 3-4 | 20-24 |
| ANTIBODY A COMPOSITION (Mixture of mono- and double-glycosylated ANTIBODY A isoforms (1:1)) | 3-5 (3-11) | 19-26 |
| BAP-44 (mouse monoclonal) | | 19-21 |
| BAP-1 (mouse monoclonal) | 4-6 | |

The table above relates to a pepspot analysis of binding full-length IgG antibodies to decapeptides on a cellulose sheet. The numbers refer to the amino acid position in the Aβ1-40 sequence which have to be present in the decapeptide for binding of antibody. A further extension to the epitope is indicated in brackets in order to indicate the flanking amino acids that are required to achieve maximum binding.

Example 10

De-Polymerization Assay Employing ANTIBODY A Isoforms (e.g. Non-, Mono- or Double-Glycosylated Antibody of the Invention) which Induces Release of Biotinylated Aβ from Aggregated Aβ

The experimental setup to test the potential of ANTIBODY A isoforms to induce dissociation of aggregated Aβ was as follows:
Biotinylated Aβ1-40 was first incorporated into preformed Aβ1-40/Aβ1-42 fibers before treatment with ANTIBODY A isoforms. Liberation of biotinylated Aβ was measured using an assay employing a streptavidin-POD conjugate as described below.

Synthetic Aβ when incubated in aqueous buffer over several days spontaneously aggregates and forms fibrillar structures which are similar to those seen in amyloid deposits in the brains of Alzheimer's Disease patients. The following in vitro assay is suitable to measure incorporation or liberation of biotinylated Aβ into preformed Aβ aggregates in order to analyze the Aβ-neutralizing potential of anti-Aβ antibodies and other Aβ-binding proteins such as albumin (Bohrmann (1999) J. Biol. Chem. 274, 15990-15995). ANTIBODY A isoforms induced de-polymerization of aggregated Aβ as measured by the release of incorporated biotinylated Aβ1-40.
Experimental Procedure:
NUNC Maxisorb microtiter plates (MTP) were coated with a 1:1 mixture of Aβ1-40 and Aβ1-42 (2 µM each, 100 µl per well) at 37° C. for three days. Under these conditions highly aggregated, fibrillar Aβ was adsorbed and immobilized on the surface of the well. The coating solution was then removed and the plates were dried at room temperature for 2-4 hours. The dried plates could be stored at −20° C. For incorporation of biotinylated Aβ the coated plates were incubated with 200 µl/well 20 nM biotinylated Aβ1-40 in TBS containing 0.05% NaN₃ at 37° C. overnight. After washing the plate with 3×300 µl/well T-PBS, antibodies serially diluted in TBS containing 0.05% NaN₃ were added and incubated at 37° C. for 3 hours. The plate was washed and analyzed for the presence of biotinylated Aβ1-40. After washing 3× with 300 µl T-PBS a streptavidin-POD conjugate (Roche Molecular Biochemicals), diluted 1:1000 in T-PBS containing 1% BSA, was added (100 µl/well) and incubated at room temperature for 2 hours. The wells were washed 3× with T-PBS and 100 µl/well of a freshly prepared tetramethylbenzidine (TMB) solution were added. [Preparation of the TMB solution: 10 ml 30 mM citric acid pH 4.1 (adjusted with KOH)+0.5 ml TMB (12 mg TMB in 1 ml acetone+9 ml methanol)+0.01 ml 35% $H_2O_2$]. The reaction was stopped by adding 100 µl/well 1 N $H_2SO_4$ and absorbance was read at 450 nm in a microtiter plate reader.

Figure 9:
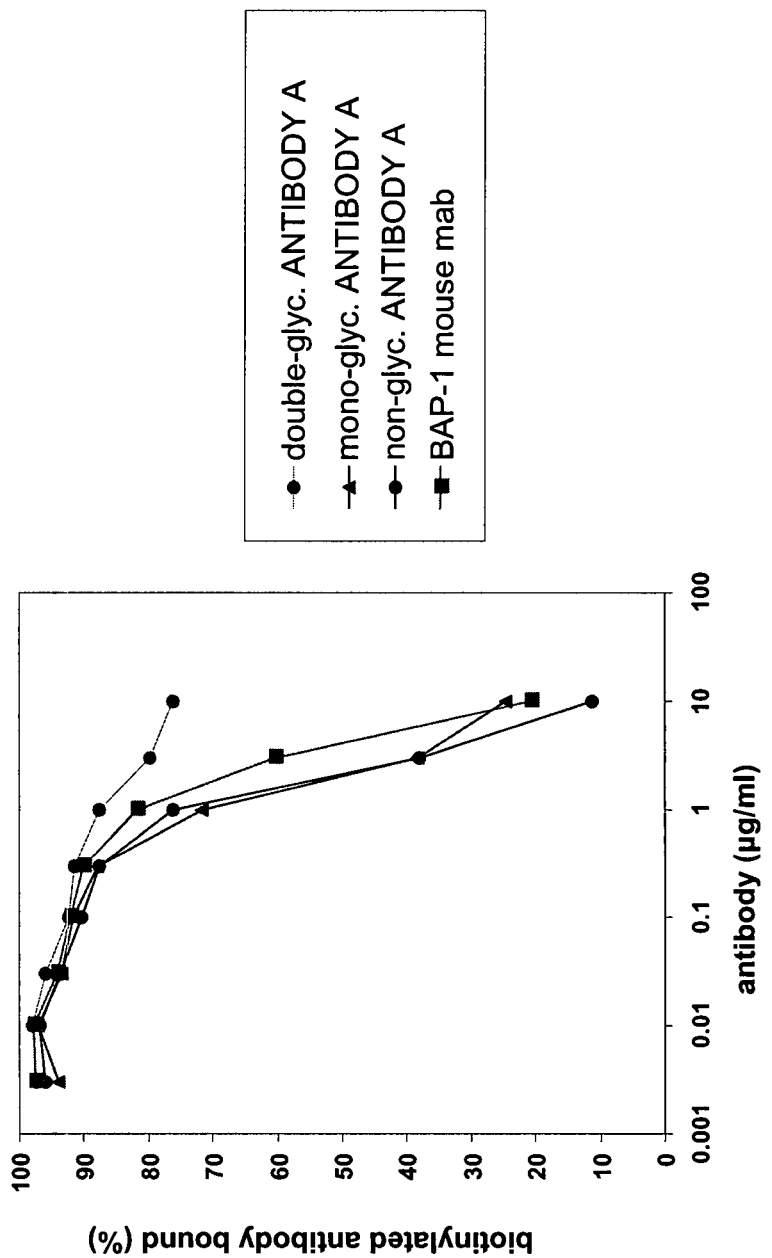
FIG. 9: De-polymerization Assay. ANTIBODY A COMPOSITION and ANTIBODY A isoforms induce release of biotinylated Aβ from aggregated Aβ

As documented in appended FIG. 9, ANTIBODY A isoforms induced dissociation of aggregated Aβ as measured by the release of incorporated biotinylated Aβ1-40. ANTIBODY A isoforms and the mouse monoclonal antibody BAP-1 were similarly active (FIG. 9), whereas the BAP-2, BAP-17 and 4G8 antibodies were clearly less efficient in liberating biotinylated Aβ from the bulk of immobilized Aβ (data not shown). BAP-1 could clearly be differentiated from the glycosylated ANTIBODY A isoforms by its reactivity with cell surface full-length APP. Antibodies like BAP-1 with such properties are not useful for therapeutic applications as potential autoimmunological reactions may be induced. It is interesting to note that BAP-2, despite its specificity for amino acid residue 4-6 which was exposed in aggregated Aβ has a clearly lower activity in this assay indicating that not all N-terminus specific antibodies a priori are equally efficient in releasing Aβ from preformed aggregates. The relatively low efficiency of BAP-17 (C-terminus-specific) and 4G8 (amino acid residues 16-24-specific) in this assay was due to the cryptic nature of these two epitopes in aggregated Aβ. BSA at the concentrations used here had no effect on aggregated Aβ.

The mono-glycosylated isoform exerted higher capacity compared to the double-glycosylated isoform to depolymerize aggregated Aβ peptide in vitro that may be relevant also in vivo.

Example 11

ANTIBODY A COMPOSITION and Comprising Isoforms (Mono- and Double-Glycosylated Antibody of the Invention) Capture Soluble Aβ from Human Cerebrospinal Fluid (CSF)

The capacity to capture soluble Aβ from human CSF samples was determined by immunoprecipitation (IP) and semi-quantitative Western blot (WB) analysis. Experimental procedure:

Immunoprecipitation of human CFS samples was done according to the following scheme:

| | |
|---|---|
| 70 ul | human CSF |
| 20 ul | Incubation buffer (50 mM Tris, 140 mM NaCl, 5 mM EDTA, 0.05% NP-40, 1% BSA, 0.25% Gelatin, 0.25% milk powder, pH 7.2 |
| 10 ul | ANTIBODY A isoforms from stock solutions (1000-10 ug/ml) |
| 100 ul | |

The solution was kept for one hour at 4° C. 40 ul protein G Sepharose beads (Amersham Biosciences #17-0618-01; washed with PBS, 50% slurry) were added and incubated for 2 hours at 4° C. on rotator. After centrifugation at 500 g for 3 minutes at 4° C. the supernatant was removed and 200 ul PBS were added to the beads, transferred to Millipore filter tubes 0.45 um (Millipore #UFC3OHVNB) and centrifuged at 500 g for 3 minutes at 4° C. Additional 200 ul PBS was added to beads, vortexed and centrifuged at 2000 g for 3 minutes at 4° C. 45 ul sample buffer 1× NuPage with DTT was added and kept for 10 minutes at 70° C. followed by centrifugation at 2000 g for 3 minutes at 4° C.

For SDS-PAGE, 18 ul protein G eluate was applied to NuPage gel 10% Bis-Tris gel together with $Aβ_{1-42}$ (Bachem) as internal standard directly in sample buffer as standard and run in MES buffer system.

The gel was transferred to Hybond C extra membrane (semi-dry system Novex) dry membrane 3' at room temperature. The membrane was transferred into pre-heated PBS and heated in microwave for 3 min. at 600 W. Blocking was done for 1 hour with SuperBlock Solution (Pierce) and additional blocking for 1 hour with 5% Milk Powder (Bio Rad) in T-PBS (0.1% Tween20 in PBS).

Incubation was done over night with anti Aβ antibody W02 Antibody (1:1500-1:2000 from The Genetics, Inc. Zürich, Switzerland) at 4° C. on a rotator, followed by washing 3× with T-PBS for 5 min and incubation for 2 hours at RT with anti-mouse IgG-HRP (Dako) 1:5000 in T-PBS. Another washing 3× with T-PBS for 5 min was followed by incubation with LumiLight Plus for 5 minutes at RT. Western blots were digitized and analysed by densometry with an Alpha Innotech Digital Camera System.

Figure 10:
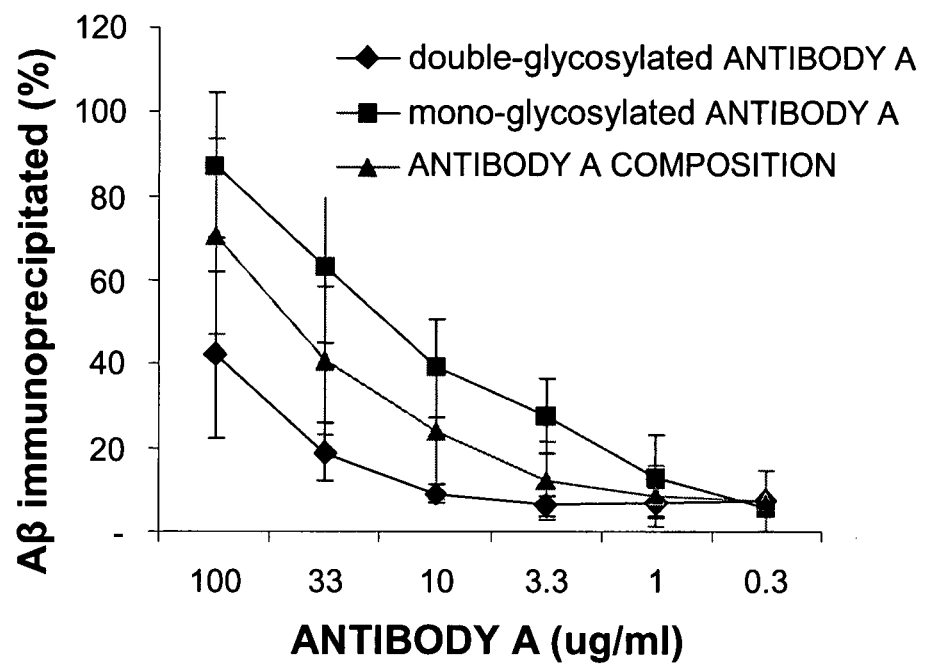
FIG. 10: ANTIBODY A COMPOSITION and comprising ANTIBODY A isoforms capture soluble Aβ from human cerebrospinal fluid (CSF). Average of 4 CSF samples from Alzheimer's disease patients analyzed in pools of 2. Two immunoprecipitations followed by Western blots per pool with quantification of captured Aβ by densitometry of Western blots. The highest Aβ value on a given series of Western blots was taken as 100%

As documented in FIG. 10, ANTIBODY A COMPOSITION (comprising mono- and double-glycosylated ANTIBODY A isoforms) bound efficiently to soluble Aβ in human CSF as demonstrated by immunoprecipitation and Western blotting experiments. Notably, in this assay, mono-glycosylated ANTIBODY A was more efficient in capturing soluble Aβ than double-glycosylated ANTIBODY A (FIG. 10).

Example 12

In Vitro Immunostaining of Human Amyloid Plaques by ANTIBODY A COMPOSITION and Isoforms (e.g. Non-, Mono- or Double-Glycosylated Antibody of the Invention)

Glycosylated ANTIBODY A isoforms were tested for the ability to stain genuine human β-amyloid plaques obtained from brain sections of patients with severe Alzheimer's Disease by immunohistochemistry analysis using indirect immunofluorescence. Specific and sensitive staining of genuine human β-amyloid plaques was demonstrated.

Cryostat sections of unfixed tissue from the temporal cortex obtained postmortem from a patient that was positively diagnosed for Alzheimer's disease were labeled by indirect immunofluorescence. A successive two-step incubation was used to detect bound ANTIBODY A isoforms, which were revealed by affinity-purified goat anti-human (GAH) IgG (H+L) conjugated to Cy3 (#109-165-003, lot 49353, Jackson Immuno Research). Controls included unrelated human IgG1 antibodies (Sigma) and the secondary antibody alone, which all gave negative results.

Figure 11:
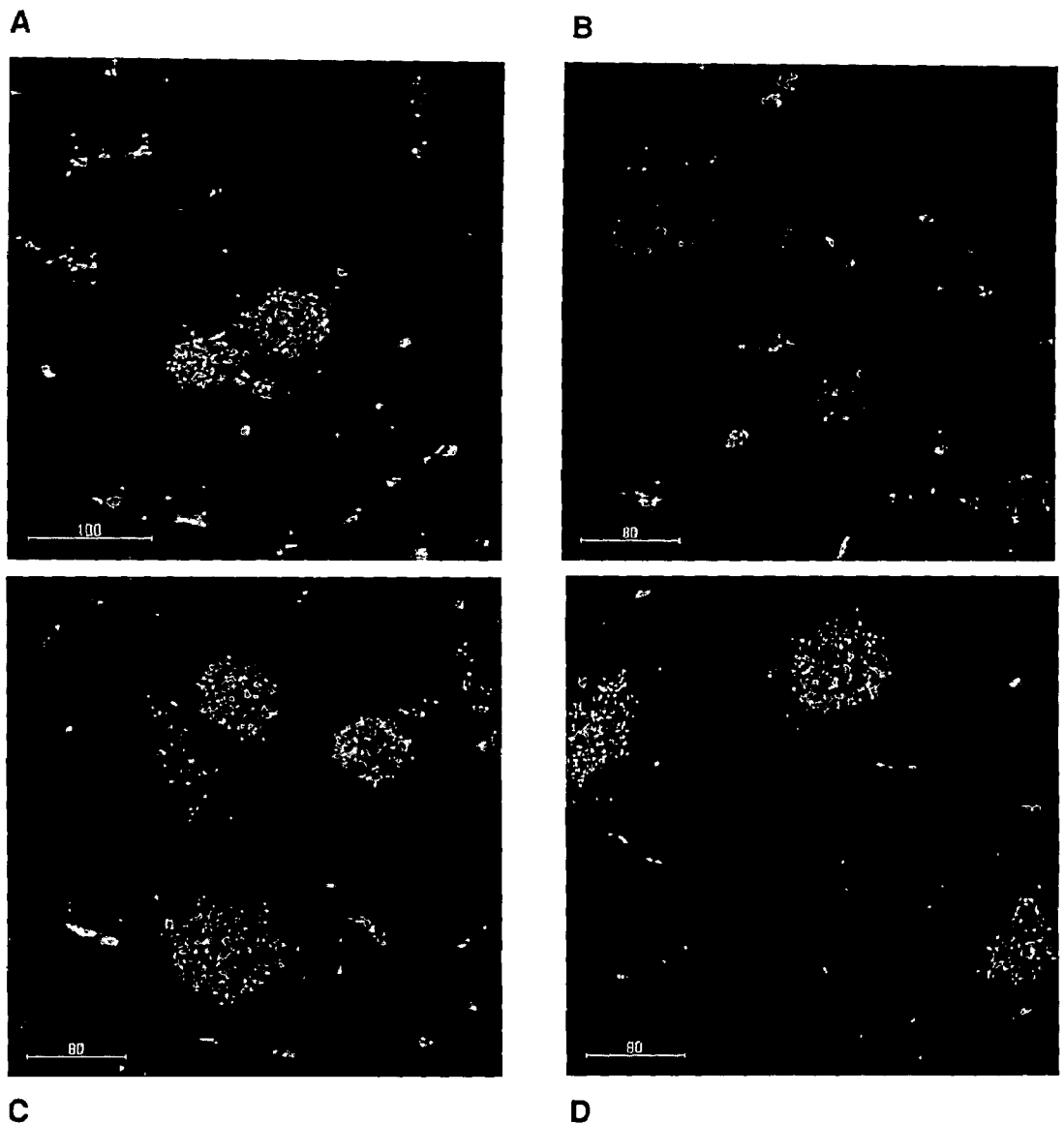
FIG. 11: Indirect immunofluorescence staining of human amyloid plaques with ANTIBODY A isoforms in vitro. Highly sensitive and specific detection of genuine ex vivo human β-amyloid plaques after staining with 10 ng/ml ANTIBODY A concentration. Bound ANTIBODY A was revealed by goat anti-human (H+L)-Cy3 for (A) ANTIBODY A COMPOSITION; (B) double-glycosylated ANTIBODY A; (C) mono-glycosylated ANTIBODY A; and (D) non-glycosylated ANTIBODY A. Scale bar=80 μm

All types of β-amyloid plaques were sensitively and specifically detected and consistently revealed at an ANTIBODY A concentration of 10 ng/ml (FIG. 11).

Specific and sensitive staining of genuine human amyloid-β plaques is demonstrated for the glycosylated ANTIBODY A isoforms at a concentration up to 1 µg/ml.

At a concentration of 10 µg/ml a background staining was observed, most prominent with the non-glycosylated ANTIBODY A isoform. The non-glycosylated isoform exerted considerable unspecific stickiness observed at the surface of glass slides and almost all tissue components that were exposed after the sectioning process in vitro. This appeared to be due to unspecific binding involving ionic and/or hydrophobic interactions.

Example 13

In Vivo β-Amyloid Plaque Decoration by ANTIBODY A in a Mouse Model of Alzheimer's Disease Glycosylated ANTIBODY A isoforms were tested in a single dose study in PS2APP double transgenic mice (Richards (2003), J. Neuroscience, 23, 8989-9003) for their ability to immuno-decorate β-amyloid plaques in vivo. The glycosylated ANTIBODY A isoforms were administered i.e. at a dose of 1 mg/mouse and after 3 days animals were perfused with phosphate-buffered saline and the brains frozen on dry ice and prepared for cryosectioning.

Both glycosylated isoforms showed improved and highly effective brain penetration in vivo (as compared to the non-glycosylated form). Effective brain penetration and specific binding to amyloid-β plaques was demonstrated in PS2APP mice, a mouse model for Aβ-related amyloidosis.

Figure 12:
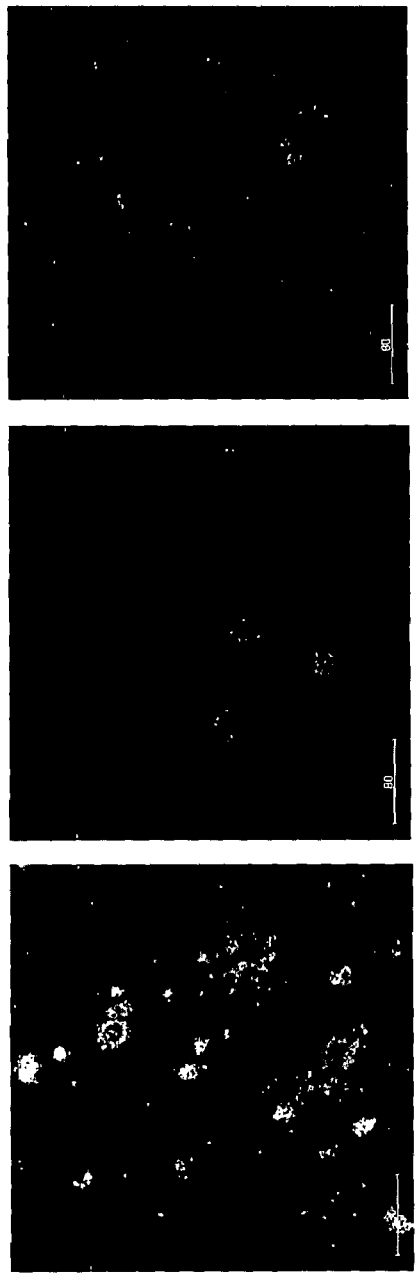
FIG. 12: In vivo immuno-decoration of PS2APP transgenic mouse plaques with glycosylated ANTIBODY A isoforms revealed by confocal microscopy. Immunodecoration reveals in vivo binding of ANTIBODY A isoforms 3 days after a single dose of 1 mg of ANTIBODY A isoforms. Representative images of the distribution of ANTIBODY A isoforms are shown for the double- (A), mono- (B), and non-glycosylated (C) ANTIBODY A isoform. Scale bar=80 μm

The presence of the antibodies bound to β-amyloid plaques was assessed using unfixed cryostat sections either by single-labeled indirect immunofluorescence with goat anti-human IgG (H+L) conjugated to Cy3 (#109-165-003, Jackson Immuno Research) shown in FIG. 12 or followed by counterstaining with BAP-2-Alexa488 immunoconjugate to visualize the position and distribution of all β-amyloid plaques types present in the tissue.

An immuno-fluorescence staining approach was used to detect bound ANTIBODY A. After adhesion to precooled glass slides, sections were hydrated in PBS and treated with 100% acetone precooled at −20° C. for 2 min. Washing with PBS was done twice for two minutes. Blocking of unspecific binding sites was done either with PBS containing 1% BSA or by sequential incubation in Ultra V block (LabVision) for 5 min followed by a PBS wash and incubation in power block solution (BioGenex) with 10% normal sheep serum for 20 min. After washing with PBS with 10% normal sheep serum slides were incubated with affinity-purified goat anti-human (GAH) IgG (H+L) conjugated to Cy3 (#109-165-003, lot 49353, Jackson Immuno Research) at a concentration of 15 µg/ml for 1 hour at room temperature. A counterstaining for amyloid plaques was by incubation with BAP-2, a mouse monoclonal antibody against Ab conjugated to Alexa 488 at a concentration of 0.5 µg/ml for 1 hour at room temperature. Autofluorescence of lipofuscin was quenched by incubation in 4 mM CuSO4 in 50 mM ammonium acetate. After rinsing the slides in bidistilled water and washing with 2×500 µl/slide PBS, slides were embedded with fluorescence mounting medium (S3023 Dako).

Imaging was done by confocal laser microscopy and image processing for quantitative analysis of colocalizations by IMARIS and COLOCALIZATION software (Bitplane, Switzerland).

After a single dose of 1 mg per mouse glycosylated ANTIBODY A isoforms were found to penetrate across the blood brain barrier and to effectively immuno-decorate/bind all β-amyloid plaques after three days in vivo. Representative images are shown in FIG. 12. This is in clear contrast to the non-glycosylated form which is not detectable at amyloid plaques.

Example 14

Figure 13:
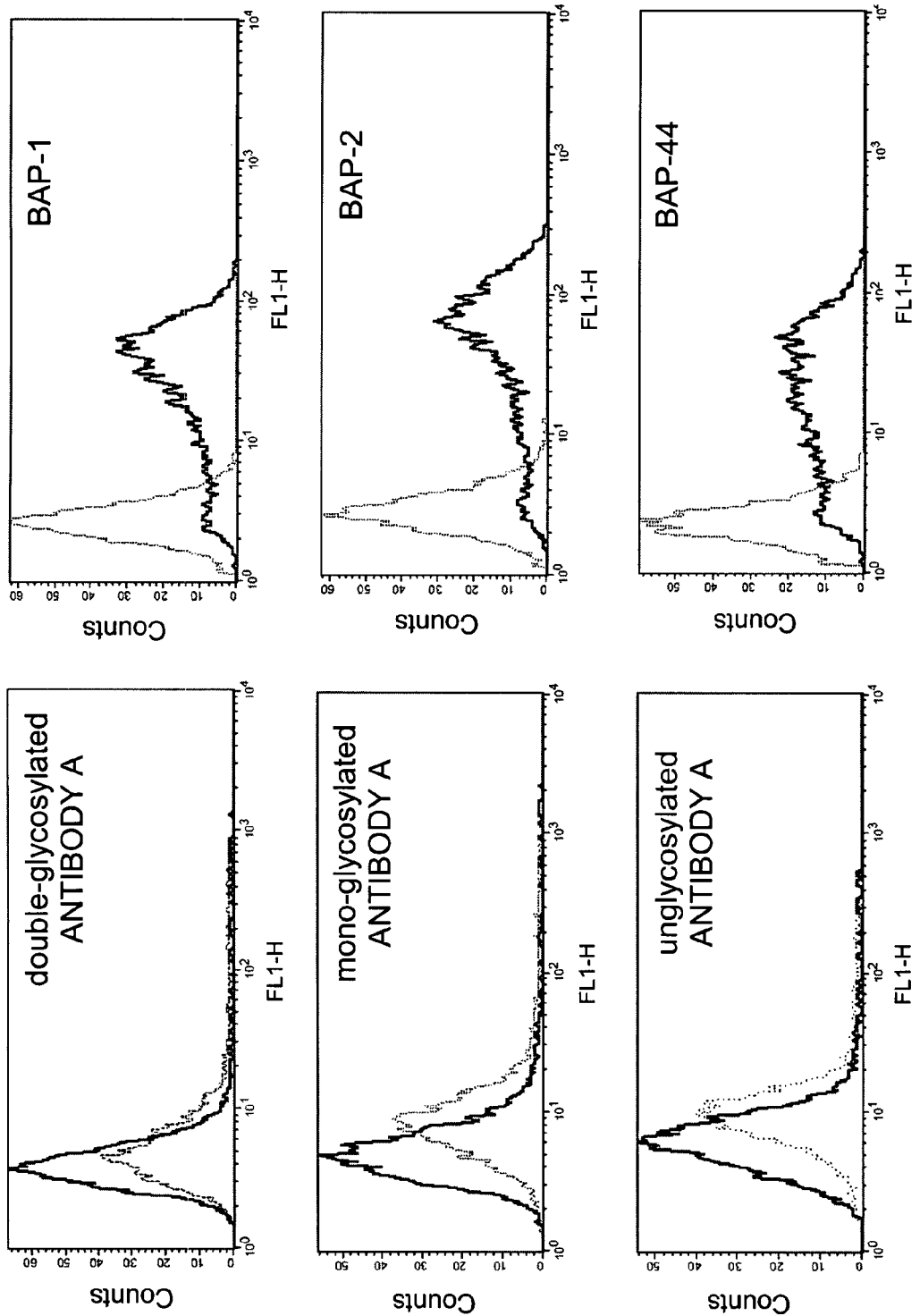
FIG. 13: Binding analysis of anti-Aβ antibodies to cell surface APP. Antibody binding to human APP-transfected HEK293 cells and non-transfected control cells analyzed by flow cytometry.
Figure 14:
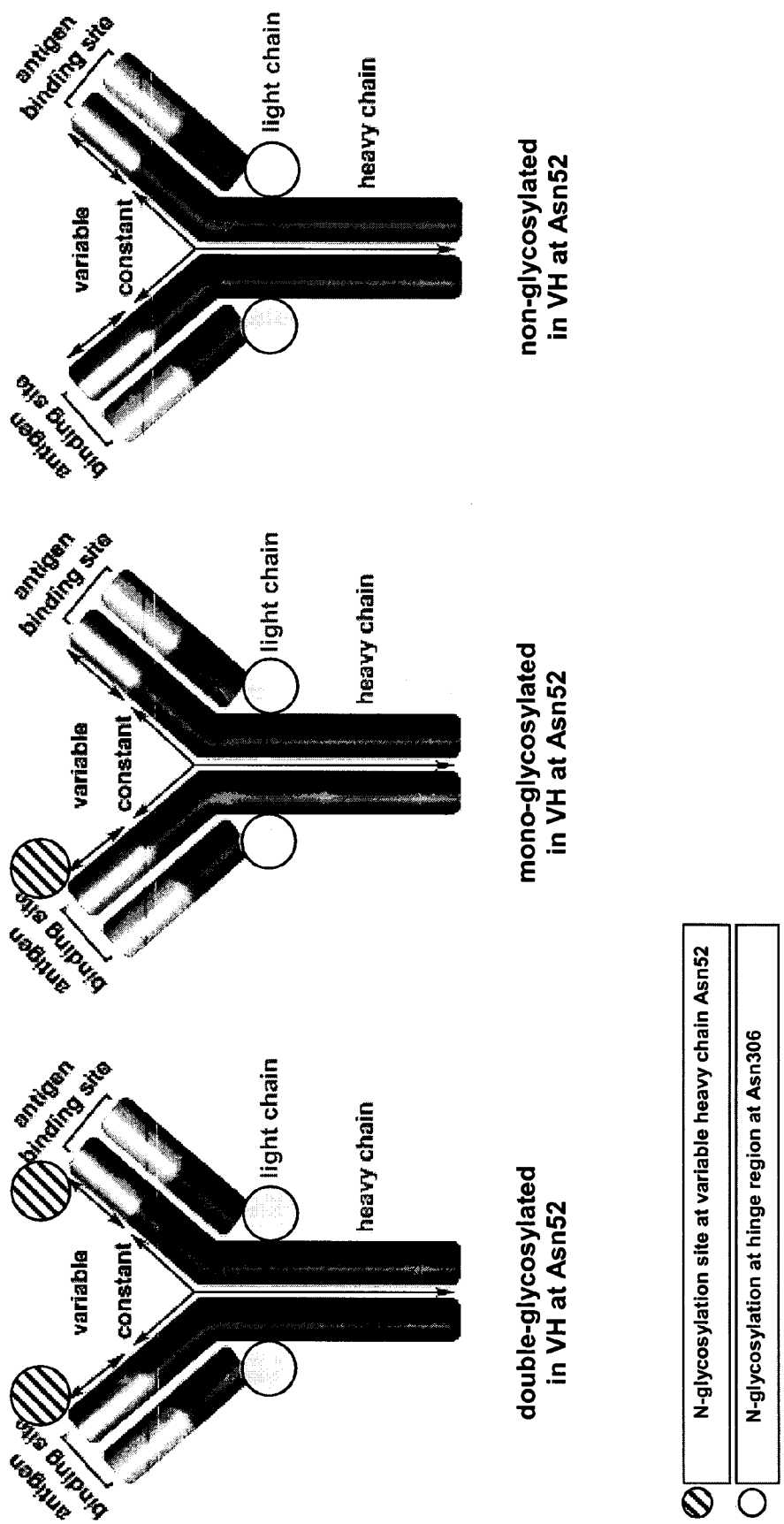
FIG. 14: Scheme of ANTIBODY A non-, mono- and double-glycosylated antibody molecules (immunoglobulins).

Investigation of Binding of ANTIBODY A Isoforms to Amyloid Precursor Protein (APP) Expressed on the Surface of HEK293 Cells The method of flow cytometry is well known in the art. Relative units of fluorescence (e.g. FL1-H) measured by flow cytometry indicated cell surface binding of the respective antibody. A fluorescence shift on APP transfected HEK293 compared to untransfected HEK293 cells indicated the unwanted reaction with cell surface APP. As an example, antibodies BAP-1 and BAP-2 against the N-terminal domain showed a significant shift of FL-1 signal in HEK293/APP (FIG. 13, thick line, right hand panel) compared to untransfected HEK293 cells (FIG. 13, dotted line, right hand panel). Similarly, BAP-44 antibody (specific for the middle A-beta epitope) showed a similar size shift. In contrast, all ANTIBODY A isoforms (FIG. 13 left hand panel) (specific for N-terminal and middle A-beta epitopes) showed no significant shift in fluorescence. The untransfected HEK293 cells had a higher basal fluorescence than the APP transfected cells due to different cell size and surface properties. A FACScan instrument was used in combination with the Cellquest Pro Software package (both Becton Dickinson).

ANTIBODY A isoforms were devoid of reactivity towards cell surface APP (FIG. 13).

Example 15

Morphometrical Analysis of Aβ Plaque Deposition in a Mouse Model of Alzheimer's Disease The capability of ANTIBODY A COMPOSITION or the ANTIBODY A isoforms to lower amyloidosis in vivo was studied in various brain regions (thalamus, neocortex, hippocampus and subiculum) using quantitative computer-assisted image analysis of brains of PS2APP mice that received a five-month treatment with ANTIBODY A COMPOSITION or ANTIBODY A isoforms.

Therefore, PS2APP transgenic male mice were injected i.v. with ANTIBODY A COMPOSITION or ANTIBODY A isoforms and vehicle. Seventy-five 5-6-month-old PS2APP mice were divided into five groups (A-E), consisting of 15 mice each. Beginning on day 0, each mouse received either 0.1 mL of vehicle (0 mg/kg), or ANTIBODY A preparations (20 mg/kg) by bolus i.v. injection via the tail vein. Groups A, B, C, D and E of PS2APP mice received vehicle (histidine-buffered saline), ANTIBODY A COMPOSITION which comprises mono-glycosylated ANTIBODY A and double-glycosylated ANTIBODY A and is devoid of non-glycosylated ANTIBODY A as defined above, double-glycosylated ANTIBODY A, mono-glycosylated ANTIBODY A and non-glycosylated ANTIBODY A, respectively.

Immunotolerance against the administered human anti-Aβ antibodies was induced by injecting anti-CD-4 antibody (hybridome clone GK 1.5 as commercially available from ATCC). Monitoring of anti-drug antibodies indicated that antibody treated animals only develop a moderate immune-response after more than 16 weeks of treatment and that the detectable antibodies are either of low affinity or are produced only in low amounts (data not shown).

After 5 month treatment mice were sacrificed. Unfixed brains were sectioned sagitally, including thalamus, hippocampal formation and cortical areas. From each brain hemisphere 50 sections were prepared is follows: Starting at lateral level ~1.92, 5 consecutive series of 5×10 µm and 5×20 µm sections were obtained. There was no gap between consecutive sections, resulting in a total tissue usage of 750 µm. The section series therefore ends approximately on lateral level 1.20 (Paxinos and Franklin, 2003). For quantitative morphometrical analysis every 10th section was used.

Sections were stained for amyloid deposits with the double-glycosylated ANTIBODY A isoform at a concentration of 5 µg/ml. Stainings against Aβ using a mouse monoclonal antibody (BAP-2) conjugated to Alexa-488 fluorophore at 5 µg/ml showed comparable results although with significant intracellular and background staining of neurons which interfered with the image processing routine described below. For detection an affinity-purified goat anti-human (GAH) IgG (H+L) conjugated to Cy3 (#109-165-003, lot 49353, Jackson Immuno Research) at a concentration of 15 µg/ml for 1 hour at room temperature was applied. After washing with 2×500 µl PBS/slide, slides were embedded with fluorescence mounting medium (S3023, Dako).

Images were acquired using a GenePix Personal 4100A microarray scanner (Axon Instruments, now Molecular Devices, CA, USA). Amyloid-β plaque load and number was measured using two parameters, namely percentage of area covered by amyloid-β plaques and number of amyloid-β plaques using an unbiased morphometrical method by means of computer assisted image analysis. Quantification of plaque load and number was done with MCID M7 Elite software (Imaging Research Inc., St. Catherines/Ontario, Canada). The scanned images were enhanced by a detail extractor filter followed by a target accent filter. The resulting image was then binarized, adjusting the threshold according to the staining intensity. Artefacts, blood vessels and edge effects were identified on the original reference image and then removed from the binarized image. Regions of interest were outlined on the reference image. For final quantification, the area of these regions and the area occupied by plaques as well as the plaque number were then measured in the binarized image. Single pixels were ignored. Calculations were made with common spreadsheet software (Microsoft Excel, Redmond/Wash., U.S.A.). The size of plaques was separated into 11 groups ranging from <100 to >1000 µm2. Statistical evaluation was done using a twotailed, heteroscedastic t-test.

For comparison and statistical evaluation, the baseline of amyloidosis (amyloid-β plaque pathology) was determined at study begin with a cohort (15 animals) of non-treated 6 month old PS2APP mice. Results are depicted in FIGS. 15 to 18 with levels of significance (*: $p \leq 0.05$; : $p \leq 0.01$; *: $p \leq 0.001$).

Figure 15A:
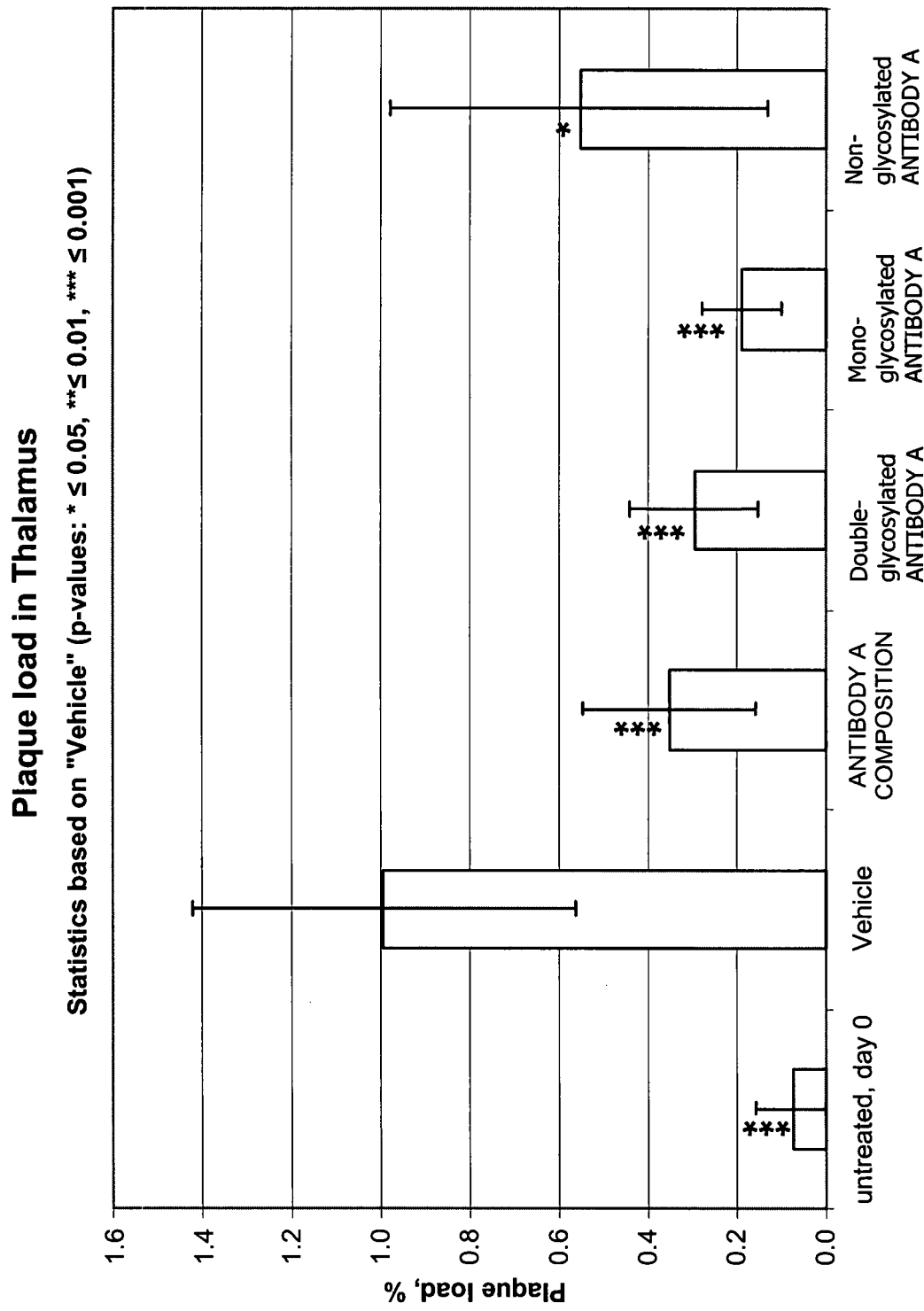
FIG. 15: Total plaque surface (A), total plaque number (B) and plaque number and size distribution (C) in the thalamus region after 5 month treatment with ANTIBODY A COMPOSITION (which comprises mono- and double-glycosylated ANTIBODY A), double-glycosylated and mono-glycosylated ANTIBODY A isoforms (20 mg/kg weekly, i.v.) or vehicle.
Figure 15B:
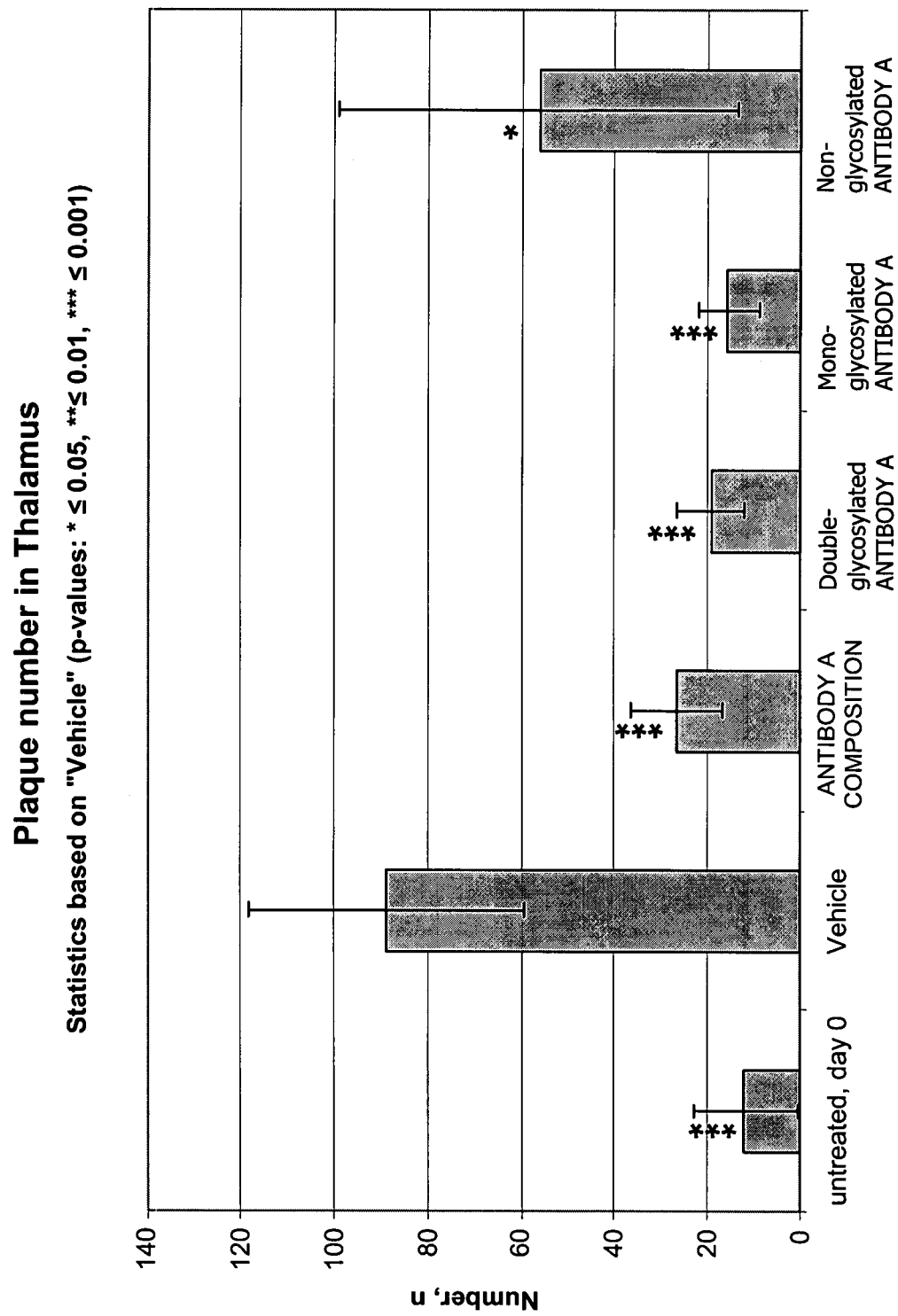
Figure 15C:
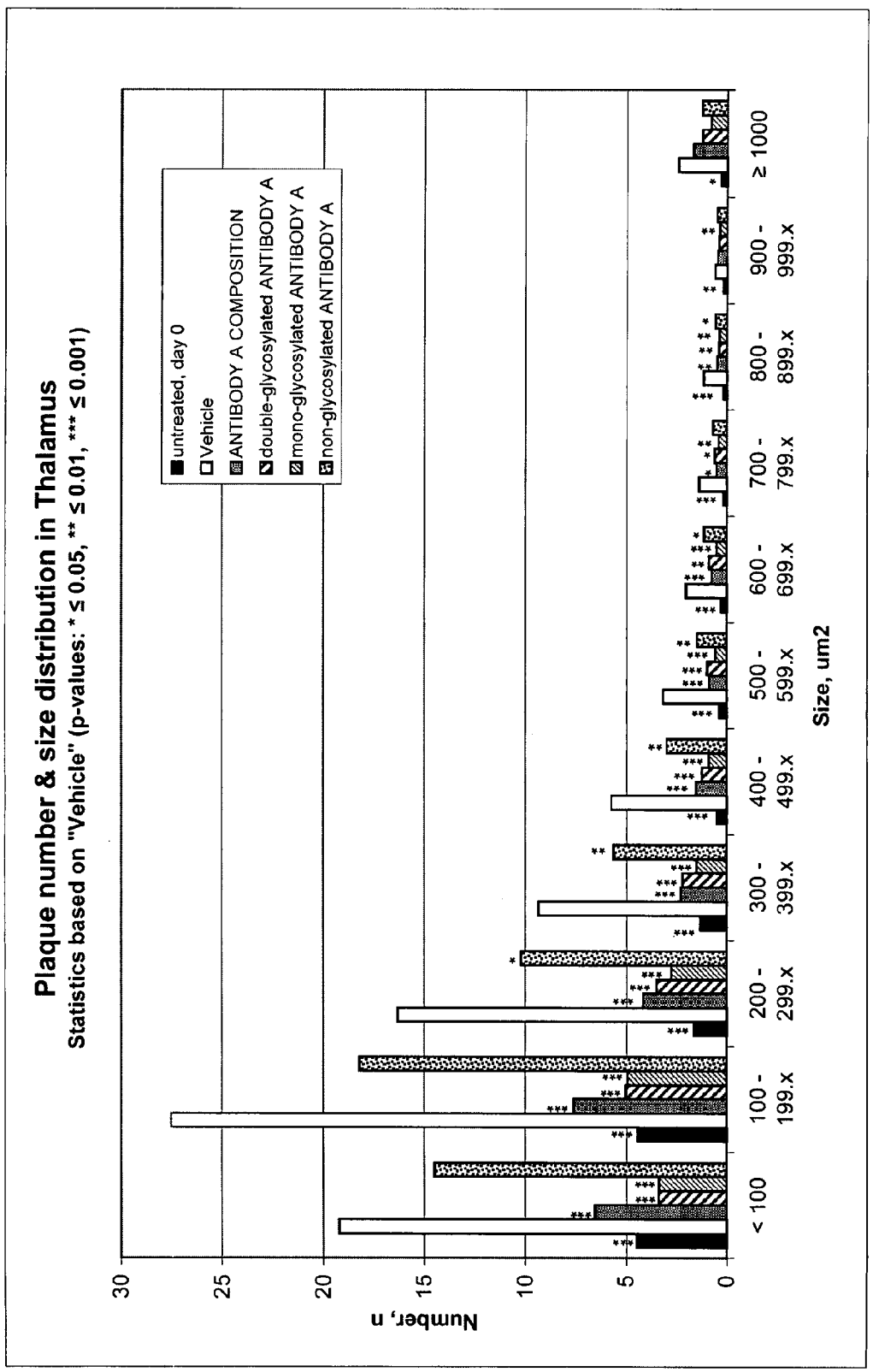

Amyloid plaque reduction was most pronounced in the thalamus region (FIG. 15). The mean reduction of total amyloid-β plaque surface was determined for the antibody treated groups: 64% for ANTIBODY A COMPOSITION, 70% for double-glycosylated ANTIBODY A, 81% for mono-glycosylated ANTIBODY A and 44% for non-glycosylated ANTIBODY A. The mean reduction in total amyloid-β plaque number was found to be 70% for ANTIBODY A COMPOSITION, 78% for double-glycosylated ANTIBODY A, 82% for mono-glycosylated ANTIBODY A and 36% for non-glycosylated ANTIBODY A. Note that significance for non-glycosylated ANTIBODY A was low and observed variations were considerable.

Figure 16A:
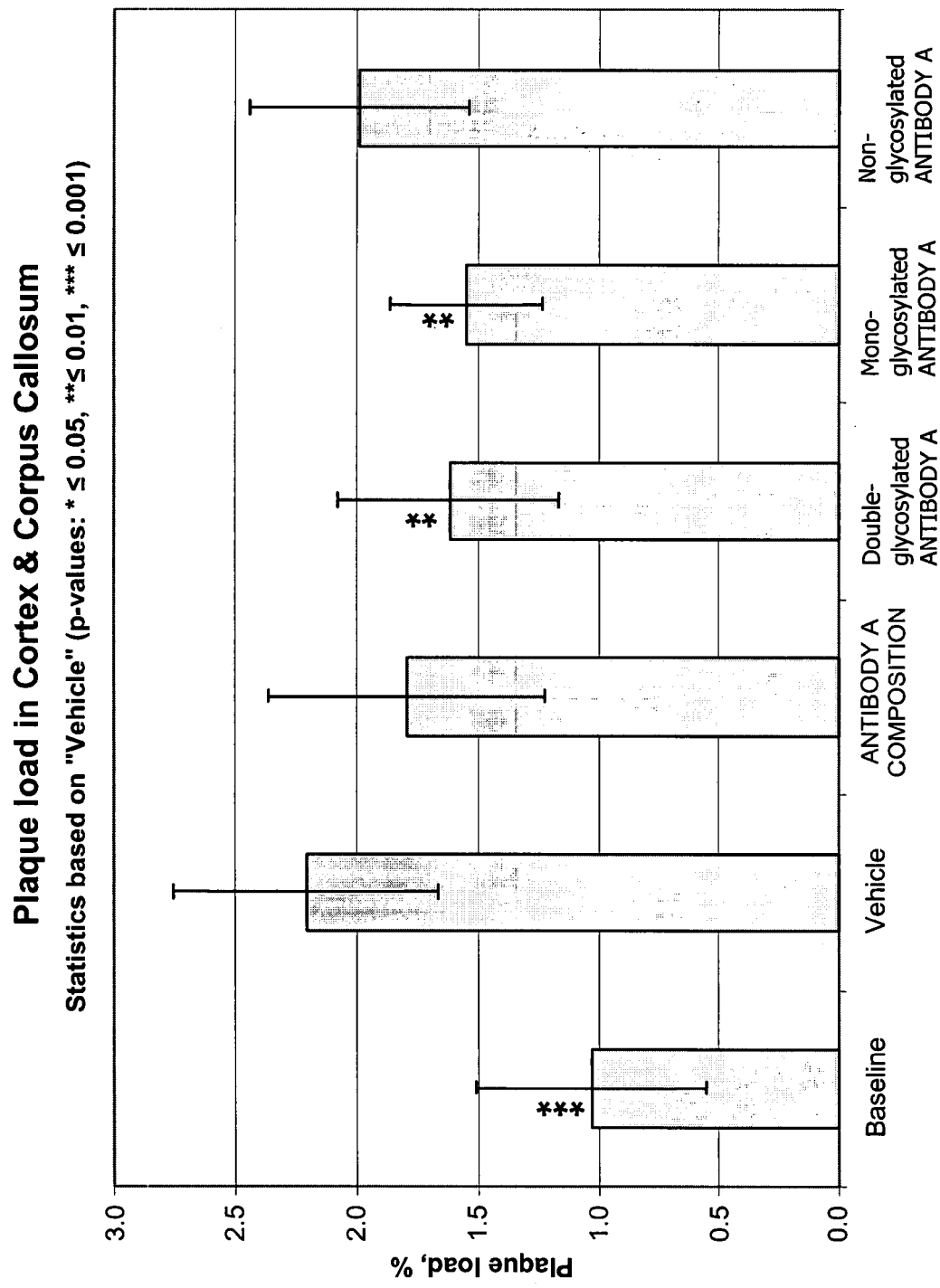
FIG. 16: Total plaque surface (A), total plaque number (B) and plaque number and size distribution (C) in the cortex and corpus callosum region after 5 month treatment with ANTIBODY A COMPOSITION (which comprises mono- and double-glycosylated ANTIBODY A), double-glycosylated and mono-glycosylated ANTIBODY A isoforms (20 mg/kg weekly, i.v.) or vehicle.
Figure 16B:
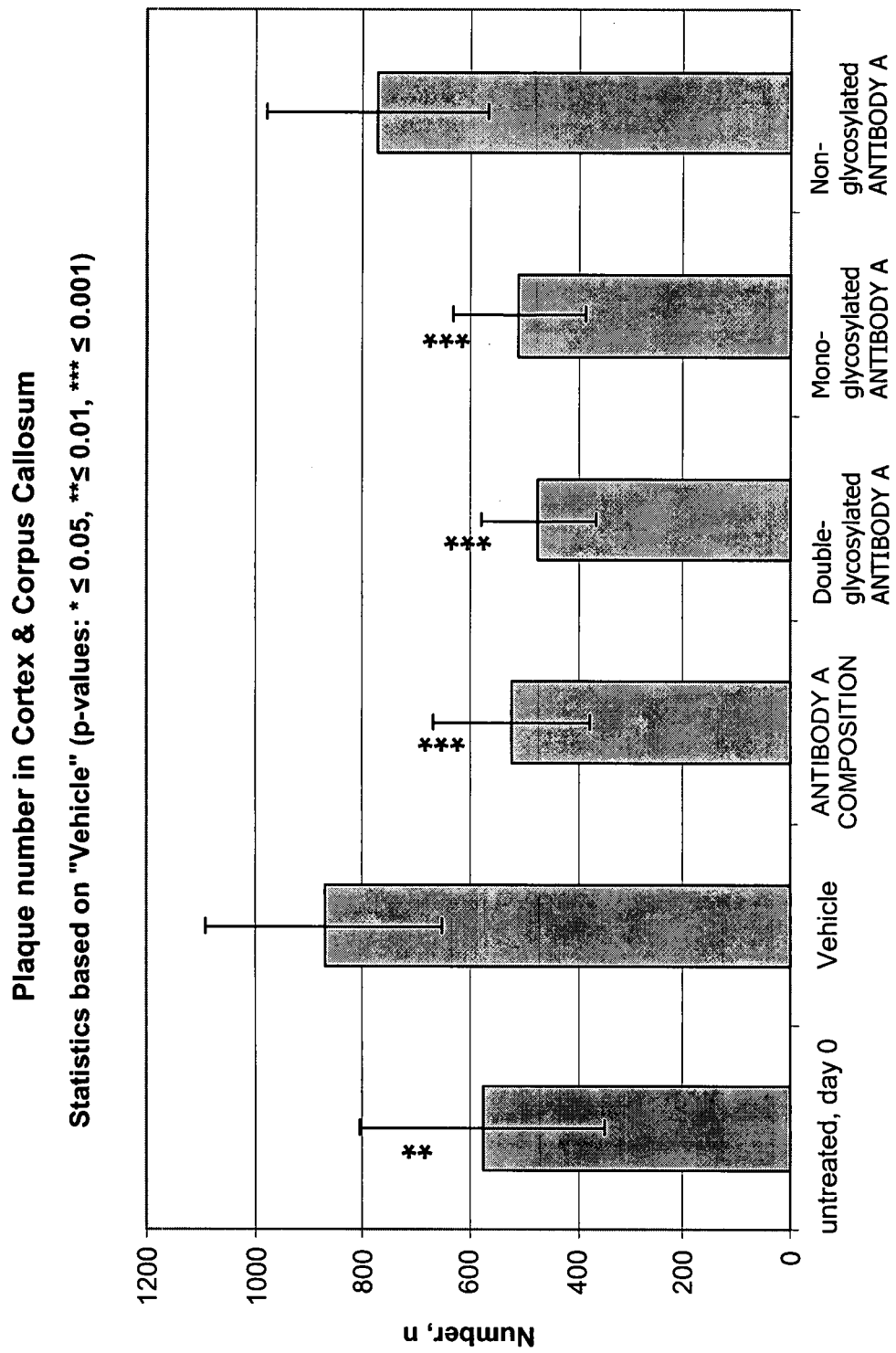
Figure 16C:
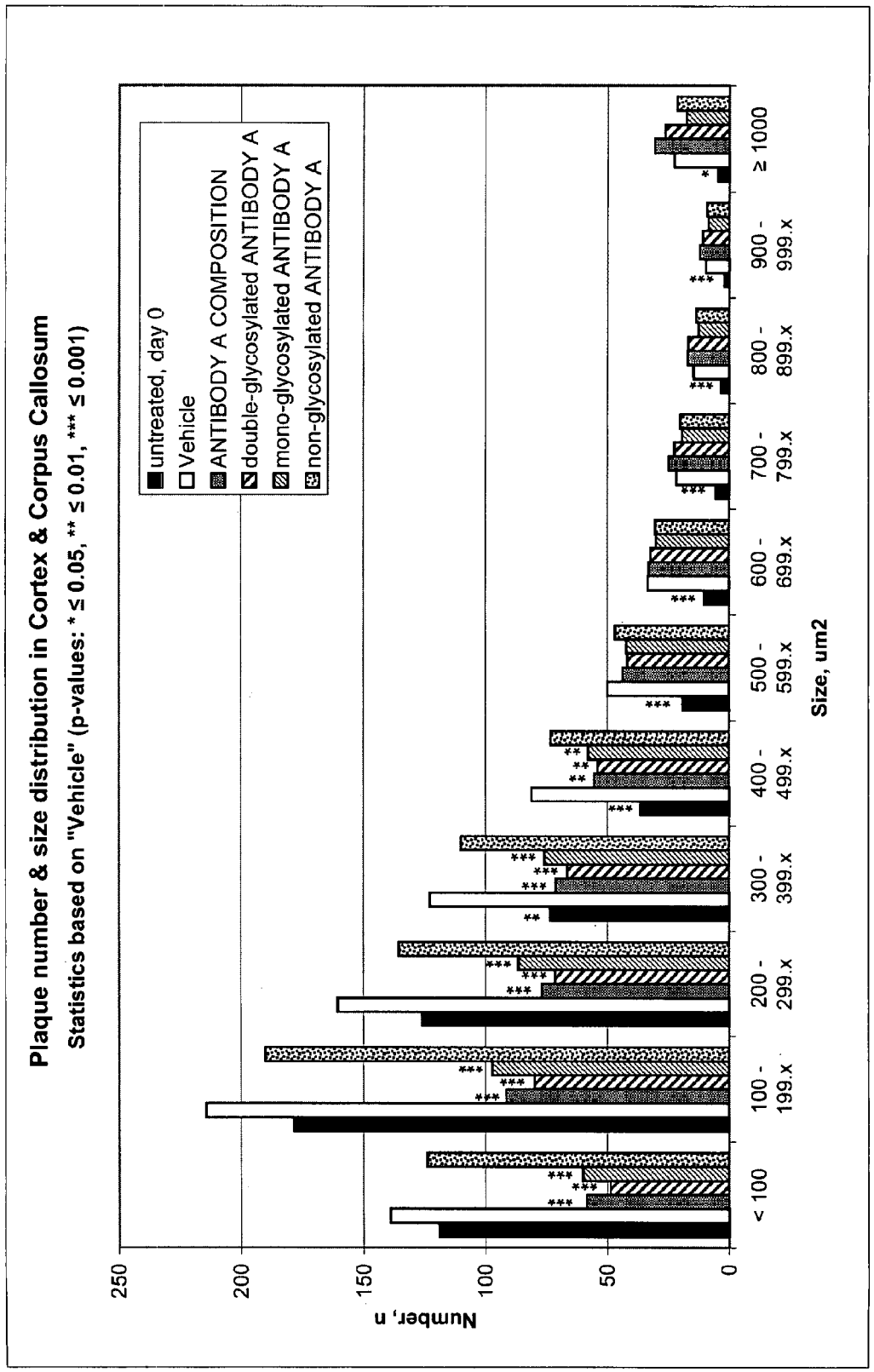

Amyloid plaque reduction in the neocortical region together with the corpus callosum is depicted in FIG. 16. The mean reduction of total amyloid-β plaque surface was determined for the antibody treated groups: 19% for ANTIBODY A COMPOSITION, 27% for double-glycosylated ANTIBODY A, 30% for mono-glycosylated ANTIBODY A and 10% for non-glycosylated ANTIBODY A. The mean reduction in total amyloid-β plaque number was found to be 40% for ANTIBODY A COMPOSITION, 46% for double-glycosylated ANTIBODY A, 42% for mono-glycosylated ANTIBODY A and 11% for non-glycosylated ANTIBODY A.

Figure 17A:
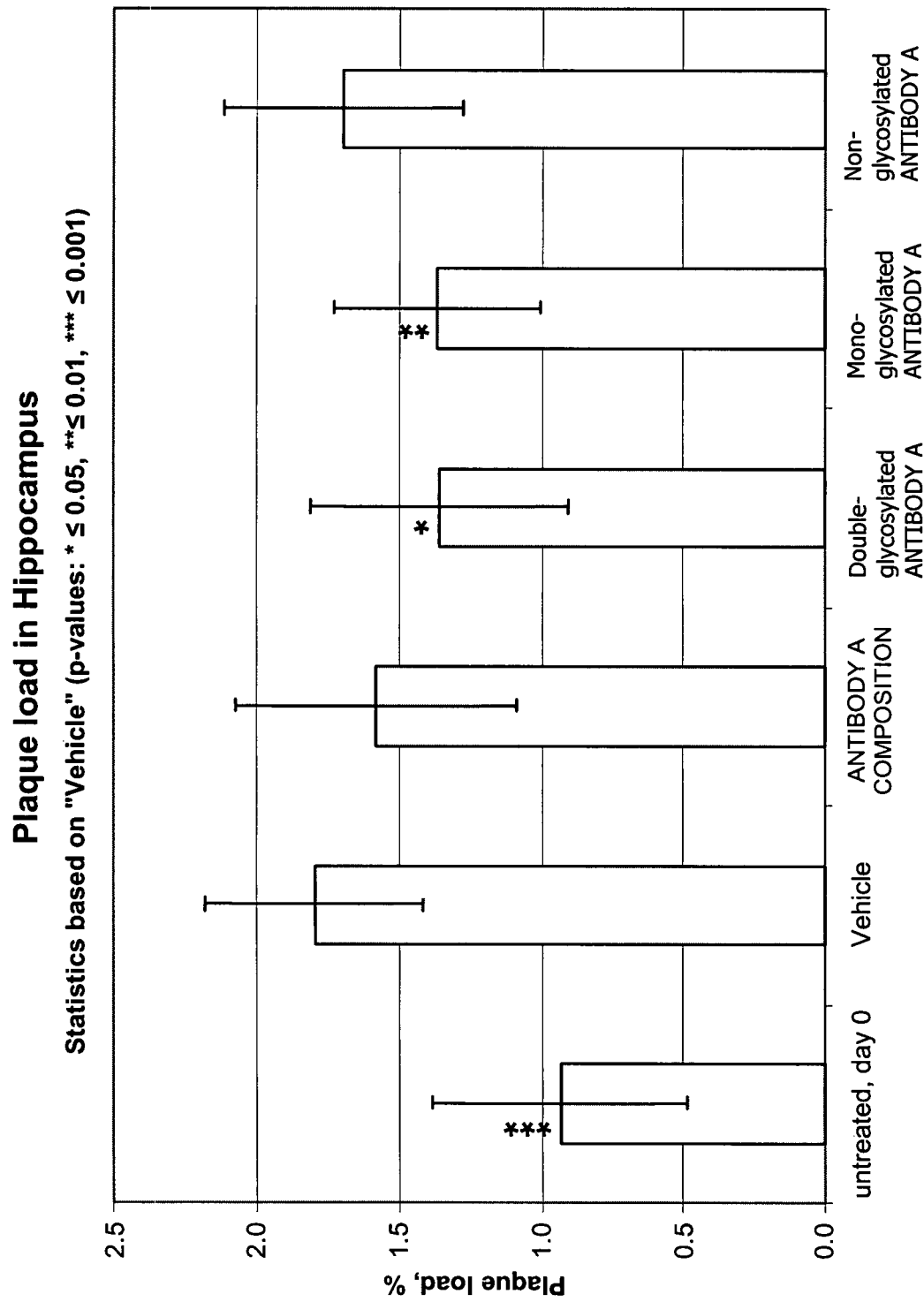
FIG. 17: Total plaque surface (A), total plaque number (B) and plaque number and size distribution (C) in the hippocampus region after 5 month treatment with ANTIBODY A COMPOSITION (which comprises mono- and double-glycosylated ANTIBODY A), double-glycosylated and mono-glycosylated ANTIBODY A isoforms (20 mg/kg weekly, i.v.) or vehicle.
Figure 17B:
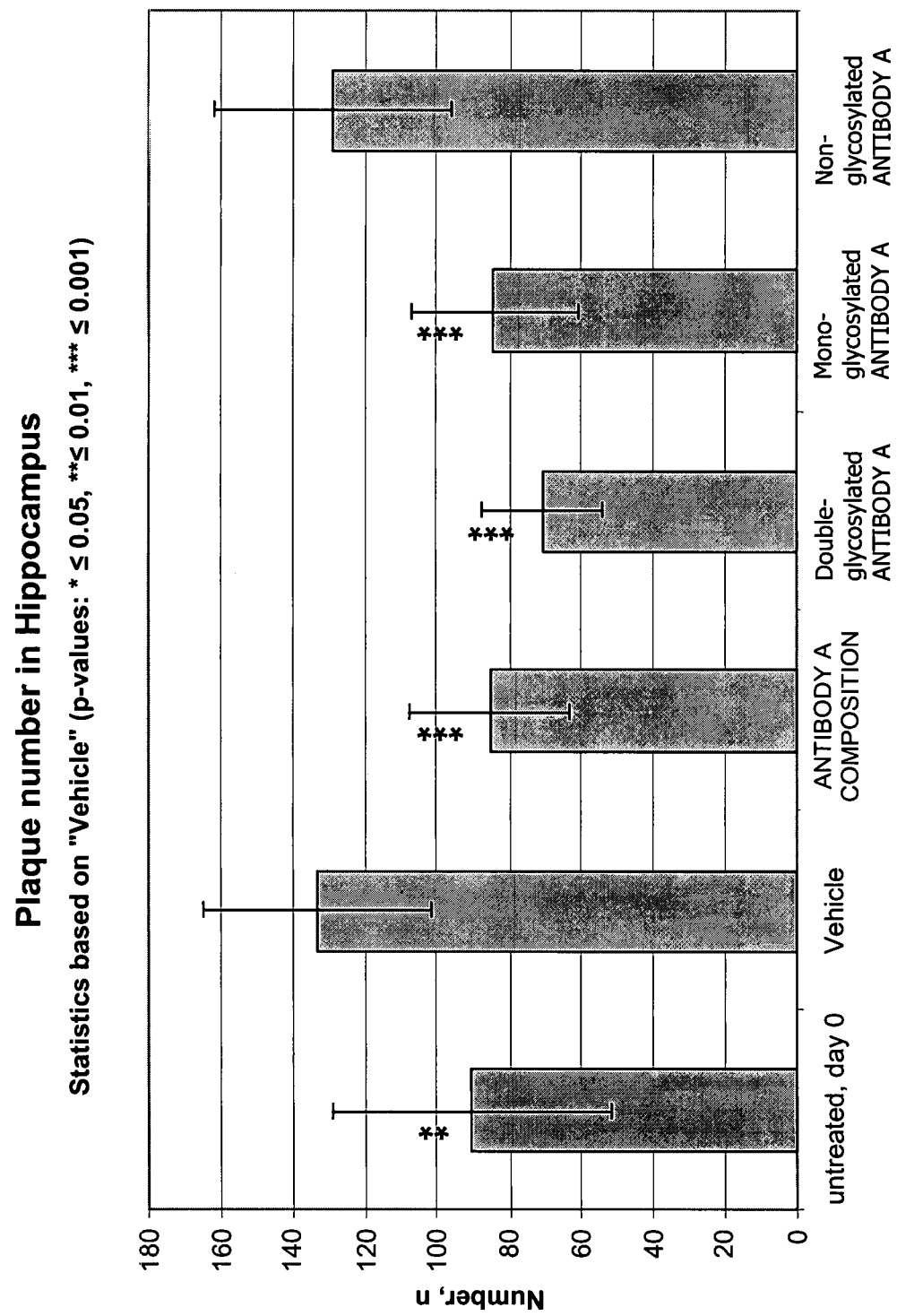
Figure 17C:
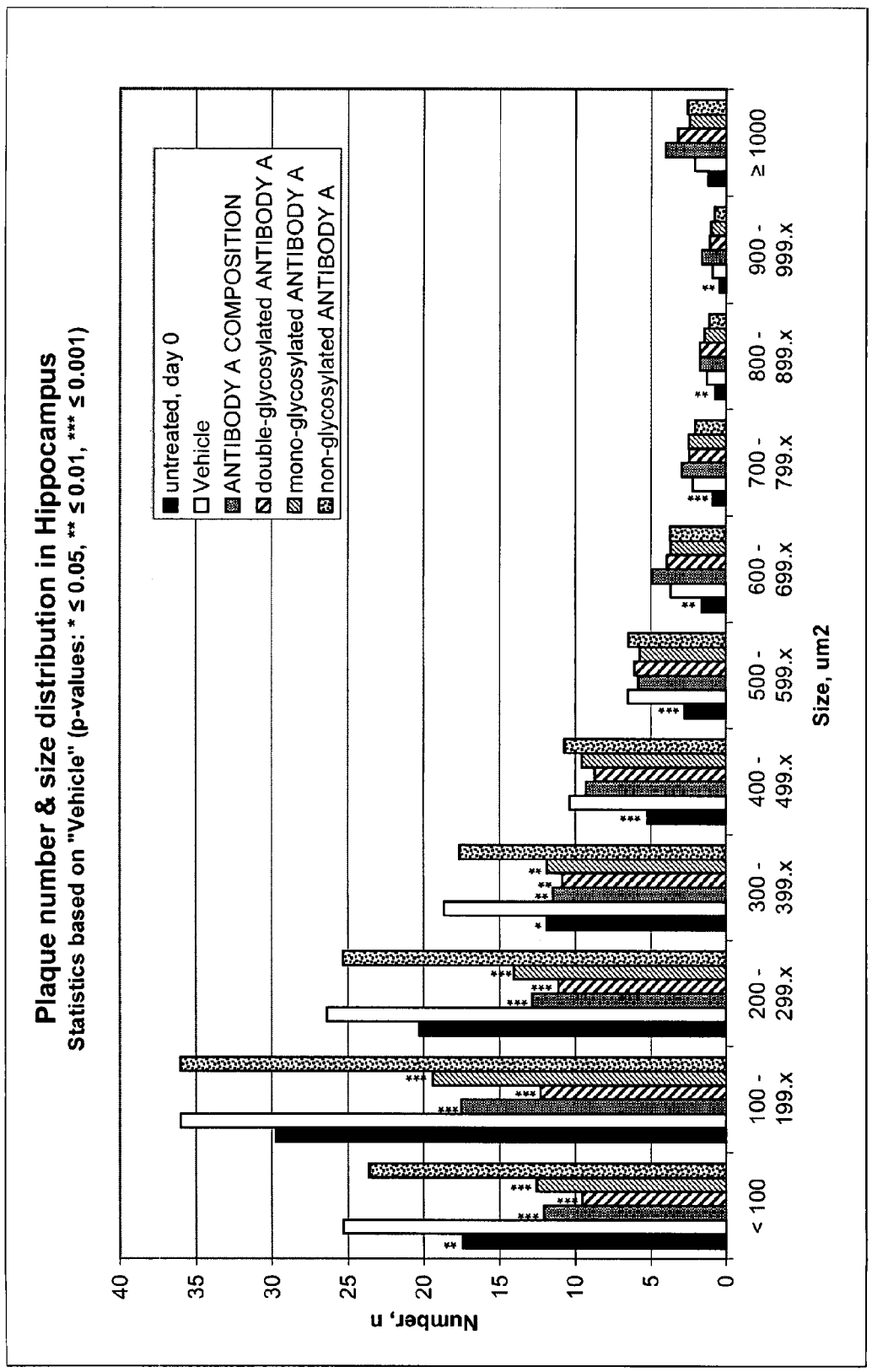

Amyloid plaque reduction in the entire hippocampal region is depicted in FIG. 17. The mean reduction of total amyloid-β plaque surface was determined for the antibody treated groups: 12% for ANTIBODY A COMPOSITION, 24% for double-glycosylated ANTIBODY A, 24% for mono-glycosylated ANTIBODY A and 6% for non-glycosylated ANTIBODY A. The mean reduction in total amyloid-β plaque number was found to be 36% for ANTIBODY A COMPOSITION, 46% for double-glycosylated ANTIBODY A, 37% for mono-glycosylated ANTIBODY A and 3% for non-glycosylated ANTIBODY A.

Figure 18A:
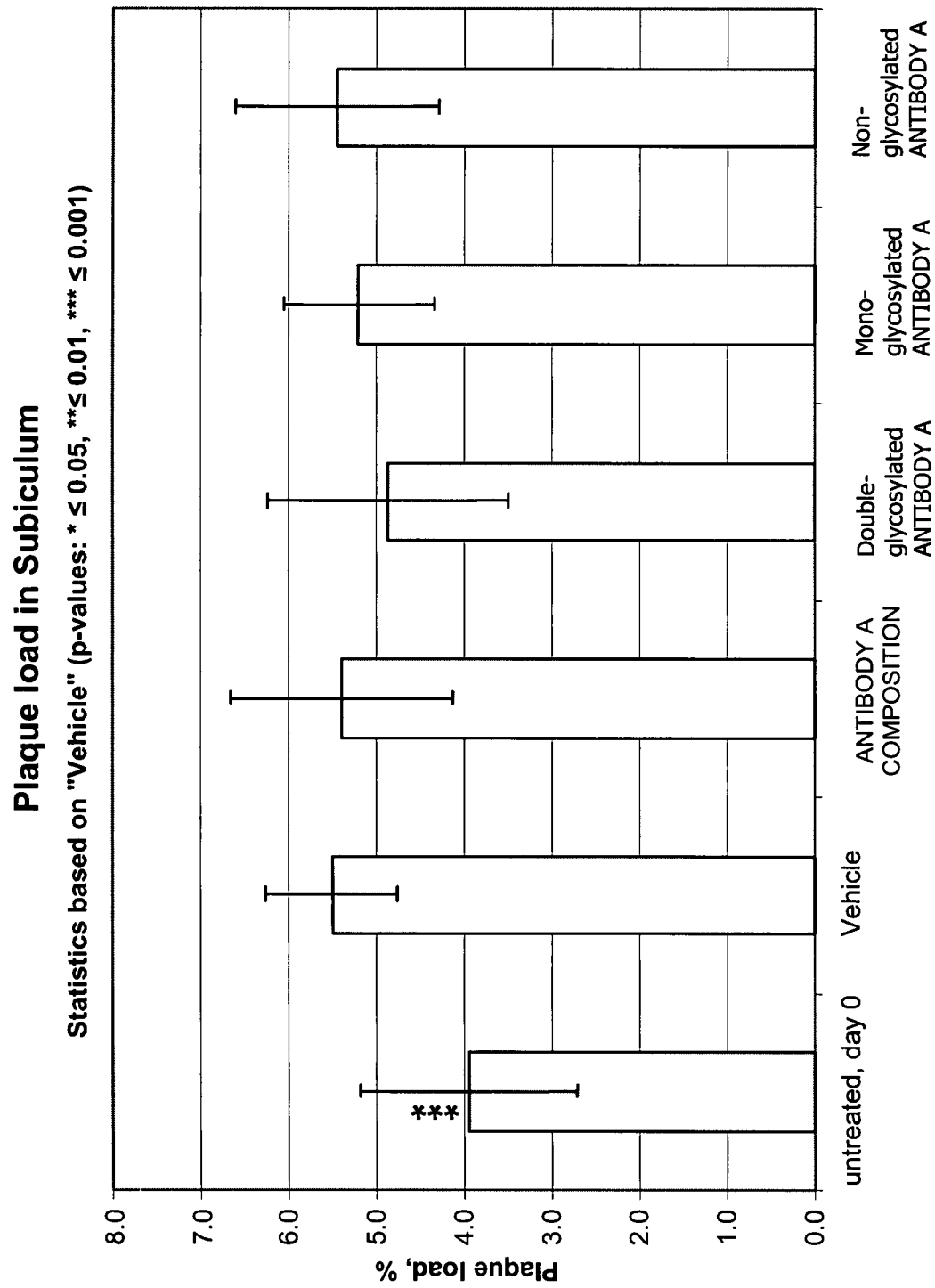
FIG. 18: Total plaque surface (A), total plaque number (B) and plaque number and size distribution (C) in the subiculum region after 5 month treatment with ANTIBODY A COMPOSITION (which comprises mono- and double-glycosylated ANTIBODY A), double-glycosylated and mono-glycosylated ANTIBODY A isoforms (20 mg/kg weekly, i.v.) or vehicle.
Figure 18B:
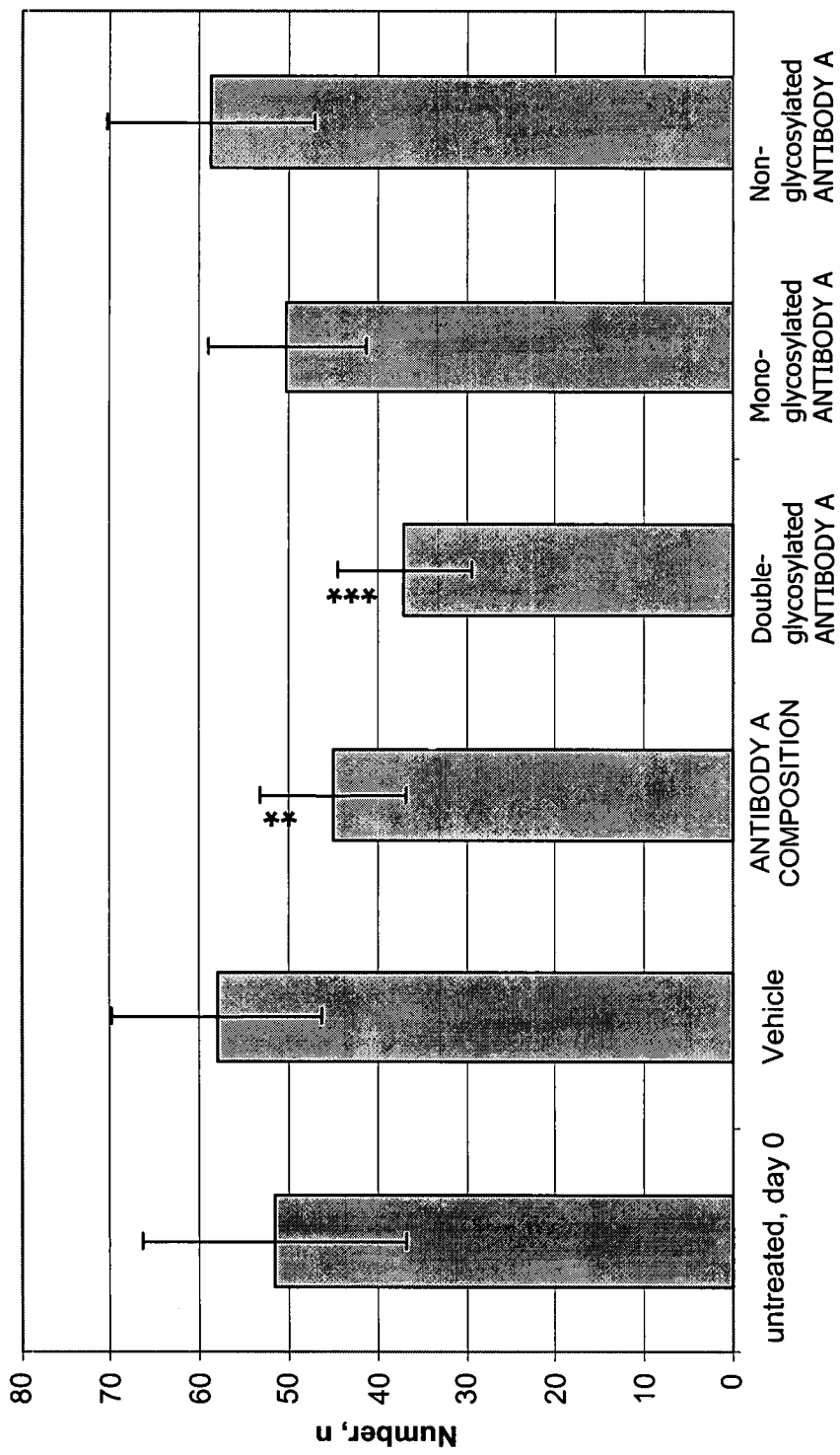
Figure 18C:
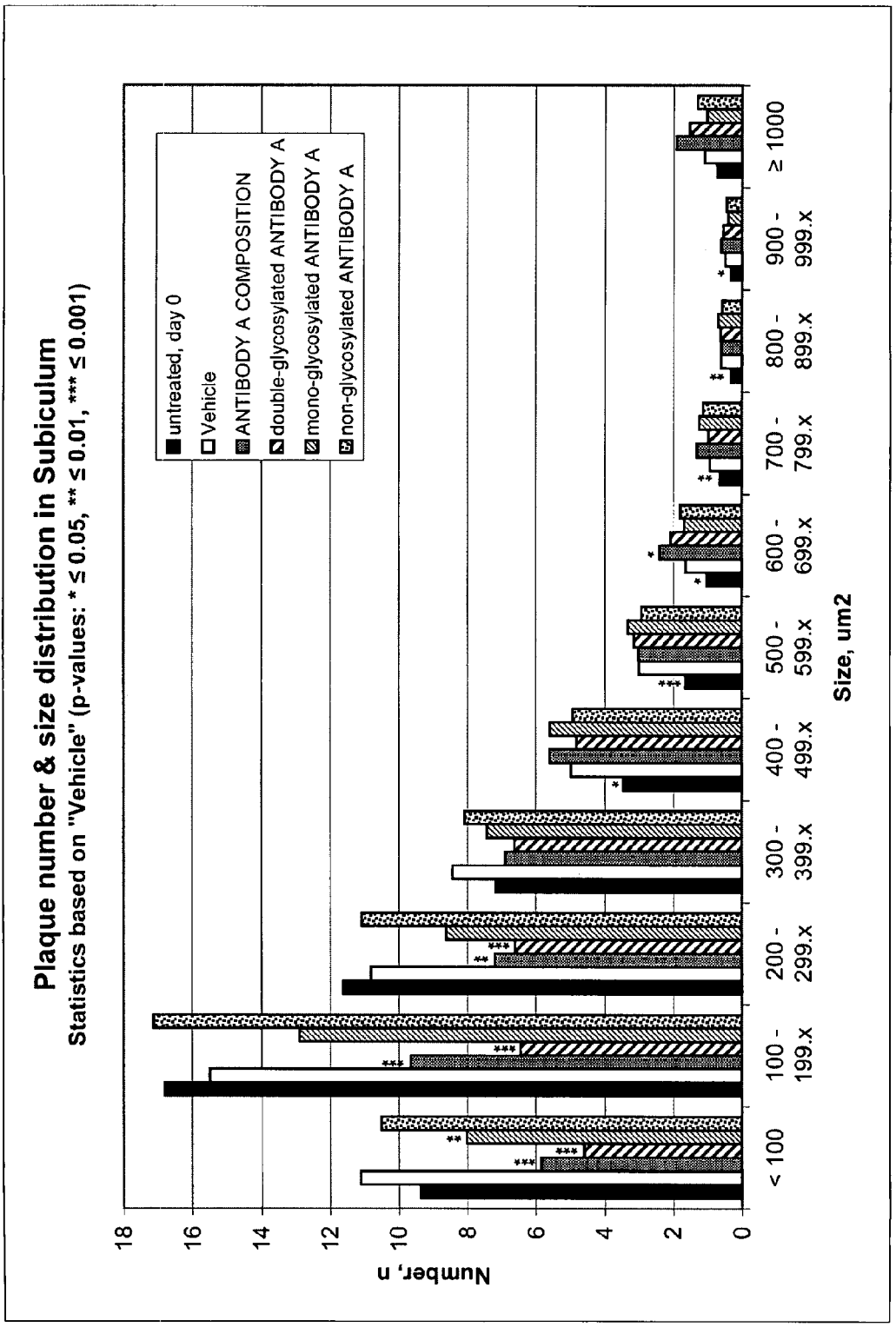

Amyloid plaque reduction in the subiculum, a high susceptibility region for amyloidosis is shown in FIG. 18. The mean reduction of total amyloid-β plaque surface was determined for the antibody treated groups: 2% for ANTIBODY A COMPOSITION, 12% for double-glycosylated ANTIBODY A, 5% for mono-glycosylated ANTIBODY A and 1% for non-glycosylated ANTIBODY A. The mean reduction in total amyloid-β plaque number was found to be 22% for ANTIBODY A COMPOSITION, 36% for double-glycosylated ANTIBODY A, 13% for mono-glycosylated ANTIBODY A and 1% for non-glycosylated ANTIBODY A. ANTIBODY A COMPOSITION and the main N-glycosylation isoforms (double-glycosylated ANTIBODY A and mono-glycosylated ANTIBODY A) showed a comparable effectivity to decrease amyloid-β plaque load and plaque number. Reduction of plaque load was most pronounced and statistically significant in regions with low or moderate amyloidosis.

Overall, reduction of amyloid-β plaque number was found statistically significant after treatment with ANTIBODY A COMPOSITION and both comprising Asn52 glycosylated isoforms of ANTIBODY A in all measured brain regions. In contrast thereto, only a minor effect on amyloid-β plaque number was found in the thalamus and no significant effects on amyloid-β plaque number in the other investigated brain regions was found after treatment with the non-glycosylated isoform of Antibody A, which is excluded from ANTIBODY A COMPOSITION after the purification as detailed in the invention.

We also investigated potency of plaque clearance in relation to the plaque size. Generally, effectivity of tested human anti-Aβ antibodies was found most pronounced for the clearance of small amyloid-β plaques. This was observed in all brain regions (FIGS. 15 C, 16 C, 17 C and 18 C). In contrast, there was only a minimal or non-significant trend observed for the non-glycosylated isoform of ANTIBODY A.

Comparative analysis of ANTIBODY A and the major Asn52 glycosylation isoforms demonstrate a comparable capacity to lower plaque load, while the non-glycosylated isoform has no significant effect on plaque lowering.

Example 16

Pharmacokinetics of In Vivo Binding of ANTIBODY A COMPOSITION to Amyloid-β Plaques Two dosing frequencies were compared in order to investigate the binding kinetics of ANTIBODY A COMPOSITION which comprises mono-glycosylated ANTIBODY A and double-glycosylated ANTIBODY A and is devoid of non-glycosylated ANTIBODY A as defined above.

Therefore, PS2APP transgenic male mice were injected i.v. with ANTIBODY A COMPOSITION via the tail vein either 4 times at biweekly intervals at 0.05, 0.1 and 0.3 mg/kg or 3 times at monthly interval with 0.075, 0.15 and 0.45 mg/kg. For comparison, 0.1 mg/kg was administered once and twice at biweekly intervals and 0.15 mg/kg twice at monthly interval. Following administration all mice were sacrificed two weeks after last dosing. Unfixed PS2APP brain tissue was prepared for sagital sectioning between lateral ~1.92 and 1.2 mm according to Paxinos and Franklin, including thalamus, hippocampal formation and cortical areas. Brains were sectioned at 40 µm using a cryostat.

An immuno-fluorescence ex vivo immuno-staining approach was used to detect bound ANTIBODY A COMPOSITION antibodies. Therefore, brains were sectioned and incubated with the detection antibody, an affinity-purified goat anti-human (GAH) IgG (H+L) conjugated to Cy3 (#109-165-003, lot 49353, Jackson Immuno Research) at a concentration of 15 µg/ml for 1 hour at room temperature. A counterstaining for amyloid-β plaques was done by incubation with BAP-2, a mouse monoclonal antibody against Aβ conjugated to Alexa488 fluorophore at a concentration of 0.5 µg/ml for 1 hour at room temperature.

Images were recorded in the occipital cortex close to the cerebellum using a Leica TCS SP2 AOBS confocal laser scanning microscope as described above. Computer-assisted image processing was performed using the IMARIS software (Bitplane, Switzerland). Images of plaques were first selected using the crop function of the software for the lower doses except the two highest doses of 0.3 and 0.45 mg/kg which required a different gain setting for linear signal recording. The SURPASS function was used to select the positive voxels after thresholding (T) as readout for bound GAH-Cy3 at the site of amyloid-β plaques. Threshold settings were 19 and 12 for lower and higher dose groups, respectively. As a control for amyloid-β plaque specificity, images of the GAH-Cy3 stainings were compared after double labeling with images of plaques stained by mouse monoclonal BAP2 conjugated to Alexa488 and recorded in a different channel.

Descriptive statistics to quantitative description of all images was done with the IMARIS MeasurementPro software module. Mean voxel fluorescence intensity (MVI) values were determined from selected amyloid-β plaques in the low dose groups or total signal from images in the high dose groups. The baseline MVI (B) is due to instrumental noise, tissue scatter signal and autofluorescence of lipofuscin. For background correction, B was determined by measuring the average signal intensity at areas apart from amyloid-β plaques and subsequently subtracted from the MVI of all measured images (MVI−B=S). Signal intensity (S) values resembling averaged intensities on plaques obtained from 3 to 4 images from each one brain section per mouse and dose group. For comparability, signal intensities were normalized to a reference sample obtained from a previous study. As reference we used PS2APP mouse brain sections after a single (lose administration of 0.25 mg/kg. Measurement endpoint was one week after dosing.

All measured intensity values were normalized to the average intensity at amyloid-β plaques obtained after a single dose administration of ANTIBODY A COMPOSITION at 0.25 mg/kg that was measured one week after dosing (see following table). The normalized values for mean relative fluorescence intensity of immunopositive amyloid-β plaques were obtained by CLSM after immunostaining and measuring signal intensities averaged from 3 animals per dose group. Plaques without detectable ANTIBODY A COMPOSITION derived ANTIBODY A were observed only in the lower dose groups, most likely due to limited or partial occupancy of ANTIBODY A COMPOSITION derived ANTIBODY A at the plaque surface, which might have been lost during the sectioning process. Therefore, only immunopositive plaques were included for the comparative analysis.

Mean relative fluorescence intensity per dose group after multiple i.v. (BOLUS) administration of ANTIBODY A COMPOSITION in PS2APP transgenic mice is shown in the following table:

| Dose - interval/injections | Normalized Average Mean Fluorescence Intensity of immunopositive ANTIBODY A COMPOSITION Amyloid-β Plaques | | Percentage of ANTIBODY A COMPOSITION immunonegative amyloid-β plaques |
|---|---|---|---|
| | % | SD | % |
| 0.25 mg - single[1] | 100 | 6 | 0 |
| 0.05 mg - biweekly/4x | 53 | 2 | 58 |
| 0.075 mg - monthly/3x | 57 | 6 | 39 |
| 0.15 mg - monthly/2x | 106 | 6 | 19 |
| 0.1 mg - biweekly/1x | 59 | 8 | 45 |
| 0.1 mg - biweekly/2x | 83 | 26 | 21 |
| 0.1 mg - biweekly/4x | 88 | 12 | 2 |
| 0.15 mg - monthly/3x | 93 | 19 | 1 |
| 0.3 mg - biweekly/4x | 148 | 24 | 0 |
| 0.45 mg - monthly/3x | 184 | 20 | 0 |

[1]Experimental values represent intensity values normalized to the value obtained from a single dose of 0.25 mg/kg after 1 week.

Figure 19:
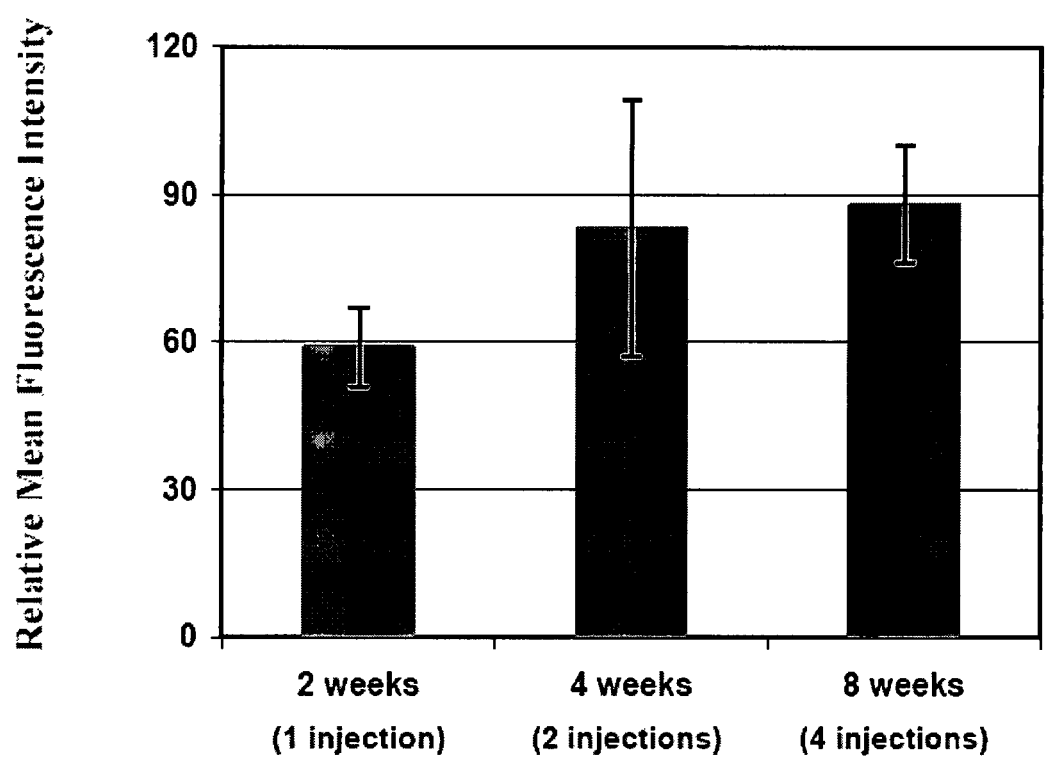
FIG. 19: Measurement of fluorescence intensity of immunostained ANTIBODY A COMPOSITION bound to amyloid-β plaques after biweekly dosing of 0.1 mg/kg with 1, 2 and 4 i.v. applications to PS2APP mice. Analysis was done at 2 weeks after last injection.

FIG. 19 shows binding of ANTIBODY A COMPOSITION in relation to the number of successive biweekly doses at 0.1 mg/kg. After two applications mean intensity appeared increased, although the extent of immunostaining varies considerably and therefore did not reach significance. After 4 injections, amyloid-β plaques are immunostained more homogenously, but mean intensity is only slightly increased. Overall, the data for biweekly application clearly indicate a tendency of increased plaque binding that is correlated with the number of applications.

Figure 20:
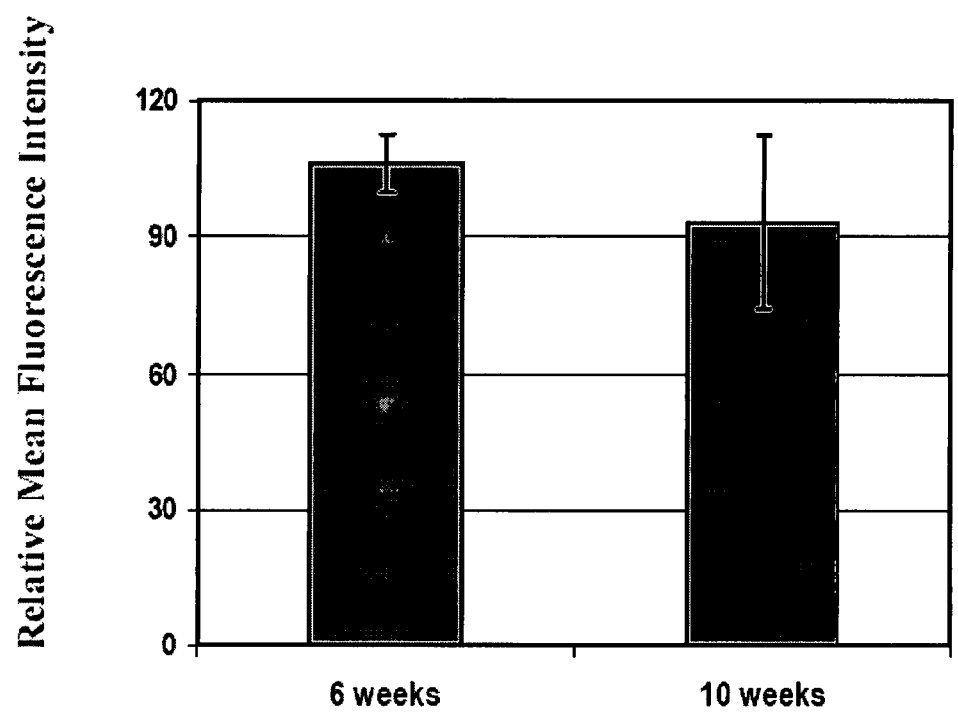
FIG. 20: Measurement of fluorescence intensity of immunostained ANTIBODY A COMPOSITION bound to amyloid-β plaques after monthly dosing of 0.15 mg/kg with 2 and 3 i.v. applications to PS2APP mice. Analysis was done at 2 weeks after last injection.

FIG. 20 shows binding of ANTIBODY A COMPOSITION in relation to the number of successive monthly doses at 0.15 mg/kg. Interestingly, comparable levels are obtained after 2 and 3 applications. This was not necessarily expected and might indicate initiation of early effects which contribute to time-dependent differences in clearance mechanism, like delayed microglia cell activation.

Figure 21:
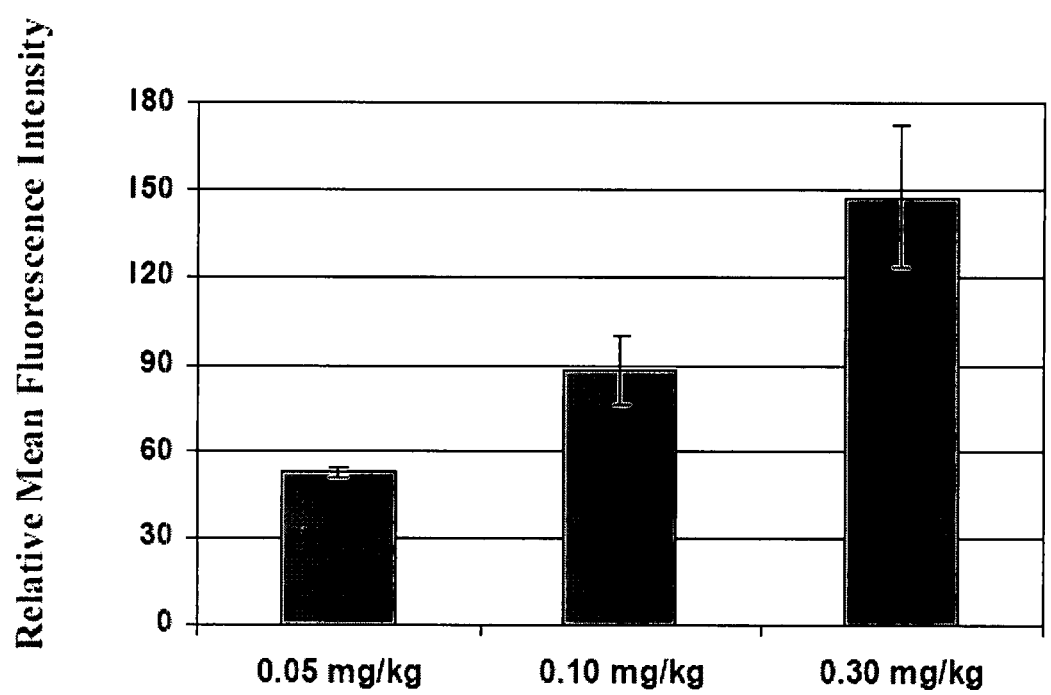
FIG. 21: Measurement of fluorescence intensity of immunostained ANTIBODY A COMPOSITION bound to amyloid-β plaques after 4 biweekly injections of 0.05, 0.1 and 0.30 mg/kg to PS2APP mice, suggesting dose-related amyloid-plaque binding. Analysis was done at 2 weeks after last injection.
Figure 22:
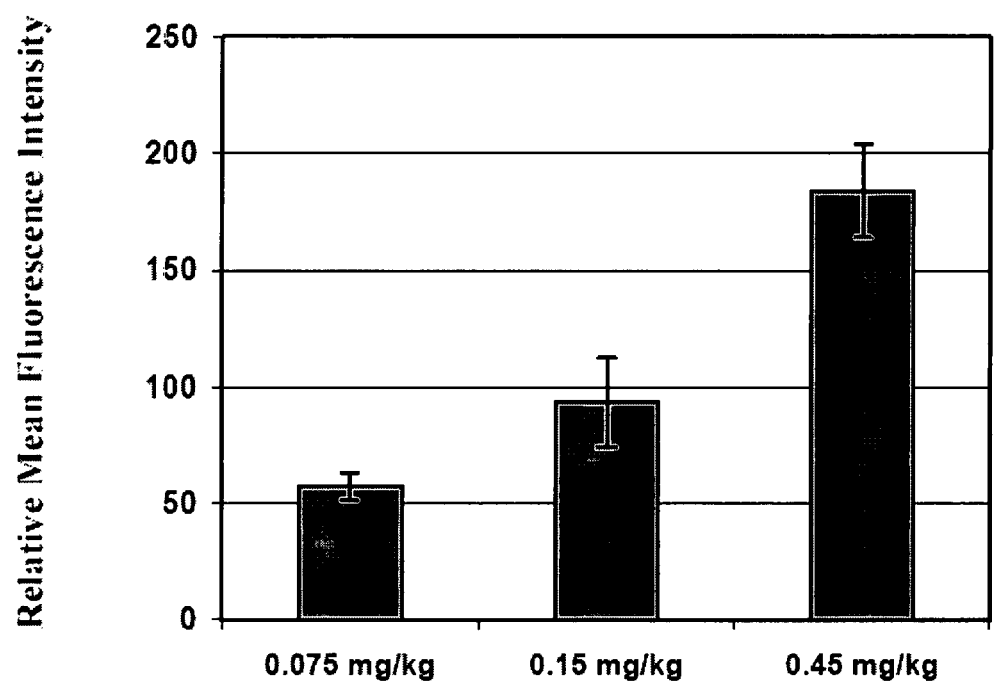
FIG. 22: Measurement of fluorescence intensity of immunostained ANTIBODY A COMPOSITION bound to amyloid-β plaques after 3 monthly injections of 0.075, 0.15 and 0.45 mg/kg to PS2APP mice, suggesting dose-related amyloid-plaque binding. Analysis was done at 2 weeks after last injection.

The binding efficacy of ANTIBODY A COMPOSITION in relation to administered dose is shown in FIGS. 21 and 22. Biweekly doses at 0.05, 0.1 and 0.3 mg/kg (FIG. 21) and monthly doses of 0.075, 0.15 and 0.45 mg/kg (FIG. 22) clearly showed a dose relationship. It is also evident that the response is not linear and additional factors like a temporally delayed activation of microglia cells might contribute to the observed non-linearity.

It thus can be concluded that ANTIBODY A COMPOSITION-binding to mouse Aβ plaques is dose-related with indications that multiple doses are accumulative.

Example 17

Analysis of Antigen-Dependent Cellular Phagocytosis

In order to determine the ANTIBODY A COMPOSITION-mediated phagocytic effect, genuine Aβ plaques from AD brain slices were pre-incubated with different concentrations of ANTIBODY A COMPOSITION which comprises mono-glycosylated ANTIBODY A and double-glycosylated ANTIBODY A and is devoid of non-glycosylated ANTIBODY A as defined above and exposed to living human primary monocytes.

Unfixed human AD brain tissue sections from the occipital cortex region were prepared from a severe Aβ case (Braak stage IV). Before adding living cells sections were rehydrated with PBS for 5 minutes. ANTIBODY A COMPOSITION antibodies were applied by incubation at defined concentrations in PBS for 1 hour. After washing with PBS living cells were added. Prestimulated human primary monocytes were used at 0.8 and 1.5×10⁶/ml in RPMI 1640 (Gibco #61870-044) medium with 1% antibiotic solution from a stock solution containing 10,000 U/ml penicillin and 10,000 mg/ml streptomycin (Gibco #15140-122) and incubated at 37° C. with 5% carbon dioxide for 2 to 4 days. Methods for the preparation of prestimulated human primary monocytes are well known in the art e.g. by use of stimulating factors, like macrophage colony-stimulating factor (M-CSF).

After incubation, culture medium was gently removed and sections preserved by chemical fixation with 2% formaldehyde in PBS for 10 minutes. Staining of residual Aβ plaque load was done by incubation with BAP-2, a mouse monoclonal antibody against Aβ conjugated to Alexa488 fluorophore (Molecular Probes: A-20181, monoclonal antibody labeling kit) at a concentration of 10 mg/ml for 1 hour at room temperature.

Quantification of plaque removal was determined by measuring the immunofluorescence of residual stained Aβ plaques. Images were recorded on a Leica TCS SP2 AOBS confocal laser scanning microscope. One optical layer was recorded at excitation wavelength of 488 nm at a pinhole setting of 4 Airy using a HCX PL FL 20×/0.40 correction objective except in one experiment, where a HCPL Fluotar 10×/0.30 objective at a pinhole setting of 3 was used instead. Instrument settings were kept constant for all images to allow a relational quantitative comparison. Specifically, laser power, gain and offset were adjusted to allow for signal intensity monitoring within the dynamic range. For each ANTIBODY A COMPOSITION concentration grey matter regions were recorded at comparable positions from consecutive sections in order to minimize fluctuations possibly coming from anatomical differences in plaque load. Potential competitive binding of ANTIBODY A COMPOSITION and the detection antibody BAP-2, was measured in the absence of cells at all ANTIBODY A COMPOSITION concentrations. An unrelated human IgG1 (Serotec, PHP010) antibody was used as an additional control. Images analysis was performed using the IMARIS Software (Bitplane, Switzerland). The isosurface of BAP-2 positive pixels representing objects of BAP-2 s bound to the plaques were created by intensity thresholding. Surface area and total fluorescence intensity values were calculated using the "iso surface function" of the SurpassPro software module. Data were expressed as averaged staining area and total staining intensity values obtained from 5 grey matter regions of one brain section. The signal baseline is composed by the instrumental noise and tissue scatter signal was found negligible and was therefore not subtracted from the total intensity signal.

Figure 23:
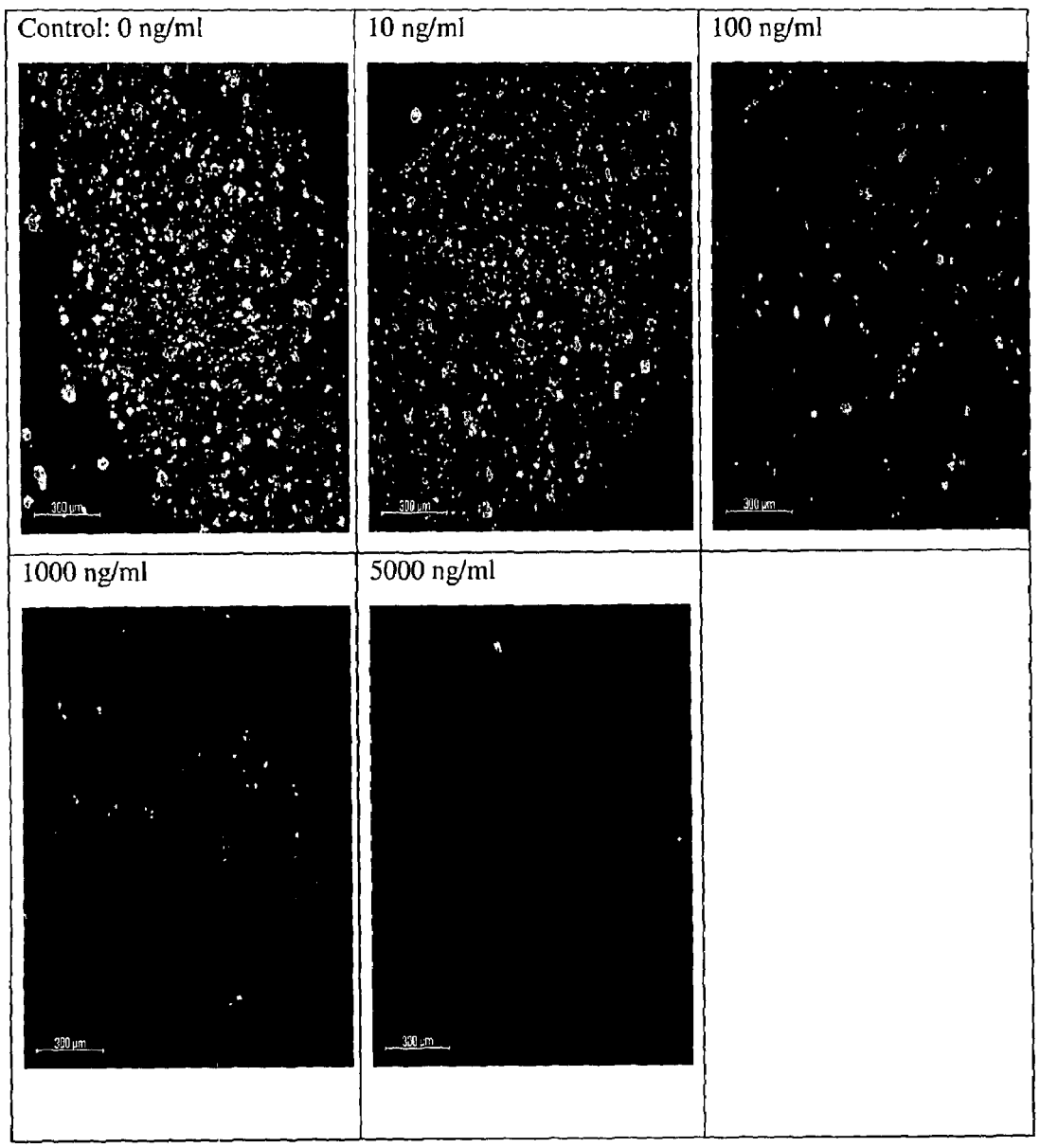
FIG. 23: Human AD brain sections stained against Aβ with anti-Aβ murine monoclonal antibody (BAP-2) after 40 hours incubation with ANTIBODY A COMPOSITION at indicated concentrations together with living differentiated primary human macrophages (0.8 million cells/ml). Results show reduction in amyloid load indicative for antigen-dependent cellular phagocytosis effect of ANTIBODY A COMPOSITION on amyloid-β plaques. Scale bar=300 μm.
Figure 24A:
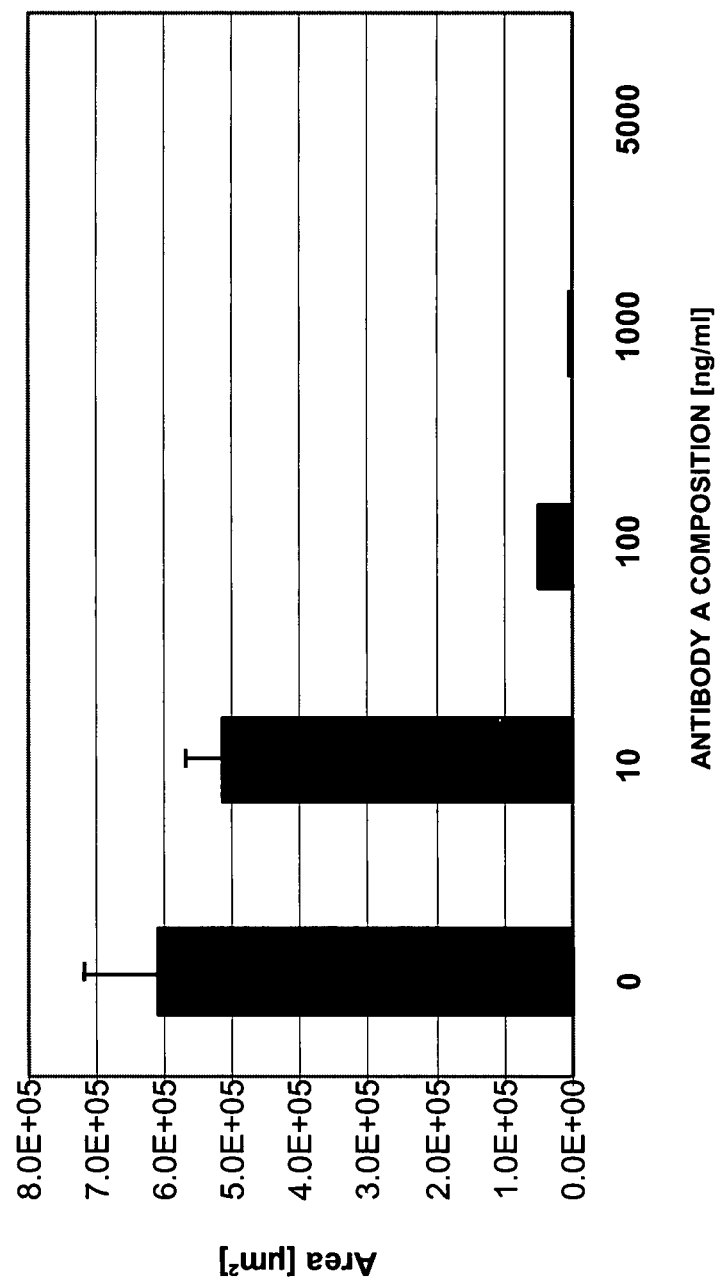
FIG. 24: Dose response of ANTIBODY A COMPOSITION on amyloid-β plaques from human AD brain sections when incubated with 0.8 million cells/ml. (A) shows total plaque area and (B) staining intensity.
Figure 24B:
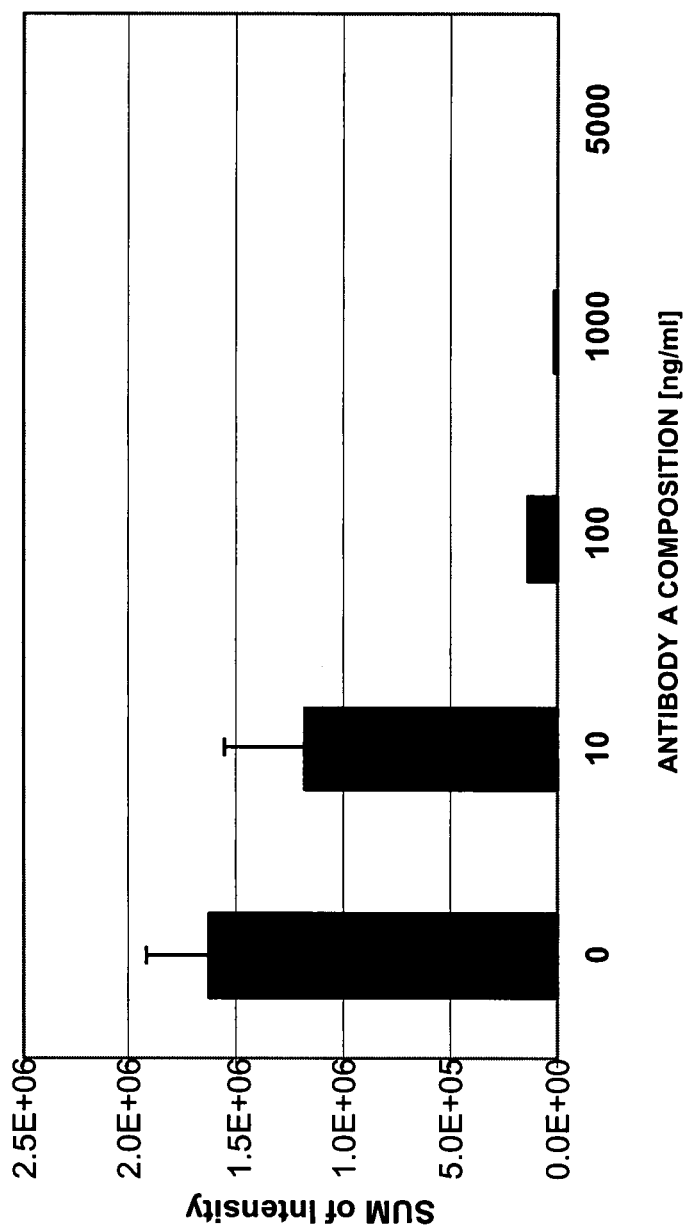

The qualitative effect of ANTIBODY A COMPOSITION was visualized by a decrease in Aβ plaque stain that indicates increased phagocytosis of Aβ plaques from human AD brain sections as shown in FIG. 23. Immunohistochemistry revealed a reduction in stainable Aβ plaques clearly visible after a pre-incubation with 100 ng/ml ANTIBODY A COMPOSITION already after 40 hours. The effect is very pronounced and at ANTIBODY A COMPOSITION concentrations of 1 and 5 mg/ml. Aβ plaques are substantially and increasingly cleared by cellular phagocytosis with only few large Aβ plaques remaining at 5 mg/ml. A quantitative measurement based on the immunoreactivity signals expressed as area and intensity of the same experiment is shown in FIG. 24.

Alternatively, the ANTIBODY A COMPOSITION-mediated phagocytic effect was determined using Aβ conjugated fluorescent polystyrene beads. Therefore, fluorescent beads (3 mm, Fluoresbrite carboxy YG, Polysciences Inc.) were coupled with Aβ. Briefly, beads were washed 2× by suspension and centrifugation in coupling buffer (50 mM MES buffer, pH 5.2, 1% DMSO). The pellet (approx. 10 ul) was suspended in 200 ul coupling buffer and activated by addition of 20 ul of a 20% solution of EDC (Ethyl-diaminopropyl-carbodiimide, Pierce) in coupling buffer. Immediate addition of 20 μg Aβ (1-40) or Aβ (1-42) (in 0.1% ammonium hydroxide, Bachem) started the coupling reaction. After one night incubation the beads were washed with 3×0.5 ml 10 mM Tris.HCl pH 8.0 and 3×0.5 ml storage buffer (10 mm Tris.HCl pH 8.0, 0.05% BSA, 0.05% NaN₃). The 1% suspension was stored at 4° C. until use. As a negative control Fluoresbrite carboxy NYO (red fluorescence) beads were coupled with all-D amino acid Aβ (1-40). (in 0.1% ammonium hydroxide, Bachem).

Murine monocytes/macrophages (cell line P388D1) were grown in C24 transparent tissue culture clusters or C96 black microplates to approx. 50% confluency. The culture medium was IMEM with 5% FBS, glutamine and antibiotics. To block unspecific scavenger receptors 10 ml fucoidan (Fluka, 10 mg/ml in water) was added to 200 ml culture volume and incubated for 2 hours. ANTIBODY A COMPOSITION was added in serial dilutions and pre-incubated for 30 minutes. Fluorescent Aβ bead suspension (20 μl) was added and incubated for 3 hrs to allow phagocytosis. The adherent cells were washed vigorously 1× with ice cold EDTA and 2× with PBS in order to remove adhering agglutinates from the cell surface. The residual beads were either monitored by visual inspection at a Zeiss Axiovert 405 or for quantification by using a microplate fluorimeter (Fluoroscan, Labsystems) with 444 nm (Exc) and 485 nm (Em) filter settings.

Figure 25:
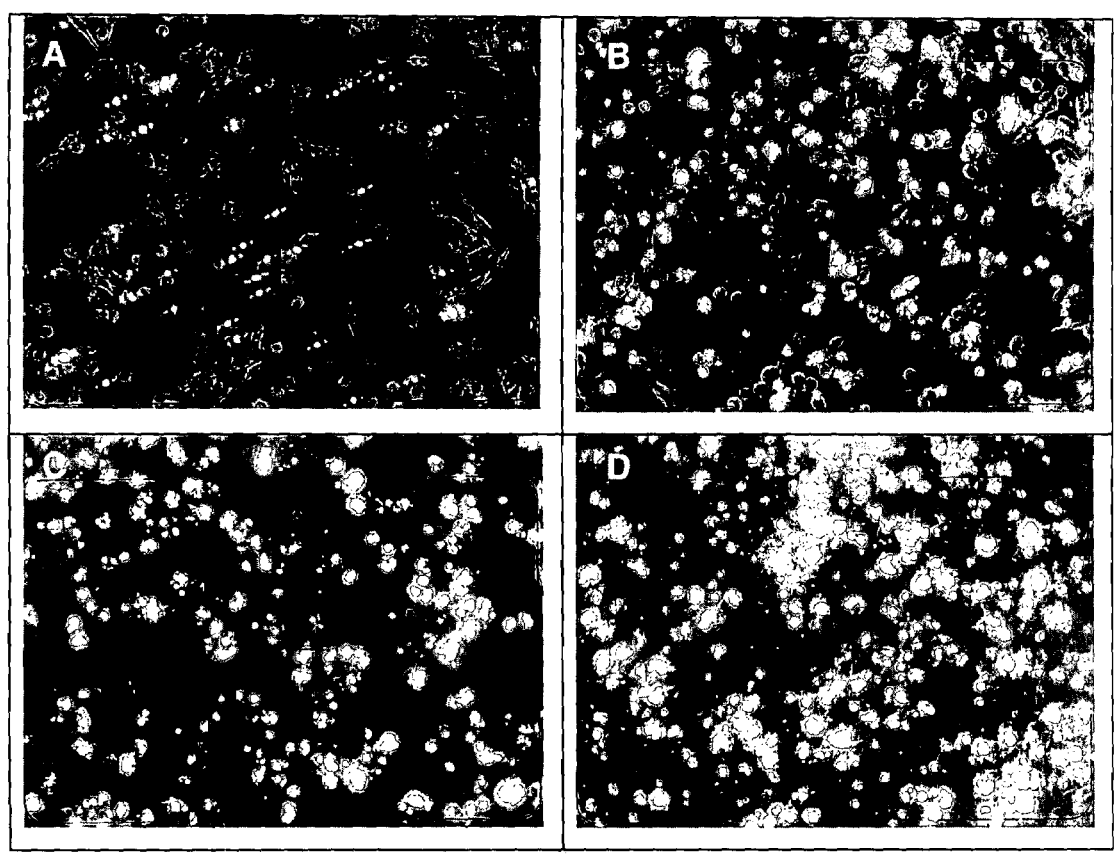
FIG. 25: Fluorescent microscopy of P388D1 cells incubated with 0, 0.1, 1 and 10 μg/ml ANTIBODY A COMPOSITION (A to D, respectively).
Figure 26:
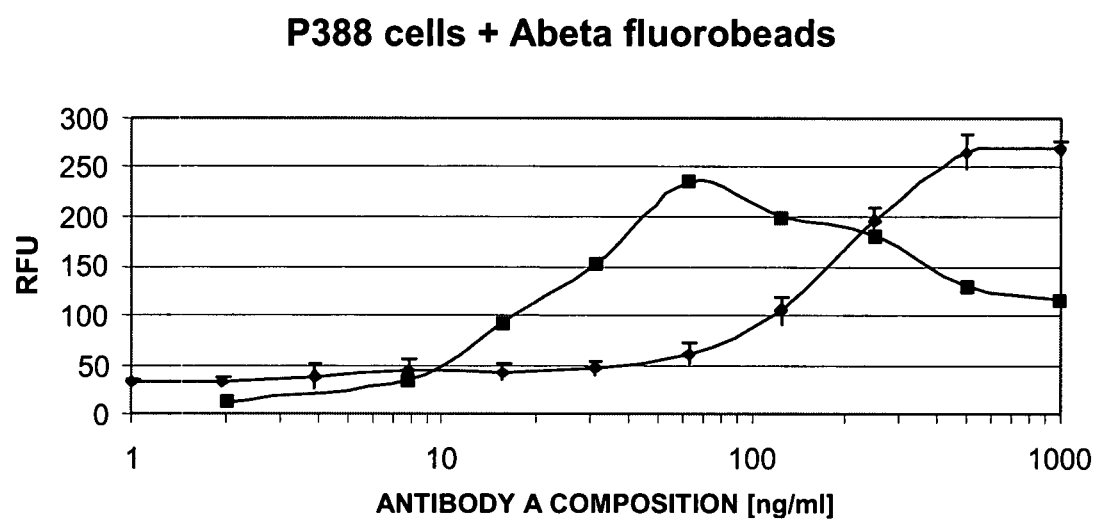
FIG. 26: Quantitative measurement of dose response of ANTIBODY A COMPOSITION using Aβ conjugated fluorobeads and P3881D1 cells (shown in relative fluorescent units, RFU). Two independent experiments indicate a considerable range of efficacy for ANTIBODY A COMPOSITION.

The qualitative effect of ANTIBODY A COMPOSITION on the phagocytosis of synthetic Aβ aggregates coupled to fluorescent fluorobeads by P388D1 cells is shown in FIG. 25. The quantitative determination of the dose response of ANTIBODY A COMPOSITION is shown in FIG. 26. Two independent experiments revealed a range from 30 to 200 ng/ml for EC50 and 10 to 60 ng/ml for MEC. The observed variability is likely caused by differences of the incubation stoichiometry, i.e. ratio of beads to cells. The observed decline of bead phagocytosis above a concentration >200 ng/ml is due to monovalent antibody interaction with limited antigen.

It thus can be concluded that ANTIBODY A COMPOSITION efficiently induces phagocytosis of Aβ plaques from AD brain tissue sections in a dose related manner.

The invention claimed is:

1. A pharmaceutical composition comprising antibody molecules and a pharmaceutically acceptable carrier or diluent,
   (a) wherein the antibody molecules comprise two light chains and two heavy chains:
      (i) wherein each of the heavy chains comprises SEQ ID NO: 6;
      (ii) wherein each of the light chains comprises SEQ ID NO: 8;
   (b) wherein the composition comprises, in admixture, antibody molecules that are mono-glycosylated in one but not both of their heavy chains at the asparagine residue of position 52 of SEQ ID NO: 6 and antibody molecules that are double-glycosylated in both of their heavy chains at the asparagine residue of position 52 of SEQ ID NO: 6; and
   (c) wherein, if present, any antibody molecule that is not glycosylated in either of its heavy chains at the asparagine residue of position 52 of SEQ ID NO: 6, is present in an amount of less than 5%.

2. The pharmaceutical composition according to claim 1, wherein, if present, any antibody molecule that is not glycosylated in either of its heavy chains at the asparagine residue of position 52 of SEQ ID NO: 6, is present in an amount of less than 4%.

3. The pharmaceutical composition according to claim 1, wherein, if present, any antibody molecule that is not glycosylated in either of its heavy chains at the asparagine residue of position 52 of SEQ ID NO: 6, is present in an amount of less than 3%.

4. The pharmaceutical composition according to claim 1, wherein, if present, any antibody molecule that is not glycosylated in either of its heavy chains at the asparagine residue of position 52 of SEQ ID NO: 6, is present in an amount of less than 2%.

5. The pharmaceutical composition according to claim 1, wherein, if present, any antibody molecule that is not glycosylated in either of its heavy chains at the asparagine residue of position 52 of SEQ ID NO: 6, is present in an amount of less than 1%.

6. The pharmaceutical composition according to claim 1, wherein, if present, any antibody molecule that is not glycosylated in either of its heavy chains at the asparagine residue of position 52 of SEQ ID NO: 6, is present in an amount of less than 0.5%.

7. The pharmaceutical composition according to claim 1, wherein the concentration of antibody molecules therein is from about 50 mg/mL to about 200 mg/mL.

8. The pharmaceutical composition according to claim 7, wherein the concentration of antibody molecules therein is from about 150 mg/mL to about 200 mg/mL.

9. The pharmaceutical composition according to claim 1, further comprising a vial that contains the pharmaceutical composition.

10. The pharmaceutical composition according to claim 1, wherein the pharmaceutically acceptable carrier or diluent comprises a sterile solution.

11. The pharmaceutical composition according to claim 1, wherein the pharmaceutical composition is in a lyophilized form.

12. The pharmaceutical composition according to claim 1, wherein the pharmaceutically acceptable carrier or diluent comprises a lyoprotectant.

13. The pharmaceutical composition according to claim 1, wherein the pharmaceutically acceptable carrier or diluent comprises a surfactant.

* * * * *

SEQUENCE LISTING

<160> NUMBER OF SEQ ID NOS: 76

<210> SEQ ID NO 1
<211> LENGTH: 378
<212> TYPE: DNA
<213> ORGANISM: artificial sequence
<220> FEATURE:
<223> OTHER INFORMATION: VH-region of ANTIBODY A

<400> SEQUENCE: 1

```
caggtggaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgct attaatgctt ctggtactcg tacttattat   180
gctgattctg ttaagggtcg ttttaccatt tcacgtgata attcgaaaaa caccctgtat   240
ctgcaaatga acagcctgcg tgcggaagat acggccgtgt attattgcgc gcgtggtaag   300
ggtaatactc ataagcctta tggttatgtt cgttattttg atgtttgggg ccaaggcacc   360
ctggtgacgg ttagctca                                                 378
```

<210> SEQ ID NO 2
<211> LENGTH: 126
<212> TYPE: PRT
<213> ORGANISM: artificial sequence
<220> FEATURE:
<223> OTHER INFORMATION: VH-region of ANTIBODY A

<400> SEQUENCE: 2

```
Gln Val Glu Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
        115                 120                 125
```

<210> SEQ ID NO 3
<211> LENGTH: 42
<212> TYPE: PRT
<213> ORGANISM: artificial sequence
<220> FEATURE:
<223> OTHER INFORMATION: A-beta

<400> SEQUENCE: 3

```
Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 4
<211> LENGTH: 52
<212> TYPE: PRT
<213> ORGANISM: artificial sequence
<220> FEATURE:
<223> OTHER INFORMATION: A-beta comprising peptide sequence

<400> SEQUENCE: 4

```
Ile Ser Glu Val Lys Met Asp Ala Glu Phe Arg His Asp Ser Gly Tyr
1               5                   10                  15

Glu Val His His Gln Lys Leu Val Phe Phe Ala Glu Asp Val Gly Ser
            20                  25                  30

Asn Lys Gly Ala Ile Ile Gly Leu Met Val Gly Gly Val Val Ile Ala
        35                  40                  45

Thr Val Ile Val
    50

<210> SEQ ID NO 5
<211> LENGTH: 1391
<212> TYPE: DNA
<213> ORGANISM: artificial sequence
<220> FEATURE:
<223> OTHER INFORMATION: heavy chain with Fc-region of ANTIBODY A

<400> SEQUENCE: 5
caggtggaat tggtggaaag cggcggcggc ctggtgcaac cgggcggcag cctgcgtctg      60
agctgcgcgg cctccggatt tacctttagc agctatgcga tgagctgggt gcgccaagcc    120
cctgggaagg gtctcgagtg ggtgagcgct attaatgctt ctggtactcg tacttattat    180
gctgattctg ttaagggtcg ttttaccatt tcacgtgata attcgaaaaa caccctgtat    240
ctgcaaatga acagcctgcg tgcggaagat acggccgtgt attattgcgc gcgtggtaag    300
ggtaatactc ataagcctta tggttatgtt cgttattttg atgtttgggg ccaaggcacc    360
ctggtgacgg ttagctcagc ctccaccaag ggtccatcgg tcttcccccc tggcaccctcc   420 tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccag atatcgtgcg atatcgtgca atcttgtgac aaaactcaca    720
catgcccacc gtgcccagca cctgaactcc tggggggacc gtcagtcttc ctcttccccc    780
caaaacccaa ggacaccctc atgatctccc ggacccctga ggtcacatgc gtggtggtgg    840
acgtgagcca cgaagaccct gaggtcaagt tcaactggta cgtggacggc gtggaggtgc    900
ataatgccaa gacaaagccg cgggaggagc agtacaacag cacgtaccgg gtggtcagcg    960
tcctcaccgt cctgcaccag gactggctga atggcaagga gtacaagtgc aaggtctcca    1020
acaaagcccc ccagccccca tcgagaaaac catctccaaa gccaaaggg cagccccgag    1080 aaccacaggt gtacaccctg cccccatccc gggatgagct gaccaagaac caggtcagcc    1140
tgacctgcct ggtcaaaggc ttctatccca gcgacatcgc cgtggagtgg gagagcaatg    1200
ggcagccgga gaacaactac aagaccacgc ctcccgtgct ggactccgac ggctccttct    1260
tcctctacag caagctcacc gtggacaaga gcaggtggca gcaggggaac gtcttctcat    1320
gctccgtgat gcatgaggct ctgcacaacc actacacgca gaagagcctc tccctgtctc    1380
cgggtaaatg a                                                          1391

<210> SEQ ID NO 6
<211> LENGTH: 456
<212> TYPE: PRT
<213> ORGANISM: artificial sequence
<220> FEATURE:
<223> OTHER INFORMATION: heavy chain with Fc-region of ANTIBODY A
```

```
<400> SEQUENCE: 6

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415
```

```
Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 7
<211> LENGTH: 648
<212> TYPE: DNA
<213> ORGANISM: artificial sequence
<220> FEATURE:
<223> OTHER INFORMATION: light chain of ANTIBODY A

<400> SEQUENCE: 7
gatatcgtgc tgacccagag cccggcgacc ctgagcctgt ctccgggcga acgtgcgacc      60
ctgagctgca gcgagcca gagcgtgagc agcagctatc tggcgtggta ccagcagaaa      120
ccaggtcaag caccgcgtct attaatttat ggcgcgagca gccgtgcaac tggggtcccg      180
gcgcgtttta gcggctctgg atccggcacg gattttaccc tgaccattag cagcctggaa      240
cctgaagact ttgcgactta ttattgcctt cagatttata atatgcctat tacctttggc      300
cagggtacga agttgaaat taaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgttag             648

<210> SEQ ID NO 8
<211> LENGTH: 215
<212> TYPE: PRT
<213> ORGANISM: artificial sequence
<220> FEATURE:
<223> OTHER INFORMATION: light chain of ANTIBODY A

<400> SEQUENCE: 8

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 9
<211> LENGTH: 30
<212> TYPE: DNA
<213> ORGANISM: artificial sequence
<220> FEATURE:
<223> OTHER INFORMATION: CDR1 heavy chain

<400> SEQUENCE: 9
ggatttacct ttagcagcta tgcgatgagc                                      30

<210> SEQ ID NO 10
<211> LENGTH: 10
<212> TYPE: PRT
<213> ORGANISM: artificial sequence
<220> FEATURE:
<223> OTHER INFORMATION: CDR1 heavy chain

<400> SEQUENCE: 10

Gly Phe Thr Phe Ser Ser Tyr Ala Met Ser
1               5                   10

<210> SEQ ID NO 11
<211> LENGTH: 51
<212> TYPE: DNA
<213> ORGANISM: artificial sequence
<220> FEATURE:
<223> OTHER INFORMATION: CDR2 heavy chain

<400> SEQUENCE: 11
gctattaatg cttctggtac tcgtacttat tatgctgatt ctgttaaggg t              51

<210> SEQ ID NO 12
<211> LENGTH: 17
<212> TYPE: PRT
<213> ORGANISM: artificial sequence
<220> FEATURE:
<223> OTHER INFORMATION: CDR2 heavy chain

<400> SEQUENCE: 12

Ala Ile Asn Ala Ser Gly Thr Arg Thr Tyr Tyr Ala Asp Ser Val Lys
1               5                   10                  15

Gly

<210> SEQ ID NO 13
<211> LENGTH: 51
<212> TYPE: DNA
<213> ORGANISM: artificial sequence
<220> FEATURE:
<223> OTHER INFORMATION: CDR3 heavy chain

<400> SEQUENCE: 13
ggtaagggta atactcataa gccttatggt tatgttcgtt attttgatgt t              51

```
<210> SEQ ID NO 14
<211> LENGTH: 17
<212> TYPE: PRT
<213> ORGANISM: artificial sequence
<220> FEATURE:
<223> OTHER INFORMATION: CDR3 heavy chain

<400> SEQUENCE: 14

Gly Lys Gly Asn Thr His Lys Pro Tyr Gly Tyr Val Arg Tyr Phe Asp
1               5                   10                  15

Val

<210> SEQ ID NO 15
<211> LENGTH: 36
<212> TYPE: DNA
<213> ORGANISM: artificial sequence
<220> FEATURE:
<223> OTHER INFORMATION: CDR1 light chain

<400> SEQUENCE: 15
agagcgagcc agagcgtgag cagcagctat ctggcg                            36

<210> SEQ ID NO 16
<211> LENGTH: 12
<212> TYPE: PRT
<213> ORGANISM: artificial sequence
<220> FEATURE:
<223> OTHER INFORMATION: CDR1 light chain

<400> SEQUENCE: 16

Arg Ala Ser Gln Ser Val Ser Ser Ser Tyr Leu Ala
1               5                   10

<210> SEQ ID NO 17
<211> LENGTH: 21
<212> TYPE: DNA
<213> ORGANISM: artificial sequence
<220> FEATURE:
<223> OTHER INFORMATION: CDR2 light chain

<400> SEQUENCE: 17
ggcgcgagca gccgtgcaac t                                            21

<210> SEQ ID NO 18
<211> LENGTH: 7
<212> TYPE: PRT
<213> ORGANISM: artificial sequence
<220> FEATURE:
<223> OTHER INFORMATION: CDR2 light chain

<400> SEQUENCE: 18

Gly Ala Ser Ser Arg Ala Thr
1               5

<210> SEQ ID NO 19
<211> LENGTH: 24
<212> TYPE: DNA
<213> ORGANISM: artificial sequence
<220> FEATURE:
<223> OTHER INFORMATION: CDR3 light chain

<400> SEQUENCE: 19
cttcagattt ataatatgcc tatt                                         24

<210> SEQ ID NO 20
```

```
<211> LENGTH: 8
<212> TYPE: PRT
<213> ORGANISM: artificial sequence
<220> FEATURE:
<223> OTHER INFORMATION: CDR3 light chain

<400> SEQUENCE: 20

Leu Gln Ile Tyr Asn Met Pro Ile
1               5

<210> SEQ ID NO 21
<211> LENGTH: 648
<212> TYPE: DNA
<213> ORGANISM: artificial sequence
<220> FEATURE:
<223> OTHER INFORMATION: light chain of ANTIBODY A

<400> SEQUENCE: 21
gatatcgtgc tgacccagag cccggcgacc ctgagcctgt ctccgggcga acgtgcgacc    60
ctgagctgca gcgagcca gagcgtgagc agcagctatc tggcgtggta ccagcagaaa    120
ccaggtcaag caccgcgtct attaatttat ggcgcgagca gccgtgcaac tggggtcccg    180
gcgcgtttta gcggctctgg atccggcacg gattttaccc tgaccattag cagcctggaa    240
cctgaagact ttgcgactta ttattgcctt cagatttata atatgcctat taccttggc    300 cagggtacga agttgaaat taaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgttag                648

<210> SEQ ID NO 22
<211> LENGTH: 215
<212> TYPE: PRT
<213> ORGANISM: artificial sequence
<220> FEATURE:
<223> OTHER INFORMATION: light chain of ANTIBODY A

<400> SEQUENCE: 22

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 23
<211> LENGTH: 3984
<212> TYPE: DNA
<213> ORGANISM: artificial sequence
<220> FEATURE:
<223> OTHER INFORMATION: alternative sequence encoding heavy chain with
      Fc-region of ANTIBODY A

<400> SEQUENCE: 23
atggagtttg ggctgagctg ggttttcctc gttgctcttt taagaggtga ttcatggaga      60
aatagagaga ctgagtgtga gtgaacatga gtgagaaaaa ctggatttgt gtggcatttt     120
ctgataacgg tgtccttctg tttgcaggtg tccagtgtca ggtggagctg gtggagtctg     180
ggggaggcct ggtccagcct ggggggtccc tgagactctc ctgtgcagcg tctggattca     240
ccttcagtag ctatgccatg agctgggtcc gccaggctcc aggcaagggg ctcgagtggg     300
tgtccgccat aaacgccagc ggtacccgca cctactatgc agactccgtg aagggccgat     360
tcaccatctc cagagacaat tccaagaaca cgctgtatct gcaaatgaac agcctgagag     420
ccgaggacac ggctgtgtat tactgtgcga gaggcaaggg gaacacccac aagccctacg     480
gctacgtacg ctactttgac gtgtggggcc aaggaaccct ggtcaccgtc tcctcaggtg     540
agtcctcaca acctctctcc tgcggccgca gcttgaagtc tgaggcagaa tcttgtccag     600
ggtctatcgg actcttgtga gaattagggg ctgacagttg atggtgacaa tttcagggtc     660
agtgactgtc tggtttctct gaggtgagac tggaatatag gtcaccttga agactaaaga     720
ggggtccagg ggcttttctg cacaggcagg aacagaatg tggaacaatg acttgaatgg     780
ttgattcttg tgtgacacca gaattggca taatgtctga gttgcccaag ggtgatctta     840
gctagactct ggggttttg tcgggtacag aggaaaaacc cactattgtg attactatgc     900 tatgactac tggggtcaag gaacctcagt caccgtctcc tcaggtaaga atggcctctc     960
caggtcttta tttttaacct tgttatgga gttttctgag cattgcagac taatcttgga    1020
tatttgccct gagggagccg gctgagaaa gttgggaaat aaatctgtct agggatctca    1080
gagcctttag gacagattat ctccacatct ttgaaaaact aagaatctgt gtgatggtgt    1140
tggtggagtc cctggatgat gggataggga ctttggaggc tcatttgagg agatgctaa    1200 aacaatccta tggctggagg atagttgggg ctgtagttg agatttttca gttttttagaa    1260 tgaagtatta gctgcaatac ttcaaggacc acctctgtga caaccatttt atacagtatc    1320
caggcatagg gacaaaaagt ggagtgggc actttcttta gatttgtgag gaatgttcca    1380
cactagattg tttaaaactt catttgttgg aaggagctgt cttagtgatt gagtcaaggg    1440
agaaaggcat ctagcctcgg tctcaaaagg gtagttgctg tctagagagg tctggtggag    1500
cctgcaaaag tccagctttc aaaggaacac agaagtatgt gtatggaata ttagaagatg    1560
```

```
ttgcttttac tcttaagttg gttcctagga aaaatagtta aatactgtga ctttaaaatg   1620
tgagagggtt ttcaagtact cattttttta aatgtccaaa attttttgtca atcaatttga   1680 ggtcttgttt gtgtagaact gacattactt aaagtttaac cgaggaatgg gagtgaggct   1740
ctctcatacc ctattcagaa ctgactttta acaataataa attaagttta aatattttt    1800 aaatgaattg agcaatgttg agttgagtca agatggccga tcagaaccgg aacacctgca   1860
gcagctggca ggaagcaggt catgtggcaa ggctatttgg ggaagggaaa ataaaaccac   1920
taggtaaact tgtagctgtg gtttgaagaa gtggttttga aacactctgt ccagccccac   1980
caaaccgaaa gtccaggctg agcaaaacac cacctgggta atttgcattt ctaaaataag   2040
ttgaggattc agccgaaact ggagaggtcc tcttttaact tattgagttc aacctttaa    2100 ttttagcttg agtagttcta gtttccccaa acttaagttt atcgacttct aaaatgtatt   2160
tagaattcga gctcggtaca gctttctggg gcaggcagg cctgaccttg gctttggggc    2220
agggaggggg ctaaggtgag gcaggtggcg ccagcaggtg cacacccaat gcccatgagc   2280
ccagacactg gacgctgaac ctcgcggaca gttaagaacc caggggcctc tgcgcctggg   2340
cccagctctg tcccacaccg cggtcacatg gcaccacctc tcttgcagcc tccaccaagg   2400
gcccatcggt cttccccctg gcaccctcct ccaagagcac ctctggggc acagcggccc    2460 tgggctgcct ggtcaaggac tacttccccg aaccggtgac ggtgtcgtgg aactcaggcg   2520
ccctgaccag cggcgtgcac accttcccgg ctgtcctaca gtcctcagga ctctactccc   2580
tcagcagcgt ggtgaccgtg ccctccagca gcttgggcac ccagacctac atctgcaacg   2640
tgaatcacaa gcccagcaac accaaggtgg acaagaaagt tggtgagagg ccagcacagg   2700
gagggagggt gtctgctgga agccaggctc agcgctcctg cctggacgca tcccggctat   2760
gcagccccag tccagggcag caaggcaggc cccgtctgcc tcttcacccg gagcctctgc   2820
ccgccccact catgctcagg gagagggtct ctggcttttt cccaggctc tgggcaggca    2880 caggctaggt gcccctaacc caggccctgc acacaaaggg gcaggtgctg ggctcagacc   2940
tgccaagagc catatccggg aggaccctgc ccctgaccta agcccacccc aaaggccaaa   3000
ctctccactc cctcagctcg gacaccttct ctcctcccag attccagtaa ctcccaatct   3060
tctctctgca gagcccaaat cttgtgacaa aactcacaca tgcccaccgt gcccaggtaa   3120
gccagcccag gcctcgccct ccagctcaag gcgggacagg tgccctagag tagcctgcat   3180
ccagggacag gccccagccg ggtgctgaca cgtccacctc catctcttcc tcagcacctg   3240
aactcctggg gggaccgtca gtcttcctct tccccccaaa acccaaggac accctcatga   3300
tctcccggac ccctgaggtc acatgcgtgg tggtggacgt gagccacgaa gaccctgagg   3360
tcaagttcaa ctggtacgtg gacggcgtgg aggtgcataa tgccaagaca aagccgcggg   3420
aggagcagta caacagcacg taccgtgtgg tcagcgtcct caccgtcctg caccaggact   3480
ggctgaatgg caaggagtac aagtgcaagg tctccaacaa agccctccca gcccccatcg   3540
agaaaaccat ctccaaagcc aaaggtggga cccgtggggt gcgagggcca catggacaga   3600
ggccggctcg gcccaccctc tgccctgaga gtgaccgctg taccaacctc tgtccctaca   3660
gggcagcccc gagaaccaca ggtgtacacc ctgcccccat cccgggatga gctgaccaag   3720
aaccaggtca gcctgacctg cctggtcaaa ggcttctatc ccagcgacat cgccgtggag   3780
tgggagagca atgggcagcc ggagaacaac tacaagacca cgcctcccgt gctggactcc   3840
gacggctcct tcttcctcta cagcaagctc accgtggaca gagcaggtg gcagcagggg   3900 aacgtcttct catgctccgt gatgcatgag gctctgcaca accactacac gcagaagagc   3960
```
ctctccctgt ccccgggcaa atga                                          3984

<210> SEQ ID NO 24
<211> LENGTH: 3202
<212> TYPE: DNA
<213> ORGANISM: artificial sequence
<220> FEATURE:
<223> OTHER INFORMATION: alternative sequence encoding light chain of
      ANTIBODY A

<400> SEQUENCE: 24

| | |
|---|---|
| atggacatga gggtcctcgc tcagctcctg gggctcctgc tgctctgttt cccaggtaag | 60 |
| gatggagaac actagcagtt tactcagccc agggtgctca gtactgcttt actattcagg | 120 |
| gaaattctct tacaacatga ttaattgtgt ggacatttgt ttttatgttt ccaatctcag | 180 |
| gcgccagatg tgatatcgtg ttgacgcagt ctccagccac cctgtctttg tctccagggg | 240 |
| aaagagccac cctctcctgc cgggccagtc agagtgttag cagcagctac ttagcctggt | 300 |
| accagcagaa acctggccag gcgcccaggc tcctcatcta tggcgcatcc agcagggcca | 360 |
| ctggcgtgcc agccaggttc agtggcagtg gtctgggac agacttcact ctcaccatca | 420 |
| gcagcctgga gcctgaagat ttcgcgacct attactgtct gcagatttac aacatgccta | 480 |
| tcacgttcgg ccaagggacc aaggtggaaa tcaaacgtga gtagaattta actttgcgg | 540 |
| ccgcctagcg tttaagtgg gagatttgga ggggatgagg aatgaaggaa cttcaggata | 600 |
| gaaagggct gaagtcaagt tcagctccta aaatggatgt gggagcaaac tttgaagata | 660 |
| aactgaatga cccagaggat gaaacagcgc agatcaaaga ggggcctgga gctctgagaa | 720 |
| gagaaggaga ctcatccgtg ttgagtttcc acaagtactg tcttgagttt tgcaataaaa | 780 |
| gtgggatagc agagttgagt gagccgtagg ctgagttctc tcttttgtct cctaagtttt | 840 |
| tatgactaca aaaatcagta gtatgtcctg aaataatcat taagctgttt gaaagtatga | 900 |
| ctgcttgcca tgtagatacc atgtcttgct gaatgatcag aagaggtgtg actcttattc | 960 |
| taaaatttgt cacaaaatgt caaaatgaga gactctgtag gaacgagtcc ttgacagaca | 1020 |
| gctcaagggg ttttttttcct ttgtctcatt tctacatgaa agtaaatttg aaatgatctt | 1080 |
| ttttattata agagtagaaa tacagttggg tttgaactat atgttttaat ggccacggtt | 1140 |
| ttgtaagaca tttggtcctt tgttttccca gttattactc gattgtaatt ttatatcgcc | 1200 |
| agcaatggac tgaaacggtc cgcaacctct tctttacaac tgggtgacct cgcggctgtg | 1260 |
| ccagccattt ggcgttcacc ctgccgctaa gggccatgtg aacccccgcg tagcatccc | 1320 |
| ttgctccgcg tggaccactt tcctgaggca cagtgatagg aacagagcca ctaatctgaa | 1380 |
| gagaacagag atgtgacaga ctacactaat gtgagaaaaa caaggaaagg gtgacttatt | 1440 |
| ggagatttca gaaataaaat gcatttatta ttatattccc ttattttaat tttctattag | 1500 |
| ggaattagaa agggcataaa ctgctttatc cagtgttata ttaaaagctt aatgtatata | 1560 |
| atcttttaga ggtaaaatct acagccagca aaagtcatgg taaatattct ttgactgaac | 1620 |
| tctcactaaa ctcctctaaa ttatatgtca tattaactgg ttaaattaat ataaatttgt | 1680 |
| gacatgacct taactggtta ggtaggatat ttttcttcat gcaaaaatat gactaataat | 1740 |
| aatttagcac aaaaatattt cccaatactt taattctgtg atagaaaaat gtttaactca | 1800 |
| gctactataa tcccataatt ttgaaaacta tttattagct tttgtgtttg acccttccct | 1860 |
| agccaaaggc aactatttaa ggacccttta aaactcttga aactacttta gagtcattaa | 1920 |
| gttatttaac cactttaat tactttaaaa tgatgtcaat tcccttttaa ctattaattt | 1980 |

```
attttaaggg gggaaaggct gctcataatt ctattgtttt tcttggtaaa gaactctcag    2040
ttttcgtttt tactacctct gtcacccaag agttggcatc tcaacagagg ggactttccg    2100
agaggccatc tggcagttgc ttaagatcag aagtgaagtc tgccagttcc tcccaggcag    2160
gtggcccaga ttacagttga cctgttctgg tgtggctaaa aattgtccca tgtggttaca    2220
aaccattaga ccagggtctg atgaattgct cagaatattt ctggacaccc aaatacagac    2280
cctggcttaa ggccctgtcc atacagtagg tttagcttgg ctacaccaaa ggaagccata    2340
cagaggctaa tatcagagta ttcttggaag agacaggaga aaatgaaagc cagtttctgc    2400
tcttacctta tgtgcttgtg ttcagactcc caaacatcag gagtgtcaga taaactggtc    2460
tgaatctctg tctgaagcat ggaactgaaa agaatgtagt ttcagggaag aaaggcaata    2520
gaaggaagcc tgagaatacg gatcaattct aaactctgag ggggtcggat gacgtggcca    2580
ttctttgcct aaagcattga gtttactgca aggtcagaaa agcatgcaaa gccctcagaa    2640
tggctgcaaa gagctccaac aaaacaattt agaactttat taaggaatag ggggaagcta    2700
ggaagaaact caaaacatca agattttaaa tacgcttctt ggtctccttg ctataattat    2760
ctgggataag catgctgttt tctgtctgtc cctaacatgc cctgtgatta ccgcaaaca    2820 acacacccaa gggcagaact tgttactta aacaccatcc tgtttgcttc tttcctcagg    2880
aactgtggct gcaccatctg tcttcatctt cccgccatct gatgagcagt tgaaatctgg    2940
aactgcctct gttgtgtgcc tgctgaataa cttctatccc agagaggcca agtacagtg    3000 gaaggtggat aacgcccctcc aatcgggtaa ctcccaggag agtgtcacag agcaggacag    3060
caaggacagc acctacagcc tcagcagcac cctgacgctg agcaaagcag actacgagaa    3120
acacaaagtc tacgcctgcg aagtcaccca tcagggcctg agctcgcccg tcacaaagag    3180
cttcaacagg ggagagtgtt ag                                             3202
```

<210> SEQ ID NO 25
<211> LENGTH: 1428
<212> TYPE: DNA
<213> ORGANISM: artificial sequence
<220> FEATURE:
<223> OTHER INFORMATION: heavy chain with Fc region of ANTIBODY A and
      with leader sequence

<400> SEQUENCE: 25

```
atgaaacacc tgtggttctt cctcctgctg gtggcagctc ccagatgggt cctgtcccag     60
gtggaattgg tggaaagcgg cggcggcctg gtgcaaccgg cggcagcct gcgtctgagc    120 tgcgcggcct ccggatttac ctttagcagc tatgcgatga gctgggtgcg ccaagcccct    180
gggaagggtc tcgagtgggt gagcgctatt aatgcttctg gtactcgtac ttattatgct    240
gattctgtta agggtcgttt taccatttca cgtgataatt cgaaaaacac cctgtatctg    300
caaatgaaca gcctgcgtgc ggaagatacg gccgtgtatt attgcgcgcg tggtaagggt    360
aatactcata gccttatgg ttatgttcgt tattttgatg tttggggcca aggcaccctg    420
gtgacggtta gctcagcctc caccaagggt ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
```

```
gaactcctgg ggggaccgtc agtcttcctc ttcccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgggtg gtcagcgtcc tcaccgtcct gcaccaggac   1020
tggctgaatg gcaaggagta caagtgcaag gtctccaaca aagccctccc agccccatc    1080 gagaaaacca tctccaaagc caagggcag ccccgagaac cacaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaatga              1428
```

<210> SEQ ID NO 26
<211> LENGTH: 475
<212> TYPE: PRT
<213> ORGANISM: artificial sequence
<220> FEATURE:
<223> OTHER INFORMATION: heavy chain with Fc region of ANTIBODY A and with leader sequence

<400> SEQUENCE: 26

```
Met Lys His Leu Trp Phe Phe Leu Leu Leu Val Ala Ala Pro Arg Trp
1               5                   10                  15

Val Leu Ser Gln Val Glu Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
        50                  55                  60

Glu Trp Val Ser Ala Ile Asn Ala Ser Gly Thr Arg Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Lys Gly Asn Thr His Lys Pro Tyr Gly Tyr
        115                 120                 125

Val Arg Tyr Phe Asp Val Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240
```

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 27
<211> LENGTH: 708
<212> TYPE: DNA
<213> ORGANISM: artificial sequence
<220> FEATURE:
<223> OTHER INFORMATION: light chain of ANTIBODY A with leader sequence

<400> SEQUENCE: 27
atggtgttgc agacccaggt cttcatttct ctgttgctct ggatctctgg tgcctacggg      60
gatatcgtgc tgacccagag cccggcgacc ctgagcctgt ctccgggcga acgtgcgacc     120
ctgagctgca gcgagcca gagcgtgagc agcagctatc tggcgtggta ccagcagaaa     180
ccaggtcaag caccgcgtct attaatttat ggcgcgagca gccgtgcaac tggggtcccg     240
gcgcgtttta gcggctctgg atccggcacg gattttaccc tgaccattag cagcctggaa     300
cctgaagact ttgcgactta ttattgcctt cagatttata atatgcctat tacctttggc     360
cagggtacga agttgaaat taacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag acagcacct acagcctcag cagcaccctg     600
acgctgagca agcagactat cgagaaacac aaagtctacg cctgcgaagt cacccatcag     660
ggcctgagct cgcccgtcac aaagagcttc aacaggggag agtgttag              708

```
<210> SEQ ID NO 28
<211> LENGTH: 235
<212> TYPE: PRT
<213> ORGANISM: artificial sequence
<220> FEATURE:
<223> OTHER INFORMATION: light chain of ANTIBODY A with leader sequence

<400> SEQUENCE: 28

Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Leu Gln Ile
                100                 105                 110

Tyr Asn Met Pro Ile Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 29
<211> LENGTH: 31
<212> TYPE: DNA
<213> ORGANISM: artificial sequence
<220> FEATURE:
<223> OTHER INFORMATION: MS-Roche #7.9.H7_Ig_kappa sense primer

<400> SEQUENCE: 29
acgtaagctt gccgccacca tggtgttgca g                               31

<210> SEQ ID NO 30
<211> LENGTH: 28
<212> TYPE: DNA
<213> ORGANISM: artificial sequence
<220> FEATURE:
<223> OTHER INFORMATION: MS-Roche #7.9.H7_Ig_kappa antisense primer

<400> SEQUENCE: 30
acgtgaattc ctaacactct cccctgtt                                   28
```

<210> SEQ ID NO 31
<211> LENGTH: 31
<212> TYPE: DNA
<213> ORGANISM: artificial sequence
<220> FEATURE:
<223> OTHER INFORMATION: MS-Roche #7.9.H7_IgG1 sense primer

<400> SEQUENCE: 31
acgtaagctt gccgccacca tgaaacacct g                                31

<210> SEQ ID NO 32
<211> LENGTH: 28
<212> TYPE: DNA
<213> ORGANISM: artificial sequence
<220> FEATURE:
<223> OTHER INFORMATION: MS-Roche #7.9.H7_IgG1 antisense primer

<400> SEQUENCE: 32
acgtgaattc tcatttaccc ggagacag                                    28

<210> SEQ ID NO 33
<211> LENGTH: 10
<212> TYPE: PRT
<213> ORGANISM: Artificial
<220> FEATURE:
<223> OTHER INFORMATION: Synthetic Construct

<400> SEQUENCE: 33

Ile Ser Glu Val Lys Met Asp Ala Glu Phe
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic Construct

<400> SEQUENCE: 34

Ser Glu Val Lys Met Asp Ala Glu Phe Arg
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic Construct

<400> SEQUENCE: 35

Glu Val Lys Met Asp Ala Glu Phe Arg His
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic Construct

<400> SEQUENCE: 36

Val Lys Met Asp Ala Glu Phe Arg His Asp
1               5                   10

<210> SEQ ID NO 37
<211> LENGTH: 10

```
<212> TYPE: PRT
<213> ORGANISM: Artificial
<220> FEATURE:
<223> OTHER INFORMATION: Synthetic Construct

<400> SEQUENCE: 37

Lys Met Asp Ala Glu Phe Arg His Asp Ser
1               5                   10

<210> SEQ ID NO 38
<211> LENGTH: 9
<212> TYPE: PRT
<213> ORGANISM: Artificial
<220> FEATURE:
<223> OTHER INFORMATION: Synthetic Construct

<400> SEQUENCE: 38

Met Asp Ala Glu Phe Arg His Asp Ser
1               5

<210> SEQ ID NO 39
<211> LENGTH: 10
<212> TYPE: PRT
<213> ORGANISM: Artificial
<220> FEATURE:
<223> OTHER INFORMATION: Synthetic Construct

<400> SEQUENCE: 39

Asp Ala Glu Phe Arg His Asp Ser Gly Tyr
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic Construct

<400> SEQUENCE: 40

Ala Glu Phe Arg His Asp Ser Gly Tyr Glu
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic Construct

<400> SEQUENCE: 41

Glu Phe Arg His Asp Ser Gly Tyr Glu Val
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic Construct

<400> SEQUENCE: 42

Phe Arg His Asp Ser Gly Tyr Glu Val His
1               5                   10

<210> SEQ ID NO 43
<211> LENGTH: 10
<212> TYPE: PRT
```

<213> ORGANISM: Artificial
<220> FEATURE:
<223> OTHER INFORMATION: Synthetic Construct

<400> SEQUENCE: 43

Gln Lys Leu Val Phe Phe Ala Glu Asp Val
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic Construct

<400> SEQUENCE: 44

Lys Leu Val Phe Phe Ala Glu Asp Val Gly
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic Construct

<400> SEQUENCE: 45

Leu Val Phe Phe Ala Glu Asp Val Gly Ser
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic Construct

<400> SEQUENCE: 46

Val Phe Phe Ala Glu Asp Val Gly Ser Asn
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic Construct

<400> SEQUENCE: 47

Phe Phe Ala Glu Asp Val Gly Ser Asn Lys
1               5                   10

<210> SEQ ID NO 48
<211> LENGTH: 9
<212> TYPE: PRT
<213> ORGANISM: Artificial
<220> FEATURE:
<223> OTHER INFORMATION: Synthetic Construct

<400> SEQUENCE: 48

Phe Ala Glu Asp Val Gly Ser Asn Lys
1               5

<210> SEQ ID NO 49
<211> LENGTH: 10
<212> TYPE: PRT
<213> ORGANISM: Artificial

```
<220> FEATURE:
<223> OTHER INFORMATION: Synthetic Construct

<400> SEQUENCE: 49

Arg His Asp Ser Gly Tyr Glu Val His His
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic Construct

<400> SEQUENCE: 50

His Asp Ser Gly Tyr Glu Val His His Gln
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic Construct

<400> SEQUENCE: 51

Asp Ser Gly Tyr Glu Val His His Gln Lys
1               5                   10

<210> SEQ ID NO 52
<211> LENGTH: 10
<212> TYPE: PRT
<213> ORGANISM: Artificial
<220> FEATURE:
<223> OTHER INFORMATION: Synthetic Construct

<400> SEQUENCE: 52

Ser Gly Tyr Glu Val His His Gln Lys Leu
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic Construct

<400> SEQUENCE: 53

Glu Val His His Gln Lys Leu Val Phe Phe
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic Construct

<400> SEQUENCE: 54

Gly Tyr Glu Val His His Gln Lys Leu Val
1               5                   10

<210> SEQ ID NO 55
<211> LENGTH: 10
<212> TYPE: PRT
<213> ORGANISM: Artificial
<220> FEATURE:
```

<223> OTHER INFORMATION: Synthetic Construct

<400> SEQUENCE: 55

Tyr Glu Val His His Gln Lys Leu Val Phe
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic Construct

<400> SEQUENCE: 56

Val His His Gln Lys Leu Val Phe Phe Ala
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic Construct

<400> SEQUENCE: 57

His His Gln Lys Leu Val Phe Phe Ala Glu
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic Construct

<400> SEQUENCE: 58

His Gln Lys Leu Val Phe Phe Ala Glu Asp
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic Construct

<400> SEQUENCE: 59

Phe Ala Glu Asp Val Gly Ser Asn Lys Gly
1               5                   10

<210> SEQ ID NO 60
<211> LENGTH: 10
<212> TYPE: PRT
<213> ORGANISM: Artificial
<220> FEATURE:
<223> OTHER INFORMATION: Synthetic Construct

<400> SEQUENCE: 60

Ala Glu Asp Val Gly Ser Asn Lys Gly Ala
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic Construct

```
<400> SEQUENCE: 61

Glu Asp Val Gly Ser Asn Lys Gly Ala Ile
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic Construct

<400> SEQUENCE: 62

Asp Val Gly Ser Asn Lys Gly Ala Ile Ile
1               5                   10

<210> SEQ ID NO 63
<211> LENGTH: 10
<212> TYPE: PRT
<213> ORGANISM: Artificial
<220> FEATURE:
<223> OTHER INFORMATION: Synthetic Construct

<400> SEQUENCE: 63

Val Gly Ser Asn Lys Gly Ala Ile Ile Gly
1               5                   10

<210> SEQ ID NO 64
<211> LENGTH: 10
<212> TYPE: PRT
<213> ORGANISM: Artificial
<220> FEATURE:
<223> OTHER INFORMATION: Synthetic Construct

<400> SEQUENCE: 64

Gly Ser Asn Lys Gly Ala Ile Ile Gly Leu
1               5                   10

<210> SEQ ID NO 65
<211> LENGTH: 10
<212> TYPE: PRT
<213> ORGANISM: Artificial
<220> FEATURE:
<223> OTHER INFORMATION: Synthetic Construct

<400> SEQUENCE: 65

Ser Asn Lys Gly Ala Ile Ile Gly Leu Met
1               5                   10

<210> SEQ ID NO 66
<211> LENGTH: 10
<212> TYPE: PRT
<213> ORGANISM: Artificial
<220> FEATURE:
<223> OTHER INFORMATION: Synthetic Construct

<400> SEQUENCE: 66

Asn Lys Gly Ala Ile Ile Gly Leu Met Val
1               5                   10

<210> SEQ ID NO 67
<211> LENGTH: 10
<212> TYPE: PRT
<213> ORGANISM: Artificial
<220> FEATURE:
<223> OTHER INFORMATION: Synthetic Construct
```

```
<400> SEQUENCE: 67

Lys Gly Ala Ile Ile Gly Leu Met Val Gly
1               5                   10

<210> SEQ ID NO 68
<211> LENGTH: 10
<212> TYPE: PRT
<213> ORGANISM: Artificial
<220> FEATURE:
<223> OTHER INFORMATION: Synthetic Construct

<400> SEQUENCE: 68

Gly Ala Ile Ile Gly Leu Met Val Gly Gly
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic Construct

<400> SEQUENCE: 69

Ala Ile Ile Gly Leu Met Val Gly Gly Val
1               5                   10

<210> SEQ ID NO 70
<211> LENGTH: 10
<212> TYPE: PRT
<213> ORGANISM: Artificial
<220> FEATURE:
<223> OTHER INFORMATION: Synthetic Construct

<400> SEQUENCE: 70

Ile Ile Gly Leu Met Val Gly Gly Val Val
1               5                   10

<210> SEQ ID NO 71
<211> LENGTH: 10
<212> TYPE: PRT
<213> ORGANISM: Artificial
<220> FEATURE:
<223> OTHER INFORMATION: Synthetic Construct

<400> SEQUENCE: 71

Ile Gly Leu Met Val Gly Gly Val Val Ile
1               5                   10

<210> SEQ ID NO 72
<211> LENGTH: 10
<212> TYPE: PRT
<213> ORGANISM: Artificial
<220> FEATURE:
<223> OTHER INFORMATION: Synthetic Construct

<400> SEQUENCE: 72

Gly Leu Met Val Gly Gly Val Val Ile Ala
1               5                   10

<210> SEQ ID NO 73
<211> LENGTH: 10
<212> TYPE: PRT
<213> ORGANISM: Artificial
<220> FEATURE:
<223> OTHER INFORMATION: Synthetic Construct

<400> SEQUENCE: 73
```

```
Leu Met Val Gly Gly Val Val Ile Ala Thr
1               5                   10

<210> SEQ ID NO 74
<211> LENGTH: 10
<212> TYPE: PRT
<213> ORGANISM: Artificial
<220> FEATURE:
<223> OTHER INFORMATION: Synthetic Construct

<400> SEQUENCE: 74

Met Val Gly Gly Val Val Ile Ala Thr Val
1               5                   10

<210> SEQ ID NO 75
<211> LENGTH: 10
<212> TYPE: PRT
<213> ORGANISM: Artificial
<220> FEATURE:
<223> OTHER INFORMATION: Synthetic Construct

<400> SEQUENCE: 75

Val Gly Gly Val Val Ile Ala Thr Val Ile
1               5                   10

<210> SEQ ID NO 76
<211> LENGTH: 11
<212> TYPE: PRT
<213> ORGANISM: Artificial
<220> FEATURE:
<223> OTHER INFORMATION: Synthetic Construct

<400> SEQUENCE: 76

Val Gly Gly Val Val Ile Ala Thr Val Ile Val
1               5                   10
```